United States Patent [19]

Handa et al.

[11] Patent Number: 5,620,987
[45] Date of Patent: Apr. 15, 1997

[54] AMINO ACID DERIVATIVES

[75] Inventors: Balraj K. Handa, Welwyn Garden City; Peter J. Machin, London; Joseph A. Martin, West Common; Sally Redshaw, Stevenage; Gareth J. Thomas, Welwyn, all of England

[73] Assignee: Hoffmann-La Roche Inc., Nutley, N.J.

[21] Appl. No.: 398,478

[22] Filed: Apr. 10, 1995

Related U.S. Application Data

[62] Division of Ser. No. 916,812, Jul. 20, 1992, Pat. No. 5,446,161, which is a division of Ser. No. 362,621, Jun. 5, 1989, Pat. No. 5,157,041.

[30] Foreign Application Priority Data

Jun. 13, 1988 [GB] United Kingdom ............... 8813940
Apr. 10, 1989 [GB] United Kingdom ............... 8908035

[51] Int. Cl.$^6$ .................... C07D 217/16; A61K 31/47
[52] U.S. Cl. .................. 514/307; 514/311; 514/416; 546/164; 546/165; 546/112
[58] Field of Search .................... 546/164, 165, 546/112; 514/307, 311, 416

[56] References Cited

U.S. PATENT DOCUMENTS

| 4,402,969 | 9/1983 | Greenlee et al. | 514/423 |
|---|---|---|---|
| 4,470,973 | 9/1984 | Natarajan et al. | 54/19 |
| 4,575,503 | 3/1986 | Watthey | 514/213 |
| 4,621,092 | 11/1986 | Natarajan et al. | 514/343 |
| 4,636,522 | 1/1987 | Gordon | 514/423 |
| 4,638,010 | 1/1987 | Weller et al. | 514/423 |
| 4,720,484 | 1/1988 | Vincent et al. | 514/18 |
| 4,812,442 | 3/1989 | Boger et al. | 514/18 |
| 4,863,905 | 9/1989 | Hadspeth et al. | 514/18 |
| 4,965,250 | 10/1990 | Vincent et al. | 514/18 |
| 5,008,273 | 4/1991 | Schnorrenberg et al. | 514/301 |
| 5,157,041 | 10/1992 | Handa et al. | 514/314 |
| 5,196,438 | 3/1993 | Martin | 514/311 |

FOREIGN PATENT DOCUMENTS

| 190058 | 1/1986 | European Pat. Off. . |
|---|---|---|
| 189203 | 1/1986 | European Pat. Off. . |
| 230082 | 12/1986 | European Pat. Off. . |
| 229667 | 1/1987 | European Pat. Off. . |
| 230266 | 1/1987 | European Pat. Off. . |
| 282374 | 2/1988 | European Pat. Off. . |
| 264106 | 4/1988 | European Pat. Off. . |
| 292800 | 5/1988 | European Pat. Off. . |
| 309841 | 9/1988 | European Pat. Off. . |
| 337714 | 4/1989 | European Pat. Off. . |
| 346847 | 6/1989 | European Pat. Off. . |
| 342541 | 11/1989 | European Pat. Off. . |
| WO88/00939 | 2/1988 | WIPO . |

OTHER PUBLICATIONS

C. S. Crumpacker, N. Engl. J. Med. 321:163–172 (1989).
J. Fuhrhop and G. Penzlin, *Organic Synthesis: Concepts, Methods, Starting Materials* (Verlag Chemie, Weinheim 1983) (Textbook).
M. Kotler, et al., Proc. Natl. Acad. Sci. USA 85:4185–89.
M. Miller, et al., Nature 337:576–79 (1989).
Genetic Engineering & Biotechnology Monitor, No. 33, 30 (1991).
Chem. Eng. News, 30 Apr. 1990, p. 18.
Meek, et al., Nature 343: 90–92 (1990).
McQuade, et al., Science 247:454–456 (1990).
Dreyer, et al., Proc. Natl. Acad. Sci. 86(24):9752–9756 (1989).
Jouin, et al., J. Org. Chem, 54(3):617–627 (1989).
Fray, et al., J. Org. Chem. 51(25):4828–4833 (1986).
Harris, et al., Tetrahedron 44(12):3489–3500 (1988).
Roberts, et al, Science 248:358–361 (1990).
Overton, et al., Virology 179:508–511 (1990).

*Primary Examiner*—C. Warren Ivy
*Assistant Examiner*—D. Margaret M. Mach
*Attorney, Agent, or Firm*—George W. Johnston; Dennis P. Tramaloni; Alan P. Kass

[57] ABSTRACT

Compounds of the formula

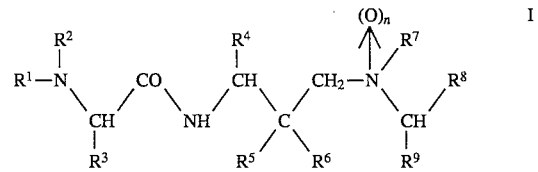

wherein $R^1$, $R^2$, $R^3$, $R^4$, $R^5$, $R^6$, and $-N(R^7)-CH(R^8)(R^9)$ are as claimed herein or their pharmaceutically acceptable acid addition salts inhibit proteases of viral origin and can be used as medicaments for the treatment of viral infections. They can be manufactured according to generally known procedures.

11 Claims, No Drawings

AMINO ACID DERIVATIVES

This is a division of application Ser. No. 07/916,812 filed Jul. 20, 1992, now U.S. Pat. No. 5,446,161, which is a Divisional of Ser. No. 07/362,621 filed Jun. 5, 1989, now U.S. Pat. No. 5,157,041.

SUMMARY OF THE INVENTION

The present invention is concerned with amino acid derivatives.

The amino acid derivatives provided by the present invention are compounds of the general formula

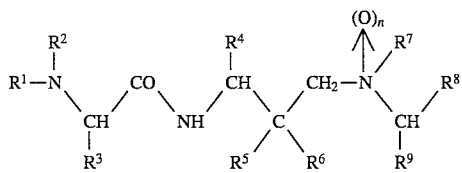

wherein n stands for zero or 1; $R^1$ represents alkoxycarbonyl, aralkoxycarbonyl, alkanoyl, cycloalkylcarbonyl, aralkanoyl, aroyl, heterocyclylcarbonyl, alkylsulphonyl, arylsulphonyl, monoaralkylcarbamoyl, cinnamoyl or α-aralkoxycarbonylaminoalkanoyl and $R^2$ represents hydrogen or $R^1$ and $R^2$ together with the nitrogen atom to which they are attached represent a cyclic imide group of the formula

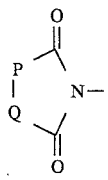

in which P and Q together represent an aromatic system; $R^3$ represents alkyl, cycloalkyl, aryl, aralkyl, heterocyclylalkyl, cyanoalkyl, alkylsulphinylalkyl, carbamoylalkyl oralkoxycarbonylalkyl or, when n stands for zero, $R^3$ can also represent alkylthioalkyl or, when n stands for 1, $R^3$ can also represent alkylsulphonylalkyl; $R^4$ represents alkyl, cycloalkyl cycloalkylalkyl, aryl or aralkyl; $R^5$ represents hydrogen and $R^6$ represents hydroxy or $R^5$ and $R^6$ together represent oxo; $R^7$ and $R^8$ together represent a trimethylene or tetramethylene group which is optionally substituted by hydroxy, alkoxycarbonylamino or acylamino or in which one —CH$_2$— group is replaced by —NH—, —N(alkoxycarbonyl)-, —N(acyl)- or —S— or which carries a fused cycloalkane, aromatic or heteroaromatic ring: and $R^9$ represents alkoxycarbonyl, monoalkylcarbamoyl, monoaralkylcarbamoyl, monoaryl- carbamoyl or a group of the formula

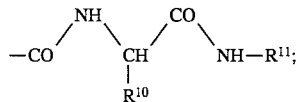

in which $R^{10}$ and $R^{11}$ each represent alkyl; and pharmaceutically acceptable acid addition salts thereof.

DETAILED DESCRIPTION

The compounds of formula I and their pharmaceutically acceptable acid addition salts are novel and possess valuable pharmacological properties. In particular, they inhibit proteases of viral origin and can be used in the prophylaxis or treatment of viral infections, particularly of infections caused by HIV and other retroid viruses.

Objects of the present invention are the compounds of formula I and their aforementioned salts per se and for use as therapeutically active substances, a process for the manufacture of said compounds and salts, intermediates used in said process, medicaments containing said compounds and salts, the use of said compounds and salts in the control or prevention of illnesses, especially in the treatment or prophylaxis of vital infections, and the use of said compounds and salts for the manufacture of medicaments for the treatment or prophylaxis of vital infections.

As used in this Specification, the term "alkyl", alone or in combination, means a straight-chain or branched-chain alkyl group containing a maximum of 8, preferably a maximum of 4, carbon atoms such as methyl, ethyl, n-propyl, isopropyl, n-butyl, isobutyl, sec.butyl, tert.butyl, pentyl, hexyl and the like. The term "alkoxy", alone or in combination, means an alkyl ether group in which the term "alkyl" has the significance given earlier, such as methoxy, ethoxy, n-propoxy, isopropoxy, n-butoxy, isobutoxy, sec.butoxy, tert.butoxy and the like. The term "cycloalkylalkyl" means an alkyl group as defined earlier which is substituted by a cycloalkyl group containing 3–8, preferably 3–6, carbon atoms such as cyclopropyl, cyclobutyl, cyclopentyl, cyclohexyl and the like. The term "aryl", alone or in combination, means a phenyl or naphthyl group which optionally carries one or more substituents selected from alkyl, alkoxy, halogen, hydroxy, amino and the like, such as phenyl, p-tolyl, 4-methoxyphenyl, 4-tert.butoxyphenyl, 4-fluorophenyl, 4-chlorophenyl, 4-hydroxyphenyl, 1-naphthyl, 2-naphthyl etc. The term "aralkyl", alone or in combination, means an alkyl group as defined earlier in which one hydrogen atom is replaced by an aryl group as defined earlier, such as benzyl, 2-phenylethyl and the like. The term "aralkoxycarbonyl", alone or in combination, means a group of the formula —C(O)—O-aralkyl in which the term "aralkyl" has the significance given earlier, such as benzyloxycarbonyl etc. The term "alkanoyl", alone or in combination, means an acyl group derived from an alkanecarboxylic acid such as acetyl, propionyl, butyryl, valeryl, 4-methylvaleryl etc. The term "cycloalkylcarbonyl" means an acyl group derived from a monocyclic or bridged cycloalkanecarboxylic acid such as cyclopropanecarbonyl, cyclohexanecarbonyl, adamantanecarbonyl etc or from a benz-fused monocyclic cycloalkanecarboxylic acid which is optionally substituted by, for example, alkanoylamino, such as 1,2,3,4-tetrahydro-2-naphthoyl, 2-acetamido-1,2,3,4-tetrahydro-2-naphthoyl. The term "aralkanoyl" means an acyl group derived from an aryl-substituted alkanecarboxylic acid such as phenylacetyl, 3-phenylpropionyl (hydrocinnamoyl), 4-phenylbutyryl, (2-naphthyl)acetyl, 4-chlorohydrocinnamoyl), 4-aminohydrocinnamoyl, 4-methoxyhydrocinnamoyl etc. The term "aroyl" means an acyl group derived from an aromatic carboxylic acid; for example an optionally substituted benzoic or naphthoic acid such as benzoyl, 4-chlorobenzoyl, 4-carboxybenzoyl, 4-(benzyloxycarbonyl)benzoyl, 1-naphthoyl, 2-naphthoyl, 6-carboxy-2-naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl etc. The heterocyclyl portion of a heterocyclylcarbonyl or heterocyclylalkyl group is a saturated, partially unsaturated or aromatic monocyclic, bicyclic or tricyclicheterocycle which contains one or more hetero atoms selected from nitrogen, oxygen and sulphur, which is optionally substituted on one or more carbon atoms by halogen, alkyl, alkoxy, oxo etc and/or on a secondary nitrogen atom (i.e. —NH—) by alkyl, aralkoxycarbonyl, alkanoyl, phenyl or phenylalkyl or on a tertiary nitrogen atom (i.e. =N—) by oxido and which is attached via a carbon atom. Examples of such heterocyclyl groups are pyrrolidinyl, piperidinyl, piperazinyl, morpholinyl, thiamorpholinyl, pyrrolyl, imidazolyl (e.g. imidazol-4-yl, 1-benzyloxycarbonylimidazol-4-yl, etc), pyrazolyl, pyridyl, pyrazinyl, pyrimidinyl, furyl, thienyl, triazolyl, oxazolyl, thiazolyl, indolyl (e.g. 2-indolyl etc), quinolyl (e.g. 2-quinolyl, 3-quinolyl, 1-oxido-2-quinolyl etc), isoquinolyl (e.g. 1-isoquinolyl, 3-isoquinolyl etc), tetrahydroquinolyl (e.g. 1,2,3,4-tetrahydro-2-quinolyl etc), 1,2,3,4-tetrahydroisoquinolyl (e.g. 1,2,3,4-tetrahydro-1-oxo-isoquinolyl etc), quinoxalinyl, β-carbolinyl and the like. The term "halogen" means fluorine, chlorine, bromine or iodine.

A cinnamoyl group denoted by $R^1$ can be unsubstituted or can carry on the phenyl ring one or more substituents selected from alkyl, alkoxy, halogen, nitro and the like.

The aromatic system denoted by P and Q together in formula (a) given earlier can be monocyclic (e.g. 1,2-phenylene or thienylene) or polycyclic (e.g. 1,2-naphthylene, 2,3-naphthylene, 1,8-naphthylene, 2,3-anthrylene etc) and can be unsubstituted or substituted by one or more substituents selected from alkyl, alkoxy, halogen and the like.

As mentioned earlier, a trimethylene or tetramethylene group denoted by $R^7$ and $R^8$ together can be optionally substituted by a hydroxy group or an alkoxycarbonylamino group (e.g. tert.butoxycarbonylamino) or an acylamino group (i.e. an alkanoylamino, cycloalkylcarbonylamino, aralkanoylamino or aroylamino group). Alternatively, one —$CH_2$— group of a trimethylene or tetramethylene group denoted by $R^7$ and $R^8$ together can be replaced by —NH—, —N(alkoxycarbonyl)-, for example —N(tert.butoxycarbonyl)-, —N(acyl)- or —S—. When a trimethylene or tetramethylene group denoted by $R^7$ and $R^8$ together carries a fused cycloalkane ring, this can be, for example, a fused cycloalkane ring containing 3–6 carbon atoms such as a fused cyclopentane, cyclohexane or like ring and when the trimethylene or tetramethylene group carries a fused aromatic or heteroaromatic ring, this can be, for example, a fused benzene, indole or thiophene ring which can be optionally substituted on one or more carbon atoms by halogen, alkyl, alkoxy etc. Thus, —N($R^7$)—CH($R^8$)($R^9$) can represent, for example, one of the following groups:

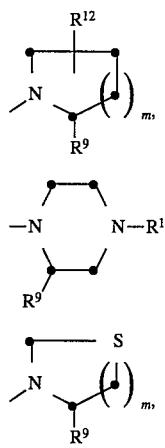

(c)

(d)

(e)

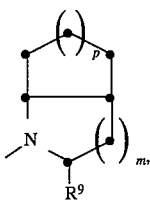

(f)

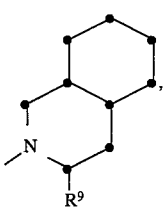

(g)

(h)

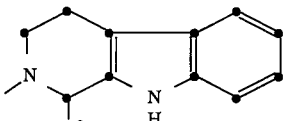

(i)

and

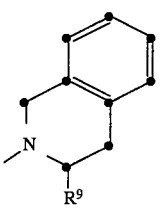

(j)

wherein $R^9$ has the significance given earlier, $R^{12}$ represents hydrogen, hydroxy, alkoxycarbonylamino or acylamino, $R^{13}$ represents hydrogen, alkoxycarbonyl or acyl, m stands for 1 or 2 and p stands for 1 or 2.

The pharmaceutically acceptable acid addition salts of the compounds of formula I are salts formed with inorganic acids, for example hydrohalic acids such as hydrochloric acid or hydrobromic acid, sulphuric acid, nitric acid, phosphoric acid etc, or with organic acids, for example acetic acid, citric acid, maleic acid, fumaric acid, tartaric acid, methanesulphonic acid, p-toluenesulphonic acid etc.

The compounds of formula I contain at least three asymmetric carbon atoms and are therefore present in the form of optically pure diastereoisomers, mixtures of diastereoisomers, diastereoisomeric racemates or mixtures of diastereoisomeric racemates. The present invention includes within its scope all of these forms.

One particular group of compounds of formula I comprises those in which n stands for zero, $R^3$ represents alkyl, cycloalkyl, aryl, aralkyl, heterocyclylalkyl, cyanoalkyl, alkylthioalkyl, carbamoylalkyl or alkoxycarbonylalkyl and $R^7$ and $R^8$ together represent a trimethylene or tetramethylene group in which one —$CH_2$-group can be replaced by —NH— or —S— or which can carry a fused cycloalkane, aromatic or heteroaromatic ring.

In the compounds of formula I hereinbefore, preferably $R^1$ represents alkoxycarbonyl, aralkoxycarbonyl, alkanoyl, cycloalkylcarbonyl, aralkanoyl, aroyl, hererocyclylcarbonyl or α-aralkoxycarbonylamino-alkanoyl, especially benzyloxycarbonyl, 2-naphthoyl, 1-hydroxy-2-naphthoyl, 3-hydroxy-2-naphthoyl, 3-benzyloxy-2-naphthoyl, 2-quinolylcarbonyl or 3-quinolylcarbonyl, and $R^2$ represents hydrogen. $R^3$ preferably represents alkyl, cyanoalkyl, alkylthioalkyl or carbamoylalkyl, especially cyanomethyl, methylthiomethyl or carbamoylmethyl. $R^4$ preferably represents aralkyl, especially benzyl. Preferably, $R^5$ represents hydrogen and $R^6$ represents hydroxy. Preferably, —N($R^7$)—CH($R^8$)($R^9$) represents one of the groups of formulae (c) to (i) hereinbefore, especially a group of formula (c) in which $R^{12}$ represents hydrogen and m stands for 2 or $R^{12}$ represents tert.butoxycarbonylamino and m stands for 1, a group of formula (d) in which $R^{13}$ represents tert.butoxycarbonyl, a group of formula (e) in which m stands for 1, a group of formula (f) in which m and p both stand for 1, or a group of formula (g), (i) or (j). With respect to $R^9$, this preferably represents alkoxycarbonyl especially tert.butoxycarbonyl, monoalkylcarbamoyl, especially isobutylcarbamoyl or tert.butylcarbamoyl, or a group of formula (b), especially one in which $R^{10}$ represents sec.butyl and $R^{11}$ represents isobutyl.

From the foregoing it will be appreciated that particularly preferred compounds of formula I are those in which $R^1$ represents benzyloxycarbonyl, 2-naphthoyl, 1-hydroxy-2-naphthoyl, 3-hydroxy-2-naphthoyl, 3-benzyloxy-2-naphthoyl, 2-quinolylcarbonyl or 3-quinolylcarbonyl and $R^2$ represents hydrogen, $R^3$ represents cyanomethyl, methylthiomethyl or carbamoylmethyl, $R^4$ represents benzyl, $R^5$ represents hydrogen and $R^6$ represents hydroxy and —N($R^7$)—CH($R^8$)($R^9$) represents a group of formula (c) hereinbefore in which $R^{12}$ represents hydrogen and m stands for 2 or $R^{12}$ represents tert.butoxycarbonylamino and m stands for 1, a group of formula (d) hereinbefore in which $R^{13}$ represents tert.butoxycarbonyl, a group of formula (e) hereinbefore in which m stands for 1, a group of formula (f) hereinbefore in which m and p both stand for 1 or a group of formula (g), (i) or (j) hereinbefore and $R^9$ represents tert.butoxycarbonyl, isobutylcarbamoyl, tert.butylcarbamoyl or a group of formula (b) in which $R^{10}$ represents sec.butyl and R represents isobutyl.

Especially preferred compounds of formula I are:

$N^2$-[3(S)-[[N-(benzyloxycarbonyl)-L-asparaginyl]amino]-2(R or S)-hydroxy-4-phenylbutyl]—$N^1$-tert.butyl-L-prolinamide, $N^2$-[3(S)-[[N-(benzyloxycarbonyl)-L-asparaginyl]amino]-2(R or S)-hydroxy-4-phenylbutyl]—$N^1$-isobutyl-L-prolinamide, $N^2$-[3(S)-[[N-(benzyloxycarbonyl)-L-asparaginyl]amino]-2(R)-hydroxy-4-phenylbutyl]-$N^1$-tert.butyl-4(R)-thiazolidinecarboxamide, N-tert.butyl 1-[2(R)-hydroxy-4-phenyl-3(S)-[[N-(2-quinolylcarbonyl)-L-asparaginyl]amino]butyl]-2(S)-piperidinecarboxamide, 1-[3(S)-[[N-(benzyloxycarbonyl)-L-asparaginyl]amino]-2(R)-hydroxy-4-phenylbutyl]-N-tert.butyl-octahydro-(3aS,6aS)-cyclopenta[b]pyrrole-2(S)-carboxamide, 1-[3(S)-[[N-(benzyloxycarbonyl)-L-asparaginyl]amino]-2(R)-hydroxy-4-phenylbutyl]-N-tert.butyl-2(S)-piperidinecarboxamide, 2-[3(S)-[[N-(benzyloxycarbonyl)-L-asparaginyl]amino]-2(R)-hydroxy-4-phenylbutyl]-N-tert.butyl-1,2,3,4-tetrahydropyrido[3,4-b]indole-1-carboxamide, N-tert.butyl-3-[2(R)-hydroxy-3(S)-[[N-(2-naphthoyl)-L-asparaginyl]amino]-4-phenylbutyl]-4(R)-thiazolidinecarboxamide, $N^1$-tert.butyl-$N^2$-[2(R)-hydroxy-4-phenyl-3(S)-[[N-(2-quinolylcarbonyl)-L-asparaginyl]amino]-L-prolinamide $N^2$-oxide, 1-[3(S)-[[N-(benzyloxycarbonyl)-3-cyano-L-alanyl]amino-2(R)-hydroxy-4-phenylbutyl]-N-tert.butyl-2(S)-piperidinecarboxamide, 1-[3(S)-[[N-(benzyloxycarbonyl)-L-asparaginyl]amino]-2(R)-hydroxy-4-phenylbutyl]-4-(tert.butoxycarbonyl)-N-tert.butyl-2(R or S)-piperazinecarboxamide, 1-[3(S)-[[N-(benzyloxycarbonyl)-3-cyano-L-alanyl]amino]-2(R)-hydroxy,4-phenylbutyl]-4-(tert.butoxycarbonyl)-N-tert.butyl-2(R or S)-piperazinecarboxamide, $N^2$-[3(S)-[[N-(benzyloxycarbonyl)-L-asparaginyl]amino]-2(R)-hydroxy-4-phenylbutyl]-4(R)-(tert.butoxyformamido)-$N^1$-tert.butyl-L-prolinamide, 1-[3(S)-[[N-(3-benzyloxy-2-naphthoyl)-L-asparaginyl]amino]-2(R)-hydroxy-4-phenylbutyl]-N-tert.butyl-2(S)-piperidinecarboxamide, N-tert.butyl-1-[2(R)-hydroxy-4-phenyl-3(S)-[[N-(2-quinolylcarbonyl)-L-asparaginyl]amino]butyl]-2-piperidinecarboxamide 1-oxide, N-tert.butyl 1-[3(S)-[[N-(3-hydroxy-2-naphthoyl)-L-asparaginyl]amino]-2(R)-hydroxy-4-phenylbutyl]-2(S)-piperidinecarboxamide, trans-2-[3(S)-[[N-(benzyloxycarbonyl)-L-asparaginyl]amino]-2(R)-hydroxy, 4-phenylbutyl]-N-tert.butyl-decahydro-(4aR,8aS)-isoquinoline-3(S)-carboxamide, 4-(tert.butoxycarbonyl)-N-tert.butyl-1-[2(R)-hydroxy-4-phenyl-3(S)-[[N-(2-quinolylcarbonyl)-L-asparaginyl]amino]butyl]-2(R or S)-piperazinecarboxamide, N-tert.butyl-1-[2(R)-hydroxy-3(S)-[[N-(1-hydroxy-2-naphthoyl)-L-asparaginyl]amino]-4-phenylbutyl]-2(S)-piperidinecarboxamide, trans-N-tert.butyl-decahydro-2-[2(R)-hydroxy-4-phenyl-3(S)-[[N-(2-quinolylcarbonyl)-L-asparaginyl]amino]butyl]-(4aR,8aS)-isoquinoline-3(S)-carboxamide and N-tert.butyl-1-[2(R)-hydroxy-4-phenyl-3(S)-[[N-(2-quinolylcarbonyl)-L-cysteinyl]amino]butyl]-2(S)-piperidinecarboxamide.

The most preferred compounds of formula I are:

N-tert.Butyl-1-[2(R)-hydroxy-3(S)-[[N-(2-naphthoyl)-L-asparaginyl]amino]-4-phenylbutyl]-2(S)-piperidinecarboxamide, N-tert.butyl-octahydro-1-[2(R)-hydroxy-4-phenyl-3(S)-[[N-(2-quinolylcarbonyl)-L-asparaginyl]amino]butyl]-(3aS,6aS)-cyclopenta[b]pyrrole-2(S)-carboxamide and N-tert.butyl-1,2,3,4-tetrahydro-2-[2(R)-hydroxy-4-phenyl-3(S)-[[N-(2-quinolylcarbonyl)-L-asparaginyl]amino]butyl]pyrido[3,4-b]indole-1(R or S)-carboxamide.

According to the process provided by the present invention, the compounds of formula I hereinbefore and their pharmaceutically acceptable acid addition salts are manufactured by (a) for the manufacture of a compound of formula I in which n stands for zero, reacting a compound of the general formula

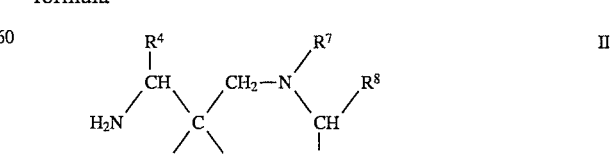

wherein $R^4$, $R^5$, $R^6$, $R^7$, $R^8$ and $R^9$ have the significance given earlier, with an acid of the general formula

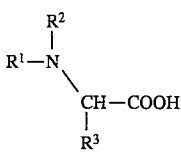

wherein $R^1$, $R^2$ and $R^3$ have the significance given earlier, or a reactive derivative thereof, or (b) for the manufacture of a compound of formula I in which n stands for zero, $R^5$ represents hydrogen and $R^6$ represents hydroxy, reducing a compound of formula I in which n stands for zero and $R^5$ and $R^6$ together represent oxo, or (c) for the manufacture of a compound of formula I in which n stands for zero and $R^1$ represents alkanoyl, cycloalkylcarbonyl, aralkanoyl, aroyl, heterocyclylcarbonyl, alkylsulphonyl, arylsulphonyl, cinnamoyl or α-aralkoxycarbonylaminoalkanoyl and $R^2$ represents hydrogen or $R^1$ and $R^2$ together with the nitrogen atom to which they are attached represent a cyclic imide group of formula (a) hereinbefore, reacting a compound of the general formula

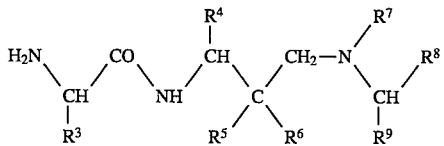

wherein $R^3$, $R^4$, $R^5$, $R^6$, $R^7$, $R^8$ and $R^9$ have the significance given earlier,
with an agent yielding an alkanoyl, cycloalkylcarbonyl, aralkanoyl, aroyl, heterocyclylcarbonyl, alkylsulphonyl, arylsulphonyl, cinnamoyl or α-aralkoxycarbonylaminoalkanoyl group or with an agent forming a cyclic imide group of formula (a) hereinbefore, or (d) for the manufacture of a compound of formula I in which n stands for zero and $R^1$ represents monoaralkylcarbamoyl and $R^2$ represents hydrogen, reacting a compound of formula IV hereinbefore with a compound of the general formula $$R^{1'}—N=C=O \qquad V$$

wherein $R^{1'}$ represents aralkyl, or (e) for the manufacture of a compound of formula I in which $R^3$ represents alkylsulphinylalkyl and n stands for zero, oxidizing a compound of formula I in which $R^3$ represents alkylthioalkyl and n stands for zero, or (f) for the manufacture of a compound of formula I in which n stands for 1, oxidizing a compound of formula I in which n stands for zero, or (g) for the manufacture of a compound of formula I in which n stands for 1 and $R^1$ represents an aromatic N-heterocyclylcarbonyl N-oxide group and $R^2$ represents hydrogen, oxidizing a compound of formula I in which n stands for 1 and $R^1$ represents an aromatic N-heterocyclylcarbonyl group and $R^2$ represents hydrogen, or (h) for the manufacture of a compound of formula I in which n strands for 1 and $R^3$ represents alkylsulphonylalkyl, oxidizing a compound of formula I in which n stands for 1 and $R^3$ represents alkylsulphinylalkyl, or (i) for the manufacture of a compound of formula I in which $R^1$ represents carboxy-substituted aroyl, hydroxy-substituted aroyl or hydrocinnamoyl and $R^2$ represents hydrogen, catalytically hydrogenating a compound of formula I in which $R^1$ represents benzyloxycarbonyl-substituted aroyl, benzyloxy-substituted aroyl or cinnamoyl and $R^2$ represents hydrogen, or (j) for the manufacture of a compound of formula I in which $R^3$ represents imidazol-4-yl and/or $R^4$ represents hydroxy-substituted aryl or hydroxy-substituted aralkyl and/or $R^7$ and $R^8$ together represent a trimethylene or tetramethylene group in which one —$CH_2$— group is replaced by —NH—, treating a compound of formula I in which $R^3$ represents 1-(benzyloxycarbonyl)-imidazol-4-yl and/or $R^4$ represents tert.butoxy-substituted aryl or tert.butoxy-substituted aralkyl and/or $R^7$ and $R^8$ together represent a trimethylene or tetramethylene group in which one —$CH_2$— group is replaced by —N(tert.butoxycarbonyl)- with a strong acid, or (k) for the manufacture of a compound of formula I in which $R^7$ and $R^8$ together represent a trimethylene or tetramethylene group which is substituted by acylamino or in which one —$CH_2$— group is replaced by —N(acyl)-, acylating a compound of the general formula

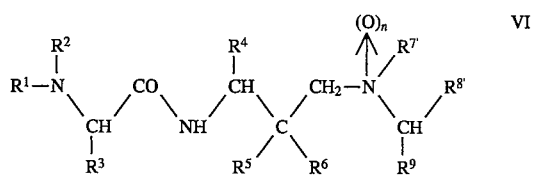

wherein n, $R^1$, $R^2$, $R^3$, $R^4$, $R^5$, $R^6$ and $R^9$ have the significance given earlier and $R^{7'}$ and $R^{8'}$ together represent a trimethylene or tetramethylene group which is substituted by amino or in which one —$CH_2$— group is replaced by —NH—, and/or (l) if desired, separating a mixture of diastereoisomeric racemates into the diastereoisomeric racemates or optically pure diastereoisomers, and/or (m) if desired, separating a mixture of diastereoisomers into the optically pure diastereoisomers, and/or (n) if desired, converting a compound of formula I obtained into a pharmaceutically acceptable acid addition salt.

The reaction of a compound of formula II with an acid of formula III in accordance with embodiment (a) of the process can be carried out in accordance with methods known per se in peptide chemistry. Thus, when an acid of formula III is used, the reaction is preferably carried out in the presence of a condensation agent such as hydroxybenzotriazole and dicyclohexylcarbodiimide. This reaction is conveniently carried out in an inert organic solvent such as an ether (e.g. diethyl ether, tetrahydrofuran etc) or dimethylformamide at a low temperature, suitably at about −10° C. to +5° C. and especially at about 0° C. Suitable reactive derivatives of acids of formula III which can be used are, for example, the corresponding acid halides (e.g. acid chlorides), acid anhydrides, mixed anhydrides, activated esters etc. When a reactive derivative is used, the reaction is conveniently carried out in an inert organic solvent such as a halogenated aliphatic hydrocarbon (e.g. dichloromethane etc) or an ether (e.g. diethyl ether, tetrahydrofuran etc) and, where appropriate, in the presence or an organic base (e.g. N-ethylmorpholine, diisopropylethylamine etc) at a low temperature, suitably at about −10° C. to +5° C. and especially at about 0° C.

The reduction of a compound of formula I in which $R^5$ and $R^6$ together represent oxo in accordance with embodiment (b) of the process can be carried out according to methods known per se for the reduction of a carbonyl group to a hydroxy group. Thus, for example, the reduction can be carried out using a complex metal hydride such as an alkali metal borohydride, especially sodium borohydride, in an appropriate organic solvent such as an alkanol (e.g. methanol, ethanol, propanol, isopropanol etc). Conveniently, the reduction is carried out at about room temperature.

In accordance with embodiment (c) of the process, suitable agents which yield an alkanoyl, cycloalkylcarbonyl, aralkanoyl, aroyl, heterocyclylcarbonyl, alkylsulphonyl, cinnamoyl or α-aralkoxycarbonylaminoalkanoyl group are the corresponding acids or reactive derivatives thereof such as the corresponding acid halides (e.g. acid chlorides), acid anhydrides, mixed anhydrides, activated esters etc and suitable agents which form a cyclic imide group of formula (a) hereinbefore are compounds of the formula HOOC—P—Q—COOAralkyl in which P and Q have the significance given earlier. The reaction of a compound of formula IV with the aforementioned agents is carried out in the same manner as that described earlier in connection with embodiment (a) of the process. In the reaction of a compound of formula IV with a compound of the formula HOOC—P—Q—COOAralkyl, the initially formed reaction product spontaneously loses a molecule of aralkanol (HO-Aralkyl) with the formation of the cyclic imide group.

The reaction of a compound of formula IV with a compound of formula V in accordance with embodiment (d) of the process can be carried out in a manner known per se. Thus, the reaction is conveniently carried out in an inert organic solvent such as a halogenated aliphatic hydrocarbon (e.g. dichloromethane etc) at a temperature between about 0° C. and room temperature, preferably at room temperature.

The oxidation in accordance with embodiments (e), (f), (g) and (h) of the process can be carried out according to known procedures. The oxidation is preferably carried out using an organic peracid such as peracetic acid, perbenzoic acid, a haloperbenzoic acid such as m-chloroperbenzoic acid, perphthalic acid or the like, although it can also be carried out using hydrogen peroxide. The oxidation is conveniently carried out in the presence of an organic solvent which is inert under the reaction conditions, for example an alkanol such as methanol, ethanol etc, a halogenated hydrocarbon such as methylene chloride etc, and the like. The oxidation can be carried out within a wide temperature range, for example a range between about −70° C. and about room temperature.

The catalytic hydrogenation in accordance with embodiment (i) of the process can be carried out in a known manner. Conveniently, the catalytic hydrogenation is carried out in the presence of a noble metal catalyst, preferably a palladium catalyst such as palladium-on-carbon, and in an inert organic solvent (e.g. an alkanol such as ethanol, isopropanol etc) at about room temperature and under atmospheric pressure. When a compound of formula I in which $R^1$ represents nitro-substituted cinnamoyl and $R^2$ represents hydrogen is catalytically hydrogenated according to this embodiment, then there is obtained a compound of formula I in which $R^1$ represents amino-substituted hydrocinnamoyl and $R^2$ represents hydrogen.

Embodiment (j) of the process can be carried out using a strong inorganic acid, for example a hydrohalic acid such as hydrogen chloride or hydrogen bromide, or a strong organic acid, for example a halogenated alkanecarboxylic acid such as trifluoroacetic acid and the like. This embodiment can be carried out according to known procedures; for example in the presence or absence of an inert organic solvent (e.g. an alkanecarboxylic acid ester such as ethyl acetate etc) and at a temperature between about 0° C. and about room temperature, preferably at about room temperature.

The acylation of a compound of formula VI in accordance with embodiment (k) of the process can be carried out according to methods known per se. Conveniently, the acylation is carried out using an acyl halide such as an acyl chloride or bromide in the presence of an inert organic solvent such as dimethylformamide etc and at a temperature between about 0° C. and room temperature. In place of an acid halide there can, of course, also be used a different reactive acid derivative such as an acid anhydride or the like.

The optional separations in accordance with embodiments (l) and (m) of the process can be effected according to conventional methods; for example, by column chromatography, thin-layer chromatography, high pressure liquid chromatography etc.

The conversion of a compound of formula I into a pharmaceutically acceptable acid addition salt in accordance with embodiment (n) of the process can be carried out by treating such a compound in a conventional manner with an inorganic acid, for example a hydrohalic acid such as hydrochloric acid or hydrobromic acid, sulphuric acid, nitric acid, phosphoric acid etc, or with an organic acid such as acetic acid, citric acid, maleic acid, fumaric acid, tartaric acid, methanesulphonic acid, p-toluenesulphonic acid etc.

The compounds of formula II which are used as starting materials in embodiment (a) of the process are novel and also form an object of the present invention.

The compounds of formula II can be prepared, for example, by reacting a compound of the general formula

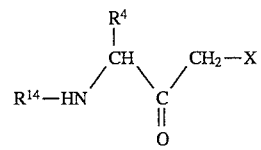

VII wherein $R^4$ has the significance given earlier, $R^{14}$ represents an amino-protecting group (e.g. tert.butoxycarbonyl or benzyloxycarbonyl) and X represents a chlorine or bromine atom, with a compound of the general formula

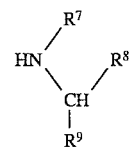

VIII wherein $R^7$, $R^8$ and $R^9$ have the significance given earlier, and either cleaving off the group $R^{14}$ from the resulting compound of the general formula

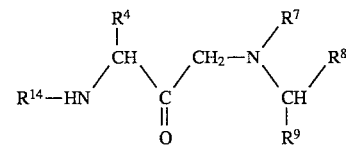

IX wherein $R^4$, $R^7$, $R^8$, $R^9$ and $R^{14}$ have the significance given earlier,
to give a compound of formula II in which $R^5$ and $R^6$ together represent oxo or reducing the compound of formula IX and cleaving off the group $R^{14}$ from the resulting compound of the general formula

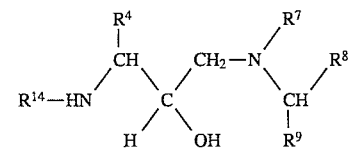

X wherein $R^4$, $R^7$, $R^8$, $R^9$ and $R^{14}$ have the significance given earlier,
to give a compound of formula II in which $R^5$ represents hydrogen and $R^6$ represents hydroxy.

The reaction of a compound of formula VII, preferably one in which $R^{14}$ represents benzyloxycarbonyl, with a compound of formula VIII can be carried out in a known manner; for example, in an inert organic solvent such as a halogenated aliphatic hydrocarbon (e.g. dichloromethane etc) and in the presence of a base (e.g. a trialkylamine such as triethylamine etc), conveniently at about room temperature.

The cleavage of the group $R^{14}$ from a compound of formula IX can also be carried out in a known manner: for example, using a strong inorganic acid such as a hydrohalic acid or a strong organic acid (e.g. trifluoroacetic acid etc), conveniently at about 0° C. to about room temperature. Alternatively, a hydrogenolytically-cleavable amino-protecting group $R^{14}$ can be cleaved off using hydrogen in the presence of a noble-metal catalyst (e.g. a palladium catalyst such as palladium-on-carbon) in an organic solvent or solvent mixture which is inert under the reaction conditions (e.g. an alkanol such as ethanol, isopropanol etc, an alkanecarboxylic acid ester such as ethyl acetate, etc) and conveniently at about room temperature.

The reduction of a compound of formula IX to give a compound of formula X can be carried out as described earlier in connection with the reduction of a compound of formula I in which n stands for zero and $R^5$ and $R^6$ together represent oxo in accordance with embodiment (b) of the process of the invention.

The cleavage of the group $R^{14}$ from a compound of formula X can be carried out in a manner analogous to that described earlier in connection with the cleavage of the group $R^{14}$ from a compound of formula IX.

A further method for the preparation of compounds of formula II in which $R^5$ represents hydrogen and $R^6$ represents hydroxy comprises firstly reacting a compound of the general formula

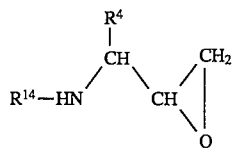

XI wherein $R^4$ and $R^{14}$ have the significance given earlier, with a compound of formula VIII hereinbefore, conveniently in an inert organic solvent such as an alkanol (e.g. methanol etc), dimethylformamide or the like and at an elevated temperature, conveniently at about 60° C. to about 120° C., and then cleaving off the group $R^{14}$ in the reaction product (a compound of formula X hereinbefore) as described earlier.

The compounds of formula IV which are used as starting materials in embodiments (c) and (d) of the process are novel and form a further object of the present invention.

The compounds of formula IV can be prepared, for example, by cleaving off the benzyloxycarbonyl or tert.butoxycarbonyl group $R^1$ from a compound of formula I in which n stands for zero, $R^1$ represents benzyloxycarbonyl or tert.butoxycarbonyl and $R^2$ represents hydrogen. This cleavage is carried out in a manner analogous to that described earlier in connection with the cleavage of the group $R^{14}$ from a compound of formula IX.

The compounds of formula VI wherein $R^{7'}$ and $R^{8'}$ together represent a trimethylene or tetramethylene group in which one —$CH_2$— group is replaced by —NH—, which are used as starting materials in embodiment (k) of the process, are a sub-group of compounds of formula I. The compounds of formula VI wherein $R^{7'}$ and $R^{8'}$ together represent a trimethylene or tetramethylene group which is substituted by amino, which are also used as starting materials in embodiment (k) of the process, are novel and also form an object of the present invention. They can be prepared, for example, by cleaving off the alkoxycarbonyl group from a compound of formula I in which $R^7$ and $R^8$ together represent a trimethylene or tetramethylene group which is substituted by alkoxycarbonylamino. The cleavage can be carried out according to conventional procedures; for example, by treatment with an acid such as a hydrogen halide (e.g. hydrogen chloride) in an inert organic solvent (e.g. an alkanecarboxylic acid ester such as ethyl acetate) etc).

The starting materials of formula III and their reactive derivatives, the starting materials of formula V as well as the compounds of formulae VII, VIII and XI hereinbefore, insofar as they are not known compounds or analogues of known compounds, can be prepared in a similar manner to the known compounds or as described in the Examples hereinafter or in analogy thereto. Moreover, the agents used in embodiment (c) of the process are generally known compounds.

As mentioned earlier, the compounds of formula I and their pharmaceutically acceptable acid addition salts inhibit proteases of vital origin and are useful in the treatment or prophylaxis of viral infections, particularly of infections caused by HIV and other retroid viruses.

The in vitro inhibition of HIV protease by the compounds provided by the present invention can be demonstrated by means of the following test:

HIV protease was expressed in *E. coli* and partially purified from soluble extracts of the bacterium by ammonium sulphate fractionation (0–30%), Protease activity was assayed using the protected hexapeptide succinyl-Ser-Leu-Asn-Tyr-Pro-Ile isobutylamide as the substrate. Cleavage of the substrate was quantified by measuring the production of H-Pro-Ile isobutylamide by the spectrophotometric assay of N-terminal proline, 1.25 mM of substrate were dissolved in 125 mM of citrate buffer (pH 5.5) containing 0.125 mg/ml of Tween 20, 10 µl of a solution of various concentrations of the test compound (dissolved in methanol or dimethyl sulphoxide and diluted with water containing 0.1% Tween 20) and 10 µl of protease were added to 80 µl of the above buffered substrate. Digestion was carried out at 37° C. for a fixed period of time and was terminated by the addition of 1 ml of colour reagent [30 µg/ml of isatin and 1.5 mg/ml of 2-(4-chlorobenzoyl)benzoic acid in 10% acetone in ethanol (vol./vol.)]. The solution was heated in a water bath and then the pigmented residues were re-dissolved in 1 ml of 1% pyrogallol in 33% water in acetone (wt./vol./vol.). The optical density of the solution was measured spectrophotometrically at 599 nm. The formation of H-Pro-Ile isobutylamide in the presence of the test compound was compared with controls and the concentration of test compound required to give 50% inhibition ($I_{50}$) was determined by means of a graph plotted from the various concentrations of test compound used.

The results obtained in the foregoing test using representative compounds of formula I as the test compound are compiled in the following Table.

TABLE

| Compound | $I_{50}$ (µM) |
|---|---|
| A | 0.87 |
| B | 0.15 |
| C | 0.3 |
| D | 0.13 |
| E | 0.75 |
| F | 0.75 |

TABLE-continued

| Compound | $I_{50}$ (μM) |
| --- | --- |
| G | 0.08 |
| H | 0.01 |
| I | 0.085 |

Compound A: N-[N-[[N-(Benzyloxycarbonyl)-L-asparaginyl]-L-phenylalanyl]methyl]-L-proline tert.butyl ester.

Compound B: N-[3(S)-[[N-(Benzyloxycarbonyl)-L-asparaginyl]-amino]-2(R)-hydroxy-4-phenylbutyl]-L-proline tert.butyl ester.

Compound C: N-[3(S)-[[N-(Benzyloxycarbonyl)-L-asparaginyl]-amino]-2(S)-hydroxy-4-phenylbutyl]-L-proline tert.butyl ester.

Compound D: $N^2$-[N-[3(S)-[[N-(Benzyloxycarbonyl)-L-asparaginyl]amino]-2(R and S)-hydroxy-4-phenylbutyl]-L-prolyl]-$N^1$-isobutyl-L-isoleucinamide (isomer 1; Example 13).

Compound E: $N^2$-[N-[3(S)-[[N-[N-(Benzyloxycarbonyl)-L-leucyl]-L-asparaginyl]amino]-2(R and S)-hydroxy-4-phenylbutyl]-L-prolyl]-$N^1$-isobutyl-L-isoleucinamide (isomer 1: Example 14).

Compound F: $N^2$-[3(S)-[[N-(Benzyloxycarbonyl)-L-asparaginyl]-amino]-2(R and S)-hydroxy-4-phenylbutyl]-$N^1$-isopentyl-L-prolinamide (isomer 2; Example 17).

Compound G: $N^2$-[3(S)-[[N-(Benzyloxycarbonyl)-L-asparaginyl]amino]-2(R or S)-hydroxy-4-phenylbutyl]-$N^1$-isobutyl-L-prolinamide (isomer 2; Example 21).

Compound H: N-[2(R)-Hydroxy-3(S)-[[N-(2-naphthoyl)-L-asparaginyl]amino]-4-phenylbutyl]-L-proline tert.butyl ester.

Compound I: 2-[3(S)-[[N-(Benzyloxycarbonyl)-L-asparaginyl]-amino]-2(R)-hydroxy-4-phenyl-butyl]-N-tert.butyl-1,2,3,4-tetrahydro-3(R,S)-isoquinolinecarboxamide.

The compounds of formula I and their pharmaceutically acceptable acid addition salts can be used as medicaments (e.g. in the form of pharmaceutical preparations). The pharmaceutical preparations can be administered enterally such as orally (e.g. in the form of tablets, coated tablets, dragees, hard and soft gelatine capsules, solutions, emulsions or suspensions), nasally (e.g. in the form of nasal sprays) or rectally (e.g. in the form of suppositories). However, the administration can also be effected parenterally such as intramuscularly or intravenously (e.g. in the form of injection solutions).

For the manufacture of tablets, coated tablets, dragees and hard gelatine capsules the compounds of formula I and their pharmaceutically acceptable acid addition salts can be processed with pharmaceutically inert, inorganic or organic excipients. Lactose, maize starch or derivatives thereof, talc, stearic acid or its salts etc can be use, for example, as such excipients for tablets, dragees and hard gelatine capsules.

Suitable excipients for soft gelatine capsules are, for example, vegetable oils, waxes, fats, semi-solid and liquid polyols etc.

Suitable excipients for the manufacture of solutions and syrups are, for example, water, polyols, saccharose, invert sugar, glucose etc.

Suitable excipients for injection solutions are, for example, water, alcohols, polyols, glycerol, vegetable oils etc.

Suitable excipients for suppositories are, for example, natural or hardened oils, waxes, fats, semi-liquid or liquid polyols etc.

Moreover, the pharmaceutical preparations can contain preserving agents, solubilizers, viscosity-increasing substances, stabilizing agents, wetting agents, emulsifying agents, sweetening agents, colouring agents, flavouring agents, salts for varying the osmotic pressure, buffers, coating agents or antioxidants. They can also contain still other therapeutically valuable substances.

In accordance with the invention the compounds of formula I and their pharmaceutically acceptable acid addition salts can be used in the treatment or prophylaxis of vital infections, particularly of retrovital infections. The dosage can vary within wide limits and will, of course, be fitted to the individual requirements in each particular case. In general, in the case of oral administration there should suffice a daily dosage of about 3 mg to about 3 g, preferably about 10 mg to about 1 g (e.g. approximately 300 mg per person), divided in preferably 1–3 unit doses, which can, for example, be of the same amount. It will, however, be appreciated that the upper limit given above can be exceeded when this is found to be indicated.

The following Examples illustrate the present invention. The solvent systems referred to in these Examples are as follows:

System A: 5% methanol in chloroform
System B: 10% methanol in chloroform
System C: chloroform:methanol:acetic acid:water (120:15:3:2)
System D: chloroform:methanol:acetic acid:water (90:15:3:2)
System E: chloroform:methanol:acetic acid:water (60:18:2:3)
System F: chloroform:methanol:acetic acid:water (240:24:3:2)
System G: dichloromethane:methanol:acetic acid:water (120:15:3:2)
System H: diethyl ether:n-hexane:methanol (47.5:47.5:5)
System I: dichloromethane:methanol:acetic acid:water (60:18:2:3)
System J: dichloromethane:methanol:acetic acid:water (120:15:2:3).

EXAMPLE 1

0.5 g (1.07 mmol) of N-[[N-(benzyloxycarbonyl)-L-phenylalanyl]methyl]-L-proline tert.butyl ester was dissolved in 50 ml of isopropanol and 5 ml of ethyl acetate and hydrogenated for 5 hours in the presence of 0.406 g (2.14 mmol) of toluene-4-sulphonic acid and 50 mg of 5% palladium-on-carbon. The catalyst was removed by filtration and the filtrate was evaporated. The residue was taken up in 5 ml of dichloromethane and 5 ml of dimethylformamide and cooled in an ice/salt bath. 0.285 g (1.07 mmol) of N-(benzyloxycarbonyl)-L-asparagine in 25 ml of dimethylformamide was added, followed by 0.145 g (1.07 mmol) of hydroxybenzotriazole, 0.221 g (1.07 mmol) of dicyclohexylcarbodiimide and 0.246 g (2.14 mmol) of N-ethylmorpholine. The mixture was left to stir overnight, the separated dicyclohexylurea was removed by filtration and the filtrate was evaporated to dryness in a vacuum. The resulting dark brown gum was partitioned between ethyl acetate and water. The organic phase was washed in sequence with 5% sodium bicarbonate solution and saturated sodium chloride solution and then dried over sodium sulphate. The solvent was removed by evaporation and the solid was chromatographed on silica gel using 5% isopropanol in ethyl acetate for the elution. There was obtained 0.125 g of N-[N-[[N-(benzyloxycarbonyl)-L-asparaginyl]-L-phenylalanyl]methyl]-L-proline tert.butyl ester as a pale yellow solid.

Analysis for: $C_{31}H_{40}N_4O_7$ [580.69]. Calculated: C, 64.12; H, 6.94; N, 9.65% Found: C, 63.18; H, 6.79; N, 9.8%; ash 1.2% Ash-free: C, 63.91; H, 6.87; N, 9.92%.

The N-[[N-(benzyloxycarbonyl)-L-phenylalanyl]methyl]-L-proline tert.butyl ester used as the starting material was prepared by stirring 0.77 g of [N-(benzyloxycarbonyl)-L-phenylalanyl]methyl bromide with 0.35 g of L-proline tert.butyl ester and 0.203 g of triethylamine in 15 ml of dichloromethane at room temperature overnight. The solvent was removed by evaporation and the crude product was chromatographed on silica gel using chloroform for the elution to give 0.65 g of N-[[N-(benzyloxycarbonyl)-L-phenylalanyl]methyl]-L-proline tert.butyl ester as a solid of melting point 98°–99° C.

EXAMPLE 2

1.5 g (3.22 mmol) of N-[[N-(benzyloxycarbonyl)-L-phenylalanyl]methyl]-L-proline tert.butyl ester were hydrogenated in 10 ml of ethyl acetate and 5 ml of isopropanol in the presence of 0.15 g of 5% palladium-on-carbon and 1.223 g (6.44 mmol) of toluene-4-sulphonic acid and the product was coupled with 1.24 g (3.27 mmol) of N-[N-(benzyloxycarbonyl)-L-leucyl]-L-asparagine in the presence of 0.442 g (3.27 mmol) of hydroxybenzotriazole, 0.675 g (3.27 mmol) of dicyclohexylcarbodiimide and 0.753 g (6.55 mmol) of N-ethylmorpholine in a an analogous manner to that described in Example 1. After working-up there was obtained 0.34 g of a solid which was chromatographed on silica gel using 5% isopropanol in dichloromethane for the elution. There were obtained 310 mg of N-[[N-[N-[N-(benzyloxycarbonyl)-L-leucyl]-L-asparaginyl]-L-phenylalanyl]methyl]-L-proline tert.butyl ester; MS: m/e 694 $[M+H]^+$.

The N-[N-(benzyloxycarbonyl)-L-leucyl]-L-asparagine used as the starting material was prepared as follows:

4.5 g (12.4 mmol) of N-(benzyloxycarbonyl)-L-leucine succinimide ester were dissolved in 40 ml of dimethylformamide and the solution was cooled in an ice/salt bath. A solution of 1.64 g (12.4 mmol) of L-asparagine in 3.1 ml (12.4 mmol) of 4M sodium hydroxide solution were added and subsequently 2 g (24.8 mmol) of sodium bicarbonate were added. The mixture was stirred at room temperature for 18 hours. The solvent was removed by evaporation and the residue was taken up in 100 ml of water. The pH was adjusted to about 9.5 with 2M sodium hydroxide solution and the mixture was extracted twice with 25 ml of diethyl ether each time. The pH of the aqueous solution was adjusted to 2.5 with 3M hydrochloric acid. The solid crystalline product which separated from the solution was filtered off, washed with diethyl ether and dried. There were obtained 3.5 g of N-[N-(benzyloxycarbonyl)-L-leucyl]-L-asparagine.

Analysis for: $C_{18}H_{25}N_3O_6$ (379.42). Calculated: C, 56.98; H, 6.64; N, 11.07% Found: C, 56.76; H, 6.62; N, 11.05%.

EXAMPLE 3

0.71 g (1.52 mmol) of N-[[N-(benzyloxycarbonyl)-L-phenylalanyl]methyl]-L-proline tert.butyl ester was hydrogenated in the presence of 0.58 g (3.05 mmol) of toluene-4-sulphonic acid over 5% palladium-on-carbon and the product was coupled with 0.35 g (1.52 mmol) of N-(4-methylvaleryl)-L-asparagine in an analogous manner to that described in Example 1. The crude product was purified by chromatography on silica gel using isopropanol in ethyl acetate (5%–8% gradient) for the elution. There was obtained 0.23 g of N-[[N-[N-(4-methylvaleryl)-L-asparaginyl]-L-phenylalanyl]methyl]-L-proline tert.butyl ester as a solid; MS: m/e 545 $[M+H]^+$.

The N-(4-methylvaleryl)-L-asparagine used as the starting material was prepared as follows:

5.35 g (25 mmol) of 4-methylvaleric acid succinimide ester were dissolved in 40 ml of dimethylformamide and the solution was added to a solution, cooled in ice, of 3.3 g (25 mmol) of L-asparagine in 6.25 ml (25 mmol) of 4M sodium hydroxide solution and 5 ml of dimethylformamide. 5.5 g (65 mmol) of sodium bicarbonate were added and the mixture was stirred at room temperature for 18 hours. The solvent was removed by evaporation and the residue was taken up in 100 ml of water. The pH was adjusted to 3 with 4M hydrochloric acid. The solvent was then removed by evaporation and the residue was taken up in methanol. Insoluble material was removed by filtration and the solvent was removed by evaporation. The crude product was chromatographed on silica gel using System D for the elution. There were obtained 900 mg of N-(4-methylvaleryl)-L-asparagine as a solid: Rf (System D): 0.25.

EXAMPLE 4

In an analogous manner to that described in Example 1, but using N-(tert.butoxycarbonyl)-L-asparagine in place of N-(benzyloxycarbonyl)-L-asparagine there was obtained N-[N-[[N-(tert.butoxycarbonyl)-L-asparaginyl]-L-phenylalanyl]methyl]-L-proline tert.butyl ester in the form of a solid; MS: m/e 546 $[M]^+$.

EXAMPLE 5

1.3 g (2.79 mmol) of N-[[N-(benzyloxycarbonyl)-L-phenylalanyl]methyl]-L-proline tert.butyl ester was hydrogenated in a mixture of 10 ml of ethyl acetate and 10 ml of isopropyl alcohol in the presence of 0.39 g of 5% palladium-on-carbon and 1.06 g (5.58 mmol) of toluene-4-sulphonic acid and the product was coupled with 0.62 g (2.78 mmol) of N-(benzyloxycarbonyl)-L-alanine in the presence of 0.572 g (2.78 mmol) of dicyclohexylcarbodiimide, 0.375 g (2.78 mmol) of hydroxybenzotriazole and 0.64 g (5.57 mmol) of N-ethylmorpholine in a manner analogous to that described in Example 1. After working-up and chromatography on silica gel using 3% isopropanol in dichloromethane for the elution there was obtained 0.55 g of N-[[N-[N-(benzyloxycarbonyl)-L-alanyl]-L-phenylalanyl]methyl]-L-proline tert.butyl ester as a solid: MS: m/e 538 $[M+H]^+$.

EXAMPLE 6

In a manner analogous to that described in Example 1, from N-[[N-(benzyloxycarbonyl)-L-phenylalanyl]methyl]-L-proline tert.butyl ester and N-(benzyloxycarbonyl)-L-glutamine there was obtained N-[[N-[N-(benzyloxycarbonyl)-L-glutaminyl]-L-phenylalanyl]methyl]-L-proline tert.butyl ester; MS: m/e 595 $[M+H]^+$.

EXAMPLE 7

0.45 g (0.77 mmol) of N-[N-[[N-(benzyloxycarbonyl)-L-asparaginyl]-L-phenylalanyl]methyl]-L-proline tert.butyl ester, prepared as described in Example 1, was dissolved in 10 ml of isopropanol and the solution was stirred at room temperature for 45 minutes in the presence of 0.075 g (1.98 mmol) of sodium borohydride. The solvent was removed by evaporation and the residue was taken up in 50 ml of ethyl acetate and washed in sequence with water and saturated sodium chloride solution. After drying over sodium sulphate and evaporation there was obtained 0.43 g of a solid which was chromatographed on silica gel using 2% methanol in dichloromethane for the elution. There were obtained 80 mg of N-[3(S)-[[N-(benzyloxycarbonyl)-L-asparaginyl]amino]-2(S)-hydroxy-4-phenylbutyl]-L-proline tert.butyl ester as a solid; Rf (System B): 0.38; MS: m/e 583 [M+H]⁺.

Further elution of the column with 5% methanol in dichloromethane yielded 70 mg of N-[3(S)-[[N-(benzyloxycarbonyl)-L-asparaginyl]amino]-2(R)-hydroxy-4-phenylbutyl]-L-proline tert.butyl ester as a solid: Rf (System B): 0.23; MS: m/e 583 [M+H]⁺.

EXAMPLE 8

0.3 g (0.45 mmol) of N-[[N-[N-[N-(benzyloxycarbonyl)-L-leucyl]-L-asparaginyl]-L-phenylalanyl]methyl]-L-proline tert.butyl ester, prepared as described in Example 2, in 10 ml of isopropanol was treated at room temperature with 40 mg (1.06 mmol) of sodium borohydride. After 1 hour the mixture was worked-up as described in Example 7. There was obtained 0.32 g of a solid which was chromatographed on silica gel using 3% methanol in dichloromethane for the elution. There were obtained 90 mg of N-[3(S)-[[N-[N-(benzyloxycarbonyl)-L-leucyl]-L-asparaginyl]amino]-2(R or S)-hydroxy-4-phenylbutyl]-L-proline tert.butyl ester (isomer 1) as a solid; Rf (System A): 0.26: MS: m/e 696 [M+H]⁺.

Further elution of the column with 5% methanol in dichloromethane yielded 70 mg of N-[3(S)-[[N-[N-(benzyloxycarbonyl)-L-leucyl]-L-asparaginyl]amino]-2(R or S)-hydroxy-4-phenylbutyl]-L-proline tert.butyl ester (isomer 2) as a solid; Rf (System A): 0.19; MS: m/e 696 [M+H]⁺.

EXAMPLE 9

0.18 g (0.33 mmol) of N-[[N-[N-(4-methylvaleryl)-L-asparaginyl]-L-phenylalanyl]methyl]-L-proline tert.butyl ester, prepared as described in Example 3, was reduced with 30 mg (0.80 mmol) of sodium borohydride in 10 ml of isopropanol as described in Example 7. The resulting two isomers of N-[2(R or S)-hydroxy-3(S)-[[N-(4-methylvaleryl)-L-asparaginyl]amino]-4-phenylbutyl]-L-proline tert.butyl ester were separated by chromatography on silica gel using methanol in chloroform (5%–8% gradient) for the elution. There were obtained 35 mg of isomer 1 in the form of a solid; Rf (System B): 0.2; MS: m/e 547 [M+H]⁺, and 27 mg of isomer 2 in the form of a solid; Rf (System B): 0.15; MS: m/e 547 [M+H]⁺.

EXAMPLE 10

0.6 g (1.1 mmol) of N-[N-[[N-(tert.butoxycarbonyl)-L-asparaginyl]-L-phenylalanyl]methyl]-L-proline tert.butyl ester, prepared as described in Example 4, was reduced with 0.1 g (2.65 mmol) of sodium borohydride in 10 ml of isopropanol as described in Example 7. The two isomers were separated by chromatography on silica gel using System C for the elution. There were obtained 115 mg of isomer 1 of N-[3(S)-[[N-(tert.butoxycarbonyl)-L-asparaginyl]amino]-2(R or S)-hydroxy-4-phenylbutyl]-L-proline tert.butyl ester in the form of a solid; Rf (System D): 0.23; MS: m/e 549 [M+H]⁺, and 100 mg of isomer 2 in the form of a solid; Rf (System D): 0.15; MS: m/e 549 [M+H]⁺.

EXAMPLE 11

0.45 g (0.84 mmol) of N-[[N-[N-(benzyloxycarbonyl)-L-alanyl]-L-phenylalanyl]methyl]-L-proline tert.butyl ester, prepared as described in Example 5, was reduced in 15 ml of isopropanol in the presence of 80 mg of sodium borohydride as described in Example 7. After working-up the two isomers were separated by chromatography on silica gel using System A for the elution. There were obtained 70 mg of isomer 1 of N-[3(S)-[[N-(benzyloxycarbonyl)-L-alanyl]amino]-2(R or S)-hydroxy-4-phenylbutyl]-L-proline tert.butyl ester in the form of a gum; Rf (System A): 0.38; MS: m/e 540 [M+H]⁺, and 50 mg of isomer 2 in the form of a gum; Rf (System A) 0.21; MS: m/e 540 [M+H]⁺.

EXAMPLE 12

0.55 g (0.93 mmol) of N-[[N-[N-(benzyloxycarbonyl)-L-glutaminyl]-L-phenylalanyl]methyl]-L-proline tert.butyl ester, prepared as described in Example 6, was reduced in 15 ml of isopropanol in the presence of 90 mg of sodium borohydride as described in Example 7. After working-up, the product was chromatographed on silica gel using 2% methanol in chloroform for the elution. There were obtained 60 mg of isomer 1 of N-[3(S)-[[N-(benzyloxycarbonyl)-L-glutaminyl]amino]-2(R or S)-hydroxy-4-phenylbutyl]-L-proline tert.butyl ester in the form of a solid; Rf (System B): 0.37; MS: m/e 597 [M+H]⁺, and 65 mg of isomer 2 in the form of a solid; Rf (System B): 0.25; MS: m/e 597 [M+H]⁺.

EXAMPLE 13

3 g (5.2 mmol) of $N^2$-[N-[3(S)-(benzyloxyformamido)-2(R and S)-hydroxy-4-phenylbutyl]-L-prolyl]-$N^1$-isobutyl-L-isoleucinamide were taken up in 25 ml of ethyl acetate and 10 ml of isopropanol and hydrogenated over 0.3 g of 5% palladium-on-carbon for 5 hours in the presence of 1.97 g (10.36 mmol) of toluene-4-sulphonic acid. The catalyst was filtered off and the filtrate was evaporated. The solid obtained was dried over phosphorus pentoxide under a high vacuum and coupled with 1.48 g (5.57 mmol) of N-(benzyloxycarbonyl)-L-asparagine in an analogous manner to that described in Example 1. 3.3 g of crude $N_2$-[N-[3(S)-[[N-(benzyloxycarbonyl)-L-asparginyl]amino]-2(R and S)-hydroxy-4-phenylbutyl]-L-prolyl]-$N^1$-isobutyl-L-isoleucinamide were obtained as a solid. The two isomers were separated by chromatography on silica gel using System F for the elution. There were obtained 90 mg of isomer 1 in the form of a solid; Rf (System F): 0.23; MS: m/e 695 [M+H]⁺, and 0.55 g of isomer 2 in the form of a solid; Rf (System F): 0.11; MS: m/e 695 [M+H]⁺.

The $N_2$-[N-[3(S)-(benzyloxyformamido)-2(R and S)-hydroxy-4-phenylbutyl]-L-prolyl]-$N^1$-isobutyl-L-isoleucinamide used as the starting material was prepared as follows:
(i) A solution of 20.0 g of N-(benzyloxycarbonyl)-L-isoleucine and 9.6 ml of N-ethylmorpholine in 400 ml of tetrahydrofuran was cooled to −20° C. and 9.8 ml of isobutyl chloroformate were added dropwise. The mixture was stirred for 5 minutes and then 5.52 g of isobutylamine were added dropwise. The mixture was stirred at −15° C. for 20 minutes and was then allowed to warm to room temperature. 20 ml of water were added and the solution was then evaporated to dryness. The residue was partitioned between 200 ml of water and 800 ml of ethyl acetate and the organic solution was washed with 200 ml of 5% citric acid solution, 200 ml of saturated sodium bicarbonate solution and 200 ml of water, dried over sodium sulphate and evaporated to dryness. The residue was triturated with diethyl ether to give 18.2 g of $N^2$-(benzyloxycarbonyl)-$N^1$-isobutyl-L-isoleucinamide which was used in the next step without further purification.

(ii) A solution of 18.0 g of the above product in 200 ml of ethanol was hydrogenated over 1.0 g of 10% palladium-on-carbon for 5 hours. The catalyst was removed by filtration and the filtrate was evaporated to give 9.8 g of $N^1$-isobutyl-L-isoleucinamide as a colourless oil which was used directly in the next step, (iii) A solution of 17.3 g of N-(benzyloxycarbonyl)-L-proline succinimide ester and 9.35 g of $N^1$-isobutyl-L-isoleucinamide in 120 ml of tetrahydrofuran was stirred at room temperature overnight. The solvent was removed by evaporation and the residue was partitioned between 200 ml of ethyl acetate and 250 ml of 5% citric acid solution. The organic solution was dried over anhydrous sodium sulphate and evaporated to dryness. The residue was recrystallized from a mixture of ethyl acetate and n-hexane to give 13.6 g of $N_2$-[N-(benzyloxycarbonyl)-L-propyl]-$N^1$-isobutyl-L-isoleucinamide as a white solid of melting point 87°–88° C.

(iv) A solution of 13.6 g of the above product in 500 ml of ethanol was hydrogenated over 10% palladium-on-carbon for 2 hours. The catalyst was removed by filtration and the filtrate was evaporated to give 9.10 g of $N_2$-L-prolyl-$N^1$-isobutyl-L-isoleucinamide as a colourless oil which was used without further purification.

(v) A solution of 8.86 g of [N-(benzyloxycarbonyl)-L-phenylalanyl]methyl bromide 6.71 g of $N^2$-L-prolyl-$N^1$-isobutyl-L-isoleucinamide and 2.60 g of triethylamine in 400 ml of dichloromethane was stirred at room temperature overnight. The solvent was removed by evaporation and the crude product was chromatographed on silica gel using ethyl acetate for the elution. The resulting product was triturated with a mixture of petroleum ether (b.p. 40°–60° C.) and ethyl acetate to give 8.70 g of $N^2$-[N-[[N-(benzyloxycarbonyl)-L-phenylalanyl]methyl]-L-prolyl]-$N^1$-isobutyl-L-isoleucinamide as an off-white solid of m.p. 80°–81° C.

(vi) A solution of 3.5 g of $N_2$-[[N-(benzyloxycarbonyl)-L-phenylalanyl]methyl]-L-prolyl]-$N^1$-isobutyl-L-isoleucinamide in 200 ml of ethanol was treated with 1.0 g of sodium borohydride in a manner analogous to that described in Example 7 to give 7.1 g of $N_2$-[N-[3(S)-(benzyloxyformamido)-2(R and S)-hydroxy-4-phenylbutyl]-L-prolyl]-$N^1$-isobutyl-L-isoleucinamide.

Analysis for: $C_{33}H_{48}N_4O_5$. 0.5 $H_2O$. Calculated: C, 67.21; H, 8.37; N, 9.50% Found: C, 67.29; H, 8.31; N, 9.47%.

EXAMPLE 14

0.78 g (1.34 mmol) of $N^2$-[N-[3(S)-(benzyloxyformamido)-2(R and S)-hydroxy-4-phenylbutyl]-L-prolyl]-$N^1$-isobutyl-L-isoleucinamide was hydrogenated and the product was coupled with 0.53 g (1.39 mmol) of N-[N-(benzyloxycarbonyl)-L-leucyl]-L-asparagine in an analogous manner to that described in Example 1. 1.1 g of crude $N^2$-[N-[3(S)-[[N-[N-(benzyloxycarbonyl)-L-leucyl]-L-asparaginyl]amino]-2(R and S)-hydroxy-4-phenylbutyl]-L-prolyl]-$N^1$-isobutyl-L-isoleucinamide were obtained as a solid. The two isomers were separated by chromatography on silica gel using System F for the elution. There were obtained 60 mg of isomer 1 in the form of a solid; Rf (System C): 0.34; MS: m/e 808 $[M]^+$, and 50 mg of isomer 2 in the form of a solid; Rf (System C) 0.24; MS: m/e 808 $[M]^+$.

EXAMPLE 15

0.275 g (0.473 mmol) of N-[3(S)-[[N-(benzyloxycarbonyl)-L-asparaginyl]amino]-2(R)-hydroxy-4-phenylbutyl]-L-proline tert.butyl ester was taken up in 10 ml of isopropanol and hydrogenated for 18 hours over 50 mg of 5% palladium-on-carbon in the presence of 0.18 g (0.94 mmol) of toluene-4-sulphonic acid. The catalyst was filtered off and the filtrate was evaporated. The resulting solid was dissolved in 10 ml of dichloromethane and the solution was cooled in an ice-bath. 50 mg (0.49 mmol) of acetic anhydride were added, followed by 0.10 g (0.99 mmol) of triethylamine and 0.2 ml of pyridine. The mixture was stirred at room temperature for 1 hour. The solvent was removed by evaporation and the residue was partitioned between ethyl acetate and water. The organic phase was washed with 5% sodium bicarbonate solution and with saturated sodium chloride solution and then dried over anhydrous sodium sulphate. The solvent was removed by evaporation to give 35 mg of N-[3(S)-[(N-acetyl-L-asparaginyl)amino]-2(R)-hydroxy-4-phenylbutyl]-L-proline tert.butyl ester; Rf (System E): 0.28; MS: m/e 491 $[M+H]^+$.

EXAMPLE 16

1 g (2.14 mmol) of N-[3(S)-(benzyloxyformamido)-2-(R and S)-hydroxy-4-phenylbutyl]-L-proline tert.butyl ester was taken up in 25 ml of methanol and hydrogenated over 250 mg of 5% palladium-on-carbon for 3 hours in the presence of 0.81 g (4.26 mmol) of toluene-4-sulphonic acid. The catalyst was filtered off and the filtrate was evaporated. The resulting solid was dried over phosphorus pentoxide under a high vacuum and then dissolved in 5 ml of tetrahydrofuran.

0.566 g (2.134 mmol) of N-(benzyloxycarbonyl)-L-leucine was taken up in 15 ml of tetrahydrofuran and cooled to −15° C. 0.245 g (2.134 mmol) of N-ethylmorpholine and 0.291 g (2.134mmol) of isobutyl chloroformate were added. After 5 minutes the tetrahydrofuran solution prepared as described in the previous paragraph was added, followed by 0.451 g (4.27 mmol) of N-ethylmorpholine. The mixture was stirred at room temperature for 10 hours, the solvent was then removed by evaporation and the residue was partitioned between ethyl acetate and water. The ethyl acetate solution was washed with saturated sodium bicarbonate solution and with saturated sodium chloride solution and then dried over anhydrous sodium sulphate. The solvent was removed under a vacuum to give 1.5 g of crude N-[3(S)-[[N-(benzyloxycarbonyl)-L-leucyl]amino]-2-(R and S)-hydroxy-4-phenylbutyl]-L-proline tert.butyl ester as an oil. The two isomers were separated by chromatography on silica gel using 50% n-hexane in ethyl acetate for the elution. There were obtained 180 mg of isomer 1 of N-[3(S)-[[N-(benzyloxycarbonyl)-L-leucyl]amino]-2(R or S)-hydroxy-4-phenylbutyl]-L-proline tert.butyl ester as a crystalline material; Rf (System A): 0.34; MS: m/e 582 $[M+H]^+$, and 70 mg of isomer 2 as a crystalline material; Rf (System A): 0.28; MS: m/e 582 $[M+H]^+$.

The N-[3(S)-(benzyloxyformamido)-2(R and S)-hydroxy-4-phenylbutyl]-L-proline tert.butyl ester used as the starting material was prepared as follows:

2 g (4.3 mmol) of N-[[N-(benzyloxycarbonyl)-L-phenylalanyl]methyl]-L-proline tert.butyl ester (prepared as described in Example 1) were dissolved in 25 ml of isopropanol, 25 ml of ethanol and 25 ml of methanol and the solution was stirred at room temperature for 4 hours in the presence of 0.4 g (10.7 mmol) of sodium borohydride. The solvent was removed by evaporation and the residue was partitioned between 50 ml of ethyl acetate and 25 ml of water. The organic phase was washed with saturated sodium chloride solution and dried over anhydrous sodium sulphate.

The solvent was removed by evaporation and there were obtained 2 g of N-[3(S)-(benzyloxyformamido)-2(R and S)-hydroxy-4-phenylbutyl]-L-proline tert.butyl ester as a clear gum: Rf (System C): 0.68 and 0.57.

EXAMPLE 17

1.5 g (3.12 mmol) of $N_2$-[3(S)-(benzyloxyformamido)-2(R and S)-hydroxy-4-phenylbutyl]-$N^1$-isopentyl-L-prolinamide were hydrogenated in 25 ml of methanol in the presence of 1.19 g (6.24 mmol) of toluene-4-sulphonic acid and 0.25 g of 5% palladium-on-carbon. After 3 hours the catalyst was filtered off and the filtrate was evaporated to give 2.1 g of a solid. This solid was dried over phosphorus pentoxide under a high vacuum and coupled with 0.8 g (3.12 mmol) of N-(benzyloxycarbonyl)-L-asparagine in a manner analogous to that described in Example 1. There were obtained 1.45 g of $N_2$-[3(S)-[[N-(benzyloxycarbonyl)-L-asparaginyl]amino]-2(R and S)-hydroxy-4-phenylbutyl]-$N^1$-isopentyl-L-prolinamide as a crude product which was chromatographed on silica gel using System C for the elution. There were obtained 60 mg of isomer 1 as a solid; Rf (System E): 0.58; MS: 596 [M+H]$^+$, and 0.25 g of isomer 2 as a solid, Rf (System E): 0.41; MS: m/e 596 [M+H]$^+$.

The $N^2$-[3(S)-(benzyloxyformamido)-2(R and S)-hydroxy-4-phenylbutyl]-$N^1$-isopentyl-L-prolinamide used as the starting material was prepared as follows:

(i) A solution of 15.0 g of N-(benzyloxycarbonyl)-L-proline succinimide ester and 4.15 g of isopentylamine in 100 ml of tetrahydrofuran was stirred at room temperature overnight. The solvent was removed by evaporation and the residue was taken up in 250 ml of ethyl acetate. The solution was washed with 250 ml of 5% citric acid solution, two 250 ml portions of saturated sodium bicarbonate solution and 150 ml of saturated sodium chloride solution, dried over anhydrous sodium sulphate and evaporated to dryness. The residue was recrystallized from a mixture of ethyl acetate and n-hexane to give 11.1 g of $N^2$-(benzyloxycarbonyl)-$N^1$-isopentyl-L-prolinamide as a white solid of melting point 110°–112° C.

(ii) A solution of 5.73 g of $N_2$-(benzyloxycarbonyl)-$N^1$-isopentyl-L-prolinamide in 600 ml of ethanol was hydrogenated over 0.8 g of 10% palladium-on-carbon catalyst for 3.75 hours. The catalyst was removed by filtration and the filtrate was evaporated to give 3.4 g of $N^1$-isopentyl-L-prolinamide as an oil which was used without further purification.

(iii) A solution of 3.4 g of $N^1$-isopentyl-L-prolinamide, 6.76 g of [N-[benzyloxycarbonyl)-L-phenylalanyl]methyl bromide and 2.0 g of triethylamine in 360 ml of dichloromethane was stirred at room temperature overnight. The crude product was isolated in a manner analogous to that described in Example 1 and was recrystallized from a mixture of ethyl acetate and n-hexane to give 3.3 g of $N_2$-[[N-(benzyloxycarbonyl)-L-phenylalanyl]methyl]-$N^1$-isopentyl-L-prolinamide as a white solid of melting point 82°–84° C.

(iv) A solution of 0.96 g of $N_2$-[[N-(benzyloxycarbonyl)-L-phenylalanyl]methyl]-$N^1$-isopentyl-L-prolinamide in 40 ml of ethanol was treated with 0.17 g of sodium borohydride in a manner analogous to that described in Example 2. The crude product was recrystallized from a mixture of diethyl ether and n-hexane to give 0.65 g of $N^2$-[3(S)-(benzyloxyformamido)-2(R and S)-hydroxy-4-phenylbutyl]-$N^1$-isopentyl-L-prolinamide as a white solid of melting point 73°–82° C.

EXAMPLE 18

0.58 g (1.24 mmol) of $N_2$-[3(S)-(benzyloxyformamido)-2(R or S)-hydroxy-4-phenylbutyl]-$N^1$-tert.butyl-L-prolinamide was dissolved in 25 ml of methanol and hydrogenated for 5 hours at room temperature in the presence of 0.472 g (2.48 mmol) of toluene-4-sulphonic acid and 0.1 g of 5% palladium-on-carbon. The catalyst was filtered off and the filtrate was evaporated. There was obtained 0.82 g of a solid which was dried over phosphorus pentoxide under a high vacuum and coupled with 0.322 g (1.21 mmol) of N-(benzyloxycarbonyl)-L-asparagine in dimethylformamide in a manner analogous to that described in Example 1. After working-up in a manner analogous to that described in Example 10 there was obtained 0.6 g of crude product which was chromatographed on silica gel using System C for the elution. There were obtained 225 mg of $N_2$-[3(S)-[[N-(benzyloxycarbonyl)-L-asparaginyl]amino]-2(R or S)-hydroxy-4-phenylbutyl]-$N^1$-tert.butyl-L-prolinamide as a solid; MS: m/e 582 [M+H]$^+$.

The $N^2$-[3(S)-(benzyloxyformamido)-2(R or S)-hydroxy-4-phenylbutyl]-$N^1$-tert.butyl-L-prolinamide used as the starting material was prepared as follows:

(i) 5.2 g (15 mmol) of N-(benzyloxycarbonyl)-L-proline succinimide ester and 1.63 g (22.3 mmol) of tert.butylamine were taken up in 50 ml of dichloromethane and the mixture was stirred at −8° C. for 1 hour and then at room temperature for 18 hours. The solution was then washed with 5% citric acid solution, saturated sodium bicarbonate solution and saturated sodium chloride solution and dried over anhydrous sodium sulphate. After evaporation the solid was crystallized from ethyl acetate/n-hexane to give 3 g of $N^2$-(benzyloxycarbonyl)-$N^1$-tert.butyl-L-prolinamide; MS: m/e 305 [M+H]$^+$.

(ii) 2.5 g (8.22 mmol) of $N_2$-(benzyloxycarbonyl)-$N^1$-tert.butyl-L-prolinamide in 25 ml of methanol were hydrogenated for 5 hours over 0.5 g of 5% palladium-on-carbon. The catalyst was removed by filtration and the solvent was removed by evaporation to give 1.4 g of an oil which crystallized upon standing in a refrigerator for several hours. 0.35 g (2.05 mmol) of this solid was added to a solution of 0.77 g (2.05 mmol) of [N-(benzyloxycarbonyl)-L-phenylalanyl]methyl bromide in 15 ml of dichloromethane and subsequently 0.207 g (2.05 mmol) of triethylamine were added. The mixture was stirred at room temperature for 2 hours. The solvent was removed by evaporation and the residue was taken up in 25 ml of ethyl acetate. The solid was filtered off and discarded. The mother liquor was washed with water, saturated sodium bicarbonate solution and saturated sodium chloride solution and then dried over anhydrous sodium sulphate. After evaporation and crystallization from ether/n-hexane there was obtained 0.65 g of $N_2$-[[N-(benzyloxycarbonyl)-L-phenylalanyl]methyl]-$N^1$-tert.butyl-L-prolinamide in the form of a solid; MS: m/e 466 [M+H]$^+$.

(iii) 1.25 g (2.7 mmol) of $N_2$-[[N-(benzyloxycarbonyl)-L-phenylalanyl]methyl]-$N^1$-tert.butyl-L-prolinamide was taken up in 25 ml of isopropanol and stirred for 4 hours at room temperature in the presence of 0.255 g (6.7 mmol) of sodium borohydride. The solvent was removed by evaporation and the residue was partitioned between ethyl acetate and water. The organic layer was washed with saturated sodium chloride solution, dried over anhydrous sodium sulphate and evaporated. There were obtained 1.2 g of $N^2$-[3(S)-(benzyloxyformamido)-2(R and S)-hydroxy-4-phenylbutyl]-N -tert.butyl-L-prolinamide which was chromatographed on silica gel using System F for the elution. There were obtained 15 mg of isomer 1 as a gum; Rf (System F): 0.38; MS: m/e 468 [M+H]$^+$, and 0.225 g of isomer 2 as a gum; Rf (System F): 0.27; MS: m/e 468 [M+H]$^+$.

EXAMPLE 19

A solution of 474 mg of N-[3(S)-(benzyloxyformamido)-4-cyclohexyl-2(R or S)-hydroxybutyl]-L-proline tert.butyl ester in 100 ml of ethanol was hydrogenated over 50 mg of 10% palladium-on-carbon catalyst for 3 hours. The catalyst was removed by filtration and the filtrate was evaporated to give 380 mg of an oil. This was coupled with 285 mg of N-(benzyloxycarbonyl)-L-asparagine in a manner analogous to that described in Example 1. The crude product was chromatographed on silica gel using 7% methanol in dichloromethane for the elution to give 30 mg of N-[3(S)-[[N-(benzyloxycarbonyl)-L-asparaginyl]amino]-4-cyclohexyl-2(R or S)-hydroxybutyl]-L-proline tert.butyl ester as a white solid of melting point 135°–136° C. (isomer 1).

Similarly, 474 mg of the other isomer of N-[3(S)-(benzyloxyformamido)-4-cyclohexyl-2(R or S)-hydroxybutyl]-L-proline tert.butyl ester were hydrogenated and coupled with 285 mg of N-(benzyloxycarbonyl)-L-asparagine to give 90 mg of isomer 2, MS: m/e 589 [M+H]$^+$.

The N-[3(S)-(benzyloxyformamido)-4-cyclohexyl-2-(R and S)-hydroxybutyl]-L-proline tert.butyl ester used as the starting material was prepared as follows:

(i) A solution of 19.6 g of N-(benzyloxycarbonyl)-3-cyclohexyl-L-alanine in 60 ml of tetrahydrofuran was cooled to −10° C. and 8.9 ml of N-ethylmorpholine were added. 11.6 ml of isobutyl chloroformate were added dropwise and the mixture was stirred at −10° C. for a further 15 minutes. 250 ml of diethyl ether were added and the mixture was filtered. The filtrate was added to a cold solution of diazomethane in diethyl ether (prepared from 21.5 g of N-methyl-N-nitroso-4-toluenesulphonamide) and the mixture was stirred at room temperature for 1.5 hours. The solution was then washed with two 200 ml portions of water and with 200 ml of saturated sodium bicarbonate solution, dried over anhydrous sodium sulphate and evaporated to give 6.6 g of benzyl [2-cyclohexyl-1(S)-(2-diazoacetyl)ethyl]carbamate as a yellow oil which was used without further purification.

(ii) A solution of 6.6 g of the above product in 60 ml of diethyl ether was stirred at room temperature while hydrogen chloride was bubbled through the solution for 30 minutes. The solvent was removed by evaporation and the resulting oil was crystallized from a mixture of diethyl ether and n-hexane to give 5.8 g of [N-(benzyloxycarbonyl)-3-cyclohexyl-L-alanyl]methyl chloride which was used without further purification.

(iii) A solution of 4.4 g of the above product in a mixture of 90 ml of tetrahydrofuran and 10 ml of water was cooled to 0° C. and 0.75 g of sodium borohydride was added. The mixture was stirred at 0° C. for 1 hour and then evaporated to dryness. The residue was taken up in 100 ml of dichloromethane and 100 ml of water, the aqueous layer was adjusted to pH 3 with concentrated hydrochloric acid and the organic layer was separated, dried over anhydrous sodium sulphate and evaporated. The residue was triturated with 200 ml of hot n-hexane and filtered off to give 2.65 g of 3(S)-(benzyloxyformamido)-1-chloro-4-cyclohexyl-2(R and S)-butanol as a white solid; MS: 339, 341 [M]$^+$.

(iv) 14 ml of 0.71M ethanolic potassium hydroxide solution were added to a solution of 2.65 g of the above product in 60 ml of ethanol. The mixture was stirred at room temperature for 1 hour and then evaporated to dryness. The residue was partitioned between 100 ml of dichloromethane and 100 ml of water and the organic layer was dried over anhydrous sodium sulphate and evaporated. The residue was chromatographed on silica gel using 3% methanol in dichloromethane for the elution. There were obtained 1.84 g of 3(S)-(benzyloxyformamido)-4-cyclohexyl-1,2(R and S)-epoxybutane as an oil; MS: m/e 303 [M]$^+$.

(v) A solution of 1.84 g of the above product and 1.21 g of L-proline tert.butyl ester in 65 ml of methanol was heated under reflux for 24 hours. The mixture was evaporated to dryness and the crude product was chromatographed on silica gel using 5% methanol in dichloromethane for the elution. There was obtained 0.41 g of N$_2$-[3(S)-(benzyloxyformamido)-4-cyclohexyl-2(R or S)-hydroxybutyl]-L-proline tert.butyl ester (isomer 1) as a colourless oil; NMR (CDCl$_3$, 250 MHz) δ0.78–1.0 (2H, m), 1.1–1.4 (5H, m), 1.43 (9H, s), 1.55–1.7 (5H, m) 1.8–1.95 (4H, m), 2.03–2.15 (1H, m), 2.3–2.4 (1H, m), 2.5 (1H, dd), 2.66 (1H, t), 3.16–3.26 (2H, m) 3.55–3.7 (2H, m), 4.08 (1H, broad s), 5.02–5.15 (3H, m), 7.25–7.4 (5H, m).

Further elution with the same solvent system yielded 1.18 g of isomer 2 as a colourless oil; NMR (CDCl$_3$, 300 MHz) δ0.75–0.85 (1H, m), 0.9–1.0 (1H, m), 1.1–1.4 (5H, m), 1.43. (9H, s), 1.58–1.70 (5H, m),1.75–1.9 (5H, m), 2.05–2.18 (1H, m), 2.54–2.75 (3H,. m), 3.05–3.15 (2H, m), 3.45–3.52 (1H, m), 3.7–3.8 (1H, m), 4.96–5.15 (3H, m), 7.3–7.38 (5H, m).

EXAMPLE 20

0.663 g (1.42 mmol) of N$_2$-[3(S)-(benzyloxyformamido)-2(R and S)-hydroxy-4-phenylbutyl]-N$^1$-isobutyl-L-prolinamide was hydrogenated in 30 ml of methanol in the presence of 0.539 g (2.84 mmol) of toluene-4-sulphonic acid and 0.1 g of 5% palladium-on-carbon, and the product was then coupled with 0.378 g (1.42 mmol) of N-(benzyloxycarbonyl)-L-asparagine and worked-up as described in Example 1. The crude product was subjected to flash chromatography on silica gel using System F and there were obtained 80 mg of N$^2$-[3(S)-[[N-(benzyloxycarbonyl)-L-asparaginyl]amino]-2(R or S)-hydroxy-4-phenylbutyl]-N$^1$-isobutyl-L-prolinamide (isomer 1) as a solid; Rf (System E) 0.46; MS: m/e 582 [M+H]$^+$.

The column was then eluted with System C to give 70 mg of isomer 2 as a solid; Rf (System E) 0.33; MS: m/e 582 [M+H]$^+$.

The N$_2$-[3(S)-(benzyloxyformamido)-2(R and S)-hydroxy-4-phenylbutyl]-N$^1$-isobutyl-L-prolinamide used as the starting material was prepared as follows:

(i) N$^1$-isobutyl-L-prolinamide was prepared as described in Example 17(i) using isobutylamine in place of isopentylamine.

(ii) A solution of 1.5 g (3.98 mmol) of [N-(benzyloxycarbonyl)-L-phenylalanyl]methyl bromide, 0.678 g (3.98 mmol) of N$^1$-isobutyl-L-prolinamide and 0.402 g (3.98 mmol) of triethylamine in 30 ml of dichloromethane was stirred at room temperature for 4 hours. The solvent was removed by evaporation and 50 ml of ethyl acetate were added. The resulting solid was removed by filtration and discarded. The filtrate was washed with water, sodium bicarbonate solution and saturated sodium chloride solution and then dried over anhydrous sodium sulphate. The solvent was removed by evaporation and the crude product was chromatographed on silica gel using chloroform for the elution to give 1.6 g of N$_2$-[[N-(benzyloxycarbonyl)-L-phenylalanyl]methyl]-N$^1$-isobutyl-L-prolinamide as a solid; MS: m/e 466 [M+H]$^+$.

(iii) A solution of 0.7 g (1.5 mmol) of N$_2$-[[N-(benzyloxycarbonyl)-L-phenylalanyl]methyl]-N$^1$-isobutyl-L-prolinamide in 20 ml of ethanol was treated with 0.143 g (3.75 mmol) of sodium borohydride at room temperature for 2 hours. The solvent was removed by evaporation and the residue was partitioned between ethyl acetate and water. The ethyl acetate phase was washed with saturated sodium chloride solution, dried over anhydrous sodium sulphate and evaporated to give 0.67 g of $N_2$-[3(S)-(benzyloxyformamido)-2(R and S)-hydroxy-4-phenylbutyl]-$N^1$-isobutyl-L-prolinamide as a solid; Rf (System A) 0.39 and 0.33; MS: m/e 467 [M]$^+$.

EXAMPLE 21

A solution of 249 mg of N-[3(S)-[[L-asparaginyl]amino]-2(R)-hydroxy-4-phenylbutyl]-L-proline tert.butyl ester, 106 mg of 2-naphthoyl chloride and 72 mg of diisopropylethylamine in 10 ml of dry dichloromethane was stirred at 20° C. for 20 hours. The gelatinous reaction mixture was partitioned between dichloromethane and water. The organic phase was evaporated and the resulting oil was crystallized from ethyl acetate/n-hexane to give 215 mg of N-[2(R)-hydroxy-3(S)-[[N-(2-naphthoyl)-L-asparaginyl]amino]-4-phenylbutyl]-L-proline tert.butyl ester, as a white solid; MS: m/e 603 [M+H]$^+$.

The N-[3(S)-[[L-asparaginyl]amino]-2(R)-hydroxy-4-phenylbutyl]-L-proline tert.butyl ester used as the starting material was prepared as follows:

A solution of 1.75 g of N-[3(S)-[[N-(benzyloxycarbonyl)-L-asparaginyl]amino]-2(R)-hydroxy-4-phenylbutyl]-L-proline tert.butyl ester in 100 ml of ethanol was hydrogenated over 10% palladium-on-carbon for 64 hours. The catalyst was removed by filtration and the filtrate was evaporated. The residual gum was partitioned between ethyl acetate and 2M hydrochloric acid. The aqueous phase was made basic with dilute sodium hydroxide solution and extracted with ethyl acetate. The ethyl acetate extract was evaporated to give 1.14 g of N-[3(S)-[[L-asparaginyl]amino]-2(R)-hydroxy-4-phenylbutyl]-L-proline tert.butyl ester as a white, solid foam; MS: m/e 449 [M+H]$^+$.

EXAMPLE 22

In a manner analogous to that described in Example 21, from 223 mg of N-[3(S)-[[L-asparaginyl]amino]-2(R)-hydroxy-4-phenylbutyl]-L-proline tert.butyl ester, 95 mg of toluene-4-sulphonyl chloride and 65 mg of diisopropylethylamine there were obtained 170 mg of N-[2(R)-hydroxy-4-phenyl-3(S)-[[N-(p-toluenesulphonyl)-L-asparaginyl]amino]butyl]-L-proline tert.butyl ester as a white solid (from ethylacetate/n-hexane): MS: m/e 603 [M+H]$^+$.

EXAMPLE 23

In a manner analogous to that described in Example 21, from 223 mg of N-[3(S)-[[L-asparaginyl]amino]-2(R)-hydroxy-4-phenylbutyl]-L-proline tert.butyl ester, 77 mg of phenylacetyl chloride and 65 mg of diisopropylethylamine there were obtained 190 mg of N-[2(R)-hydroxy-4-phenyl-3(S)-[[N-(phenylacetyl)-L-asparaginyl]amino]butyl]-L-proline tert.butyl ester as a white solid (from ethyl acetate/n-hexane): MS: m/e 567 [M+H]$^+$.

EXAMPLE 24

In a manner analogous to that described in Example 21, from 249 mg of N-[3(S)-[[L-asparaginyl]amino]-2(R)-hydroxy-4-phenylbutyl]-L-proline tert.butyl ester, 94 mg of hydrocinnamoyl chloride and 72 mg of diisopropylethylamine there were obtained 214 mg of N-[3(S)-[(N-hydrocinnamoyl-L-asparaginyl)amino]-2(R)-hydroxy-4-phenylbutyl]-L-proline tert.butyl ester as a white solid (from ethyl acetate/n-hexane); MS: m/e 581 [M+H]$^+$.

EXAMPLE 25

In a manner analogous to that described in Example 21, from 270 mg of N-[3(S)-[[L-asparaginyl]amino]-2(R)-hydroxy-4-phenylbutyl]-L-proline tert.butyl ester, 114 mg of 1-naphthoyl chloride and 77 mg of diisopropylamine there were obtained, after chromatography on silica gel using 10% methanol in dichloromethane for the elution, 130 mg of N-[2(R)-hydroxy-3(S)-[[N-(1-naphthoyl)-L-asparaginyl]amino]-4-phenylbutyl]-L-proline tert.butyl ester as a white solid; MS: m/e 603 [M+H]$^+$.

EXAMPLE 26

In a manner analogous to that described in Example 21, from 270 mg of N-[3(S)-[[n-asparaginyl]amino]-2(R)-hydroxy-4-phenylbutyl]-L-proline tert.butyl ester, 100 mg of cinnamoyl chloride and 77 mg of diisopropylethylamine there were obtained, after chromatography on silica gel using 10% methanol in dichloromethane for the elution, 99 mg of N-[3(S)-[(N-cinnamoyl-L-asparaginyl)amino]-2(R)-hydroxy-4-phenylbutyl]-L-proline tert.butyl ester as a white solid; MS: m/e 579 [M+H]$^+$.

EXAMPLE 27

A solution of 270 mg of N-[3(S)-[[L-asparaginyl]amino]-2(R)-hydroxy-4-phenylbutyl]-L-proline tert.butyl ester and 98 mg of 4-phenylbutyric acid in 10 ml of dry tetrahydrofuran was cooled in an ice/salt mixture. 81 mg of hydroxybenzotriazole, 69 mg of N-ethylmorpholine and 136 mg of dicyclohexylcarbodiimide were added and the mixture was stirred for 64 hours. The mixture was then diluted with ethyl acetate and filtered. The filtrate was washed with aqueous sodium bicarbonate solution and sodium chloride solution. The solvent was removed by evaporation and the residue was chromatographed on silica gel using System G for the elution to give 79 mg of N-[2(R)-hydroxy-4-phenyl-3(S)-[[N-(4-phenylbutyryl)-L-asparaginyl]amino]butyl]-L-proline tert.butyl ester as a white solid; MS: m/e 595 [M+H]$^+$.

EXAMPLE 28

In a manner analogous to that described in Example 27, from 249 mg of N-[3(S)-[[L-asparaginyl]amino]-2(R)-hydroxy-4-phenylbutyl]-L-proline tert.butyl ester, 104 mg of 2-naphthylacetic acid, 75 mg of hydroxybenzotriazole, 64 mg of N-ethylmorpholine and 126 mg of dicyclohexylcarbodiimide there were obtained, after chromatography on silica gel using 10% methanol in dichloromethane for the elution, 62 mg of N-[2(R)-hydroxy-3(S)-[[N-[(2-naphthyl)acetyl]-L-asparaginyl]amino]-4-phenylbutyl]-L-proline tert.butyl ester as a white solid: MS: m/e 617 [M+H]$^+$.

EXAMPLE 29

In a manner analogous to that described in Example 27, from 270 mg of N-[3(S)-[[L-asparaginyl]amino]-2(R)-hydroxy-4-phenylbutyl]-L-proline tert.butyl ester, 108 mg of 4-methoxyhydrocinnamic acid, 81 mg of hydroxybenzotriazole, 69 mg of N-ethylmorpholine and 136 mg of dicyclohexylcarbodiimide there were obtained, after chromatography on silica gel using System G for the elution, 113 mg of N-[2(R)-hydroxy-3(S)-[[N-(4-methoxyhydrocinnamoyl)-L-asparaginyl]amino]-4-phenylbutyl]-L-proline tert.butyl ester as a white solid; MS: m/e 611 [M+H]$^+$.

EXAMPLE 30

0.179 g of dicyclohexylcarbodiimide, 0.016 g of hydroxybenzotriazole and 0.09 g of N-ethylmorpholine were added to a stirred solution of 0.238 g of N-[3(S)-amino-2(R or S)-hydroxy-5-methylhexyl]-L-proline tert.butyl ester and 0.210 g of N-(benzyloxycarbonyl)-L-asparagine in 10 ml of tetrahydrofuran at 0° C. The mixture was stirred for 16 hours and then filtered. The filtrate was partitioned between ethyl acetate and water and the organic phase was then washed with sodium bicarbonate solution and sodium chloride solution. The organic phase was evaporated and the residue was chromatographed on silica gel using ethyl acetate/methanol (9:1) for the elution to give, after recrystallization from ethyl acetate/n-hexane, 0.13 g of N-[3(S)-[[N-(benzyloxycarbonyl)-L-asparaginyl]amino]-2(R or S)-hydroxy-5-methylhexyl)]-L-proline tert.butyl ester as a white solid; MS: m/e 549 [M+H]$^+$.

The N-[3(S)-amino-2(R or S)-hydroxy-5-methylhexyl]-L-proline tert.butyl ester used as the starting material was prepared as follows:

(i) A solution of 1.31 g of 3(S)-(benzyloxyformamido)-1,2(R or S)-epoxy-5-methylhexane and 0.855 g of proline tert.butyl ester in 10 ml of dimethylformamide was stirred at 100° C. for 16 hours and the solvent was then removed by evaporation. The residue was partitioned between ethyl acetate and water. The organic phase was washed with sodium chloride solution and evaporated. The residue was chromatographed on silica gel using ethyl acetate/acetic acid/ethanol (4:1:1) for the elution. Material having a Rf of approximately 0.24 was re-chromatographed on silica gel using System H for the elution to give 0.358 g of N-[3(S)-(benzyloxyformamido)-2(R or S)-hydroxy-5-methylhexyl]-L-proline tert.butyl ester in the form of a colourless oil; MS: m/e 435 [M+H]$^+$.

(ii) A solution of 0.35 g of N-[3(S)-(benzyloxyformamido)-2(R or S)-hydroxy-5-methylhexyl)]-L-proline tert.butyl ester in 20 ml of ethanol was hydrogenated over 10% palladium-on-carbon for 16 hours. The catalyst was removed by filtration and the filtrate was evaporated to give 0.238 g of N-[3(S)-amino-2(R or S)-hydroxy-5-methylhexyl]-L-proline tert.butyl ester in the form of a colourless gum: MS: m/e 301 [M+H]$^+$.

EXAMPLE 31

A solution of 0.28 g of N-[3(S)-[[L-asparaginyl]amino]-2(R)-hydroxy-4-phenylbutyl]-L-proline tert.butyl ester, and 0.083 g of benzyl isocyanate in 5 ml of dichloromethane was stirred at 20° C. for 2 hours. The solvent was then removed by evaporation and the residue was triturated with diethyl ether to give 0.174 g of N-[3(S)-[[N-(benzylcarbamoyl)-L-asparaginyl]amino]-2(R)-hydroxy-4-phenylbutyl]-L-proline tert.butyl ester as a white solid; MS: m/e 582 [M+H]$^+$.

EXAMPLE 32

A solution of 0.28 g of N-[3(S)-[[L-asparaginyl]-amino]-2(R)-hydroxy-4-phenylbutyl]-L-proline tert.butyl ester, 0.124 g of 1-adamantanecarbonyl chloride and 0.081 g of diisopropylethylamine in 5 ml of dichloromethane was stirred at 20° C. for 8 hours. A further 0.124 g of 1-adamantanecarbonyl chloride and 0.081 g of diisopropylethylamine were added and stirring was continued at 20° C. for 16 hours. The solution was diluted with 20 ml of dichloromethane and washed in sequence with water, sodium carbonate solution, potassium bisulphate solution and sodium chloride solution. The organic solution was then evaporated and the residue was triturated with diethyl ether to give 0.2 g of N-[3(S)-[[N-(1-adamantylcarbonyl)-L-asparaginyl]amino]-2(R)-hydroxy-4-phenylbutyl-L-proline tert.butyl ester as a white solid; MS: m/e 611 [M+H]$^+$.

EXAMPLE 33

0.208 g of dicyclohexylcarbodiimide, 0.124 g of hydroxybenzotriazole and 0.106 g of N-ethylmorpholine were added to a stirred solution of 0.315 g of $N^2$-[3(S)-amino-2(R)-hydroxy-4-phenylbutyl]-$N^1$-phenyl-L-prolinamide and 0.244 g of N-(benzyloxycarbonyl)-L-asparagine in 10 ml of tetrahydrofuran at 0° C. The mixture was stirred for 16 hours, then diluted with ethyl acetate and filtered. The filtrate was washed with sodium bicarbonate solution and sodium chloride solution and the solvent was then removed by evaporation. The residue was chromatographed on silica gel using dichloromethane/methanol (9:1) for the elution to give 0.22 g of $N_2$-[3(S)-[[N-(benzyloxycarbonyl)-L-asparaginyl]amino]-2(R)-hydroxy-4-phenylbutyl]-$N^1$-phenyl-L-prolinamide in the form of a white solid of melting point 169°–171° C. (from methanol).

The $N^2$-[3(S)-amino-2(R)-hydroxy-4-phenylbutyl]-$N^1$-phenyl-L-prolinamide used as the starting material was prepared as follows:

(i) 3.5 g of sodium borohydride were added to an ice-cooled stirred solution of 21 g of [N-(benzyloxycarbonyl)-L-phenylalanyl]methyl chloride in 500 ml of aqueous tetrahydrofuran. Stirring was continued for 0.5 hour and the solvent was removed by evaporation. The residue was partitioned between dichloromethane and water and then carefully acidified with concentrated hydrochloric acid. After working-up the organic phase gave a white solid which ran as two spots; Rf 0.4 and 0.5 (5% methanol/chloroform). The solids were extracted with boiling hexane until all of the higher running component had been extracted. The combined n-hexane extracts were evaporated and the residue was re-extracted with boiling n-hexane to remove a small amount (0.5 g) of the lower running component. In this manner there were obtained 11.5 g of 3(S)-(benzyloxyformamido)-1-chloro-4-phenyl-2(S)-butanol of melting point 151°–153° C. (from ethyl acetate/n-hexane).

(ii) A solution of 11.4 g of 3(S)-(benzyloxyformamido)-1-chloro-4-phenyl-2(S)-butanol in 300 ml of ethanol containing 2.24 g of potassium hydroxide was left to stand for 15 minutes. The solvent was removed by evaporation and the residue was partitioned between water and dichloromethane. Working-up gave 10.1 g of crude 3(S)-(benzyloxyformamido)-1,2(S)-epoxy-4-phenylbutane as an off-white solid which was used without further purification.

(iii) A solution of 0.594 g of 3(S)-(benzyloxyformamido)-1,2(S)-epoxy-4-phenylbutane and 0.38 g of $N^1$-phenyl-L-prolinamide in 5 ml of dimethylformamide was heated to 90° C. for 16 hours and then to 120° C. for 8 hours. The solvent was removed by evaporation and the residue was chromatographed on silica gel using diethyl ether/methanol (96:4) for the elution to give 0.48 g of $N_2$-[3(S)-(benzyloxyformamido)-2(R)-hydroxy-4-phenylbutyl]-$N^1$-phenyl-L-prolinamide in the form of a white solid of melting point 133°–135° C. (from diethyl ether).

(iv) A solution of 0.45 g of $N^2$-[3(S)-(benzyloxyformamido)-2(R)-hydroxy-4-phenylbutyl]-$N^1$-phenyl-L-prolinamide in 20 ml of ethanol was hydrogenated over 10% palladium-on-carbon for 4 hours to give 0.315 g of $N^2$-[3(S)-amino-2(R)-hydroxy-4-phenylbutyl]-$N^1$-phenyl-L-prolinamide in the form of a white solid; MS: m/e 354 [M+H]$^+$.

EXAMPLE 34

In a manner analogous to that described in Example 33, from 0.987 mg of 2-[3(S)-(benzyloxyformamido)-2(R)-hydroxy-4-phenylbutyl]-N-tert.butyl-1,2,3,4-tetrahydro-3(R,S)-isoquinolinecarboxamide, 0.665 g of N-(benzyloxycarbonyl)-L-asparagine, 566 mg of dicyclohexylcarbodiimide, 0.337 g of hydroxybenzotriazole and 0.287 g of N-ethylmorpholine there was obtained 0.5 g of 2-[3(S)-[[N-(benzyloxycarbonyl)-L-asparaginyl]amino]-2(R)-hydroxy-4-phenylbutyl]-N-tert.butyl-1,2,3,4-tetrahydro-3(R,S)-isoquinolinecarboxamide as a pale cream foam; MS: m/e 644 [M+H]$^+$.

EXAMPLE 35

In a manner analogous to that described in Example 33, from 0.225 g of dicyclohexylcarbodiimide, 0.135 g of hydroxybenzotriazole, 0.115 g of N-ethylmorpholine, 0.38 g of N$^2$-[3(S)-amino-2(R)-hydroxy-4-phenylbutyl]-N$^1$-benzyl-L-prolinamide and 0.266 g of N-(benzyloxycarbonyl)-L-asparagine there was obtained 0.056 g of N$^1$-benzyl-N$_2$-[3(S)-[[N-(benzyloxycarbonyl)-L-asparaginyl]amino]-2(R)-hydroxy-4-phenylbutyl]-L-prolinamide as a white solid; MS: m/e 616 [M+H]$^+$.

EXAMPLE 36

A solution of 270 mg of N-[3(S)-(benzyloxyformamido)-4-(4-fluorophenyl)-2(R)-hydroxybutyl]-L-proline tert.butyl ester in 50 ml of ethanol was hydrogenated over 30 mg of 10% palladium-on-carbon for 2 hours. The catalyst was removed by filtration and the filtrate was evaporated to give an oil which was coupled with 158 mg of N-(benzyloxycarbonyl)-L-asparagine in a manner analogous to that described in Example 1. The crude product was chromatographed on silica gel using 10% methanol in dichloromethane for the elution. There were obtained 120 mg of N-[3(S)-[[N-(benzyloxycarbonyl)-L-asparaginyl]amino]-4-(4-fluorophenyl)-2(R)-hydroxybutyl]-L-proline tert.butyl ester as a white solid of melting point 163°–164° C.

The N-[3(S)-(benzyloxyformamido)-4-(4-fluorophenyl)-2(R)-hydroxybutyl]-L-proline tert.butyl ester used as the starting material was prepared as follows:

(i) In a manner analogous to that described in Example 19(i), 7.70 g of N-(benzyloxycarbonyl)-3-(4-fluorophenyl)-DL-alanine were treated with isobutyl chloroformate followed by reaction with diazomethane to give 7.15 g of benzyl [2-(4-fluorophenyl)-1(RS)-(2-diazoacetyl)ethyl] carbamate as a yellow solid of melting point 97° C.

(ii) Treatment of the above product with hydrogen chloride in a manner analogous to that described in Example 19(ii) gave 6.70 g of [N-(benzyloxycarbonyl)-3-(4-fluorophenyl)-DL-alanyl]methyl chloride which was used without further purification.

(iii) Reduction of 6.30 g of the above product with sodium borohydride in a manner analogous to that described in Example 19(iii) gave 5.83 g of a mixture of alcohols. This mixture was chromatographed on a column of silica gel using 2% methanol in dichloromethane for the elution to give 0.95 g of threo-3-(benzyloxyformamido)-1-chloro-4-(4-fluorophenyl)-2-butanol as a white solid. Further elution of the column with the same solvent system gave 3.25 g of erythro-3-(benzyloxyformamido)-1-chloro-4-(4-fluorophenyl)-2-butanol as a white solid of melting point 148°–149° C.

(iv) Treatment of 3.20 g of erythro-3-(benzyloxyformamido)-1-chloro-4-(4-fluorophenyl)-2-butanol with ethanolic potassium hydroxide solution in a manner analogous to that described in Example 19(iv) gave 2.03 g of erythro-3-(benzyloxyformamido)-1,2-epoxy-4-(4-fluorophenyl)butane as a white solid; MS: m/e 315 [M]$^+$.

(v) 0.63 g of the above product was treated with L-proline tert.butyl ester in a manner analogous to that described in Example 19(v). The crude product was chromatographed on a column of silica gel using 5% methanol in dichloromethane for the elution. There was obtained 0.26 g of N-[3(R)-(benzyloxyformamido)-4-(4-fluorophenyl)-2(S)-hydroxybutyl]-L-proline tert.butyl ester as a colourless oil; NMR (CDCl$_3$, 300 MHz) δ1.47 (9H, s), 1.75–1.95 (4H,m), 2.05–2.15 (1H,m), 2.25–2.35 (1H,m), 2.50–3.00 (4H,m), 3.20 (2H,m), 3.58 (1H,m), 3.85 (1H,m), 4.88 (1H,d), 5.00 (2H,dd), 6.94 (2H, t), 7.13–7.37 (7H,m).

Further elution with the same solvent system yielded 0.275 g of N-[3(S)-(benzyloxyformamido)-4-(4-fluorophenyl)-2(R)-hydroxybutyl]-L-proline tert.butyl ester as a colourless oil; NMR (CDCl$_3$, 300 MHz) δ1.42 (9H,s), 1.75–1.95 (4H,m), 2.05–2.20 (1H,m), 2.54–2.80 (3H,m), 2.85–2.98 (2H,m), 3.03–3.24 (2H,m), 3.44 (1H,m), 3.92 (1H,m), 4.88–5.06 (3H,m), 6.93 (2H, t), 7.10–7.40 (7H,m).

EXAMPLE 37

A solution of 730 mg of N-[3(S)-(benzyloxyformamido)-2(R)-hydroxy-4-(4-methoxyphenyl)butyl]-L-proline tert.butyl ester in 20 ml of ethanol was hydrogenated over 50 mg of 10% palladium-on-carbon for 2 hours. The catalyst was removed by filtration and the filtrate was evaporated to give an oil which was coupled with 340 mg of N-(benzyloxycarbonyl)-L-asparagine in a manner analogous to that described in Example 1. The crude product was chromatographed on a column of silica gel using 10% methanol in dichloromethane for the elution. There were obtained 82 mg of N-[3(S)-[[N-(benzyloxycarbonyl)-L-asparaginyl]amino]-2(R)-hydroxy-4-(4-methoxyphenyl)butyl]-L-proline tert.butyl ester as a white solid; MS: m/e 613 [M+H]$^+$.

The N-[3(S)-(benzyloxyformamido)-2(R)-hydroxy-4-(4-methoxyphenyl)butyl]-L-proline tert.butyl ester used as the starting material was prepared as follows:

(i) In a manner analogous to that described in Example 19(i), 3.10 g of N-(benzyloxycarbonyl)-3-(4-methoxyphenyl)-L-alanine were treated with isobutyl chloroformate followed by diazomethane to give 2.83 g of benzyl [2-(4-methoxyphenyl)-1(S)-(2-diazoacetyl)ethyl]carbamate as a pale yellow solid of melting point 88°–90° C.

(ii) 2.80 g of the above product were treated with hydrogen chloride in a manner analogous to that described in Example 19(ii) to give 2.85 g of [N-(benzyloxycarbonyl)-3-(4-methoxyphenyl)-L-alanyl]methyl chloride as a white solid of melting point 107° C.

(iii) The above product was treated with sodium borohydride in a manner analogous to that described in Example 19(iii). The crude product was triturated with 30 ml of 5% methanol in dichloromethane to give 1.15 g of 3(S)-(benzyloxyformamido)-1-chloro-4-(4-methoxyphenyl)-2(S)-butanol as a white solid; MS: m/e 363, 365 [M]$^+$.

(iv) The above product was treated with ethanolic potassium hydroxide solution in a manner analogous to that described in Example 19(iv) to give 0.86 g of 3(S)-(benzyloxyformamido)-1,2(S)-epoxy-4-(4-methoxyphenyl)butane as a white solid of melting point 86°–87° C.

(v) 0.51 g of the above product was treated with L-proline tert.butyl ester in a manner analogous to that described in Example 19(v) to give 0.63 g of N-[3(S)-(benzyloxyformamido)-2(R)-hydroxy-4-(4-methoxyphenyl)butyl]-L-proline tert.butyl ester as a colourless oil; MS: m/e 498 [M]$^+$.

EXAMPLE 38

A solution of 1.58 g of $N_2$-[3(S)-(benzyloxyformamido)-4-(4-tert.butoxyphenyl)-2(R)-hydroxybutyl]-$N^1$-tert.butyl-L-prolinamide in 200 ml of ethanol was hydrogenated over 100 mg of 10% palladium-on-carbon for 4 hours. The catalyst was removed by filtration and the filtrate was evaporated to give an oil which was coupled with 0.74 g of N-(benzyloxycarbonyl)-L-asparagine in a manner analogous to that described in Example 1. The crude product was chromatographed on a column of silica gel using 10% methanol in dichloromethane for the elution. There was obtained 0.59 g of $N_2$-[3(S)-[[N-(benzyloxycarbonyl)-L-asparaginyl]amino]-4-(4-tert.butoxyphenyl)-2(R)-hydroxybutyl]-$N^1$-tert.butyl-L-prolinamide as a white solid; MS: m/e 654 $[M+H]^+$.

The $N_2$-[3(S)-(benzyloxyformamido)-4-(4-tert.butoxyphenyl)-2(R)-hydroxybutyl]-$N^1$-tert.butyl-L-prolinamide used as the starting material was prepared as follows:

(i) In a manner analoguous to that described in Example 19(i), N-(benzyloxycarbonyl)-3-(4-tert.butoxyphenyl)-L-alanine (prepared from 7.45 g of the dicyclohexylammonium salt) was treated with isobutyl chloroformate followed by reaction with diazomethane to give 3.58 g of benzyl [2-(4-tert.butoxyphenyl)-1(S)-(2-diazoacetyl)ethyl]carbamate as a yellow solid of melting point 80°–82° C.

(ii) Treatment of the foregoing carbamate with hydrogen chloride in a manner analogous to that described in Example 19(ii) gave 3.6 g of [N-(benzyloxycarbonyl)-3-(4-tert.butoxyphenyl)-L-alanyl]methyl chloride which was used without further purification.

(iii) Reduction of the foregoing chloride with sodium borohydride in a manner analogous to that described in Example 19(iii) gave a mixture of alcohols which was triturated with hot n-hexane to give 3.14 g of a white solid. This solid was recrystallized from a mixture of ethyl acetate and n-hexane to give 1.88 g of 3(S)-(benzyloxyformamido)-4-(4-tert.butoxyphenyl)-1-chloro-2(S)-butanol as a white solid; NMR ($CDCl_3$, 250 MHz) δ1.35 (9H, s), 2.85–3.05 (3H,m), 3.50–3.70 (2H,m), 3.80–3.90 (1H,m), 3.92–4.04 (1H,m), 4.85 (1H,d), 5.00–5.10 (2H,m), 6.93 (2H,d), 7.10 (2H,d), 7.25–7.40 (5H,m).

(iv) 5.52 g of the above product were treated with ethanolic potassium hydroxide solution in a manner analogous to that described in Example 19(iv) to give 4.98 g of 3(S)-(benzyloxyformamido)-4-(4-tert.butoxyphenyl)-1,2(S)-epoxybutane as a colourless gum: NMR ($CDCl_3$, 250 MHz) δ1.36 (9H, s), 2.75–3.05 (5H,m), 3.76 (1H,m), 4.73 (1H,d), 5.07 (2H, s), 6.95 (2H,d), 7.10 (2H,d), 7.25–7.40 (5H,m).

(v) 2.50 g of the above product were treated with $N^1$-tert.butyl-L-prolinamide in a manner analogous to that described in Example 19(v) to give 1.58 g of $N_2$-[3(S)-(benzyloxyformamido)-4-(4-tert.butoxyphenyl)-2(R)-hydroxybutyl]-$N^1$-tert.butyl-L-prolinamide as a colourless oil; MS: m/e 539 $[M]^+$.

EXAMPLE 39

A solution of 200 mg of $N^2$-[3(S)-[[N-(benzyloxycarbonyl)-L-asparaginyl]amino]-4-(4-tert.butoxyphenyl)-2(R)-hydroxybutyl]-$N^1$-tert.butyl-L-prolinamide in 5 ml of trifluoroacetic acid was stirred at room temperature for 20 hours. The solution was poured into excess saturated sodium hydrogen carbonate solution and the mixture was extracted with three 30 ml portions of dichloromethane and three 30 ml portions of ethyl acetate. The combined extracts were dried over anhydrous sodium sulphate and evaporated to give 100 mg of a colourless gum. This was chromatographed on a column of silica gel using 10% methanol in dichloromethane for the elution to give 42 mg of a glass-like solid. This solid was triturated with a mixture of 1 ml of diethyl ether and 3 ml of n-hexane to give 28 mg of $N_2$-[3(S)-[[N-(benzyloxycarbonyl)-L-asparaginyl]amino]-2(R)-hydroxy-4-(4-hydroxyphenyl)butyl]-$N^1$-tert.butyl-L-prolinamide trifluoroacetate as a glass-like solid: MS: m/e 598 $[M—CF_3CO_2]^+$.

EXAMPLE 40

In a manner analogous to that described in Example 1, from $N^2$-[3(S)-(benzyloxyformamido)-2(R)-hydroxy-4-phenylbutyl]-N -tert.butyl-L-prolinamide and N-(benzyloxycarbonyl)-L-aspartic acid 4-methyl ester there was obtained $N_2$-[3(S)-[[N-(benzyloxycarbonyl)-4-O-methyl-L-α-aspartyl]amino]-2(R)-hydroxy-4-phenylbutyl]-$N^1$-tert.butyl-L-prolinamide as a glassy solid of melting point 55°–60° C.; MS: m/e 597 $[M+H]^+$.

EXAMPLE 41

In a manner analogous to that described in Example 1, from $N_2$-[3(S)-(benzyloxyformamido)-2(R)-hydroxy-4-phenylbutyl]-$N^1$-tert.butyl-L-prolinamide and N-(benzyloxycarbonyl)-L-methionine there was obtained $N^2$-[3(S)-[[N-(benzyloxycarbonyl)-L-methionyl]amino]-2(R)-hydroxy-4-phenylbutyl]-$N^1$-tert.butyl-L-prolinamide as a white solid of melting point 132°–133° C.

EXAMPLE 42

$N_2$-[3(S)-[[N,3-bis(Benzyloxycarbonyl)-L-histidyl]amino]-2(R)-hydroxy-4-phenylbutyl]-$N^1$-tert.butyl-L-prolinamide was prepared from $N_2$-[3(S)-(benzyloxyformamido)-2(R)-hydroxy-4-phenylbutyl]-$N^1$-tert.butyl-L-prolinamide and N,3-bis(benzyloxycarbonyl)-L-histidine in an analogous manner to that described in Example 1 and was obtained as a colourless glass; MS: m/e 739 $[M+H]^+$.

EXAMPLE 43

A solution of 30 mg of $N^2$-[3(S)-[[N,3-bis(benzyloxycarbonyl)-L-histidyl]amino]-2(R)-hydroxy-4-phenylbutyl]-N-tert.butyl-L-prolinamide in 6 ml of 2M hydrochloric acid was stirred at room temperature overnight. The mixture was neutralized by the addition of 2M sodium hydroxide solution and extracted with two 10 ml portions of dichloromethane. The combined extracts were dried over anhydrous sodium sulphate and evaporated. The crude product was triturated with diethyl ether to give 14 mg of $N_2$-[3(S)-[[N-(benzyloxycarbonyl)-L-histidyl]amino]-2(R)-hydroxy-4-phenylbutyl]-$N^1$-tert.butyl-L-prolinamide as a white solid of melting point 100° C. (decomposition); MS: m/e 604 $[M]^+$.

EXAMPLE 44

In a manner analogous to that described in Example 21, from 224 mg of N-[3(S)-[[L-asparaginyl]amino]-2(R)-hydroxy-4-phenylbutyl]-L-proline tert.butyl ester, 70 mg of benzoyl chloride and 65 mg of diisopropylethylamine there were obtained, after chromatography on silica gel using 10% methanol in dichloromethane for the elution, 20 mg of N-[3(S)-[(N-benzoyl-L-asparaginyl)amino]-2(R)-hydroxy-4-phenylbutyl]-L-proline tert.butyl ester as a white solid from methanol/diethyl ether; MS: m/e 553 $[M+H]^+$.

EXAMPLE 45

In a manner analogous to that described in Example 27, from 224 mg of N-[3(S)-[[L-asparaginyl]amino]-2(R)-hydroxy-4-phenylbutyl]-L-proline tert.butyl ester, 93 mg of 1-naphthylacetic acid, 68 mg of hydroxybenzotriazole, 58 mg of N-ethylmorpholine and 113 mg of dicyclohexylcarbodiimide there were obtained, after chromatography on silica gel using 10% methanol in dichloromethane for the elution, 106 mg of N-[2(R)-hydroxy-3(S)-[[N-[2-(1-naphthyl)acetyl]-L-asparaginyl]amino]-4-phenylbutyl]-L-proline tert.butyl ester as a white solid from methanol/diethyl ether; MS: m/e 617 [M+H]$^+$.

EXAMPLE 46

In a manner analogous to that described in Example 27, from 493 mg of N-[3(S)-[[n-asparaginyl]amino]-2(R)-hydroxy-4-phenylbutyl]-L-proline tert.butyl ester, 190 mg of quinaldic acid, 149 mg of hydroxybenzotriazole, 127 mg of N-ethylmorpholine and 249 mg of dicyclohexylcarbodiimide there were obtained, after chromatography on silica gel using 10% methanol in dichloromethane for the elution, 167 mg of N-[2(R)-hydroxy-4-phenyl-3(S)-[[N-(2-quinolylcarbonyl)-L-asparaginyl]amino]butyl]-L-proline tert.butyl ester as a white solid from methanol/diethyl ether; MS: m/e 604 [M+H]$^+$.

EXAMPLE 47

In a manner analogous to that described in Example 27, from 234 mg of N-[3(S)-[[L-asparaginyl]amino]-2(R)-hydroxy-4-phenylbutyl]-L-proline tert.butyl ester, 96 mg of 4-chlorohydrocinnamic acid, 70 mg of hydroxybenzotriazole, 60 mg of N-ethylmorpholine and 118 mg of dicyclohexylcarbodiimide there were obtained, after chromatography on silica gel using System G for the elution, 171 mg of N-[3(S)-[[N-(4-chlorohydrocinnamoyl)-L-asparaginyl]amino]-2(R)-hydroxy-4-phenylbutyl]-L-proline tert.butyl ester as a white solid; MS: m/e 615 [M+H]$^+$.

EXAMPLE 48

In a manner analogous to that described in Example 27, from 234 mg of N-[3(S)-[[L-asparaginyl]amino]-2(R)-hydroxy-4-phenylbutyl]-L-proline tert.butyl ester, 90 mg of 1-isoquinolinecarboxylic acid, 70 mg of hydroxybenzotriazole, 60 mg of N-ethylmorpholine and 118 mg of dicyclohexylcarbodiimide there were obtained, after chromatography on silica gel using 10% methanol in dichloromethane for the elution, 146 mg of N-[2(R)-hydroxy-3(S)-[[N-(1-isoquinolylcarbonyl)-L-asparaginyl]amino]-4-phenylbutyl]-L-proline tert.butyl ester as a pale cream solid from ethyl acetate/n-hexane; MS: m/e 604 [M+H]$^+$.

EXAMPLE 49

In a manner analogous to that described in Example 21, from 209 mg of N$_2$-[3(S)-[[L-asparaginyl]amino]-2(R)-hydroxy-4-phenylbutyl]-N$^1$-tert.butyl-L-prolinamide, 89 mg of 2-naphthoyl chloride and 61 mg of diisopropylethylamine there were obtained 191 mg of N$^1$-tert.butyl-N$^2$-[2(R)-hydroxy-3(S)-[[N-(2-naphthoyl)-L-asparaginyl]-amino]-4-phenylbutyl]-L-prolinamide as a white solid; MS: m/e 602 [M+H]$^+$.

The starting material was prepared by hydrogenating N$_2$-[3(S)-[[N-(benzyloxycarbonyl)-L-asparaginyl]amino]-2(R)-hydroxy-4-phenylbutyl]-N$^1$-tert.butyl-L-prolinamide; MS: m/e-582 [M+H]$^+$. The latter compound was obtained in a manner analogous to that described in Example 33, but using N$^1$-tert.butyl-L-prolinamide in paragraph (iii) in place of N$^1$-phenyl-L-prolinamide.

EXAMPLE 50

A solution of 2.798 g of 1-[3(S)-amino-2(R)-hydroxy-4-phenylbutyl]-N-tert.butyl-octahydro-cyclopenta[b]pyrrole-2-carboxamide (four diastereomers) and 2.72 g of N-(benzyloxycarbonyl)-L-asparagine succinimide ester in 50 ml of dimethoxyethane was stirred at 20° C. for 2 hours and the solvent was then removed by evaporation. The residue was taken up in ethyl acetate and the solution was washed with aqueous sodium carbonate solution and sodium chloride solution. The organic solution was evaporated and the residue was chromatographed on silica gel using system G for the elution. There were obtained 434 mg of 1-[3(S)-[[N-(benzyloxycarbonyl)-L-asparaginyl]amino]-2(R)-hydroxy-4-phenylbutyl]-N-tert.butyl-octahydro-(3aS,6aS)-cyclopenta[b]pyrrole-2(S)-carboxamide as a white solid from ethyl acetate; MS: m/e 622 [M+H]$^+$; Rf: 0.22.

The 1-[3(S)-amino-2(R)-hydroxy-4-phenylbutyl]-N-tert.butyl-octahydro-cyclopenta[b]pyrrole-2-carboxamide used as the starting material was prepared as follows:

(i) A solution of 2.98 g of 3(S)-(benzyloxyformamido)-1,2(S)-epoxy-4-phenylbutane and 2.1 g of N-tert.butyl-octahydro-cyclopenta[b]pyrrole-2-carboxamide in 50 ml of ethanol was heated at reflux for 10 hours and the solvent was then removed by evaporation. Chromatography on silica gel using System H for the elution then gave 4.7 g of 1-[3(S)-(benzyloxyformamido)-2(R)-hydroxy-4-phenylbutyl]-N-tert.butyl-octahydro-cyclopenta[b]pyrrole-2-carboxamide as a mixture of four diastereomers: MS: m/e 508 [M+H]$^+$.

(ii) A solution of 4.6 g of 1-[3(S)-(benzyloxyformamido)-2(R)-hydroxy-4-phenylbutyl]-N-tert.butyl-octahydro-cyclopenta[b]pyrrole-2-carboxamide (four diastereomers) in 90 ml of ethanol was hydrogenated over 10% palladium-on-carbon at 20° C. and under atmospheric pressure for 72 hours. The catalyst was removed by filtration and the filtrate was evaporated to give 2.958 g of 1-[3(S)-amino-2(R)-hydroxy-4-phenylbutyl]-N-tert.butyl-octahydro-cyclopenta[b]pyrrole-2-carboxamide (four diastereomers) as a brownish oil; MS: m/e 374 [M+H]$^+$.

EXAMPLE 51

In a manner analogous to that described in Example 27, from 310 mg of 1-[3(S)-[[L-asparaginyl]amino]-2(R)-hydroxy-4-phenylbutyl]-N-tert.butyl-octahydro-(3aS,6aS)-cyclopenta[b]pyrrole-2(S)-carboxamide, 111 mg of quinaldic acid, 86 mg of hydroxybenzotriazole, 74 mg of N-ethylmorpholine and 132 mg of dicyclohexylcarbodiimide there were obtained, after chromatography on silica gel using dichloromethane/methanol (9:1) for the elution, 200 mg of N-tert.butyl-octahydro-1-[2(R)-hydroxy-4-phenyl-3(S)-[[N-(2-quinolylcarbonyl)-L-asparaginyl]amino]butyl]-(3aS,6aS)-cyclopenta[b]pyrrole-2(S)-carboxamide as a white solid: MS: m/e 643 [M+H]$^+$.

The 1-[3(S)-[[L-asparaginyl]amino]-2(R)-hydroxy-4-phenylbutyl]-N-tert.butyl-octahydro-(3aS,6aS)-cyclopenta[b]pyrrole-2(S)-carboxamide used as the starting material was prepared as follows:

A solution of 397 mg of 1-[3(S)-[[N-(benzyloxycarbonyl)-L-asparaginyl]amino]-2(R)-hydroxy-4-phenylbutyl]-N-tert.butyl-octahydro-(3aS,6aS)-cyclopenta[b]pyrrole-2(S)-carboxamide in 20 ml of ethanol was hydrogenated over 10% palladium-on-carbon at 20° C. and under atmospheric pressure for 4 hours, The catalyst was removed by filtration and the filtrate was evaporated to give 312 mg of 1-[3(S)-[[L-asparaginyl]amino]-2(R)-hydroxy-4-phenylbutyl]-N-tert.butyl-octahydro-(3aS,6aS)-cyclopenta[b]pyrrole-2(S)-carboxamide as a pale yellow gum; m/e 488 [M+H]⁺.

EXAMPLE 52

In a manner analogous to that described in Example from 295 mg of $N_2$-[3(S)-[[L-asparaginyl]amino]-2(R)-hydroxy-4-phenylbutyl]-$N^1$-tert.butyl-L-prolinamide, 204 mg of 6-(benzyloxycarbonyl)-2-naphthoic acid, 20 mg of hydroxybenzotriazole, 77 mg of N-ethylmorpholine and 151 mg of dicyclohexylcarbodiimide there were obtained, after chromatography on silica gel using System G for the elution, 340 mg of $N^2$-[3(S)-[[N-[6-(benzyloxycarbonyl)-2-naphthoyl]-L-asparaginyl]amino]-2(R)-hydroxy-4-phenylbutyl]-$N^1$-tert.butyl-L-prolinamide as an off-white solid from ethyl acetate/n-hexane; MS: m/e 736 [M+H]⁺.

EXAMPLE 53

294 mg of $N_2$-[3(S)-[[N-[6-(benzyloxycarbonyl)-2-naphthoyl]-L-asparaginyl]amino]-2(R)-hydroxy-4-phenylbutyl]-$N^1$-tert.butyl-L-prolinamide in 100 ml of isopropanol was hydrogenated over 10% palladium-on-carbon at 20° C. and under atmospheric pressure for 16 hours. The catalyst was removed by filtration and the filtrate was evaporated to give 145 mg of $N^2$-[3(S)-[[N-(6-carboxy-2-naphthoyl)-L-asparaginyl]amino]-2(R)-hydroxy-4-phenylbutyl]-$N^1$-tert.butyl-L-prolinamide as a white solid from methanol/ethyl acetate; MS: m/e 646 [M+H]⁺.

EXAMPLE 54

In a manner analogous to that described in Example 27, from 295 mg of $N_2$-[3(S)-[[n-asparaginyl]amino]-2(R)-hydroxy-4-phenylbutyl]-$N^1$-tert.butyl-L-prolinamide, 171 mg of 4-(benzyloxycarbonyl)benzoic acid, 90 mg of hydroxybenzotriazole, 77 mg of N-ethylmorpholine and 151 mg of dicyclohexylcarbodiimide there were obtained, after chromatography on silica gel using System G for the elution, 390 mg of $N_2$-[3(S)-[[N-[4-(benzyloxycarbonyl)benzoyl]-L-asparaginyl]amino]-2(R)-hydroxy-4-phenylbutyl]-$N^1$-tert.butyl-L-prolinamide as an off-white solid from ethyl acetate/n-hexane; MS: m/e 686 [M+H]⁺.

EXAMPLE 55

274 mg of $N^2$-[3(S)-[[N-[4-(benzyloxycarbonyl)benzoyl]-L-asparaginyl]amino]-2(R)-hydroxy-4-phenylbutyl]-$N^1$-tert.butyl-L-prolinamide in 100 ml of isopropanol were hydrogenated over 10% palladium-on-carbon at 20° C. and under atmospheric pressure for 16 hours. The catalyst was removed by filtration and the filtrate was evaporated to give 193 mg of $N_2$-[3(S)-[[N-(4-carboxybenzoyl)-L-asparaginyl]amino]-2(R)-hydroxy-4-phenylbutyl]-$N^1$-tert.butyl-L-prolinamide as a white solid from methanol/ethyl acetate; MS: m/e 596 [M+H]⁺.

EXAMPLE 56

In a manner analogous to that described in Example 27, from 228 mg of $N_2$-[3(S)-[[L-asparaginyl]amino]-2(R)-hydroxy-4-phenylbutyl]-$N^1$-tert.butyl-L-prolinamide, 98 mg of 4-nitrocinnamic acid, 69 mg of hydroxybenzotriazole, 59 mg of N-ethylmorpholine and 116 mg of dicyclohexylcarbodiimide there were obtained, after chromatography on silica gel using dichloromethane/methanol (9:1) for the elution, 68 mg of $N^1$-tert.butyl-$N^2$-[2(R)-hydroxy-3(S)-[[N-(4-nitrocinnamoyl)-L-asparaginyl]amino]-4-phenylbutyl]-L-prolinamide as a white solid from methanol/diethyl ether; MS: m/e 623 [M+H]⁺.

EXAMPLE 57

A solution of 200 mg of $N^1$-tert.butyl-$N_2$-[2(R)-hydroxy-3(S)-[[N-(4-nitrocinnamoyl)-L-asparaginyl]amino]-4-phenylbutyl]-L-prolinamide in 20 ml of ethanol was hydrogenated over 10% palladium-on-carbon at 20° C. and under atmospheric pressure for 5 hours. The catalyst was removed by filtration and the filtrate was evaporated. The residue was chromatographed on silica gel using dichloromethane/methanol (9:1) for the elution to give 40 mg of $N^2$-[3(S)-[[N-(4-aminohydrocinnamoyl)-L-asparaginyl]amino]-2(R)-hydroxy-4-phenylbutyl]-$N^1$-tert.butyl-L-prolinamide as a white solid from methanol/ethyl acetate; MS: m/e 595 [M+H]⁺.

EXAMPLE 58

In a manner analogous to that described in Example 27, from 418 mg of $N^2$-[3(S)-[[L-asparaginyl]amino]-2(R)-hydroxy-4-phenylbutyl]-$N^1$-tert.butyl-L-prolinamide, 205 mg of 1-acetyl-1,2,3,4-tetrahydro-2(R,S)-quinoline-carboxylic acid, 127 mg of hydroxybenzotriazole, 108 mg of N-ethylmorpholine and 212 mg of dicyclohexylcarbodiimide there were obtained, after purification by chromatography on silica gel using dichloromethane/methanol (9:1) for the elution, 220 mg of $N^2$-[3(S)-[[N-[(1-acetyl-1,2,3,4-tetrahydro-2(RS)-quinolyl)carbonyl]-L-asparaginyl]amino]-2(R)-hydroxy-4-phenylbutyl-$N^1$-tert.butyl-L-prolinamide (two diastereomers) as a white solid from dichloromethane/diethyl ether; MS: m/e 649 [M+H]⁺.

EXAMPLE 59

In a manner analogous to that described in Example 27, from 418 mg of $N^2$-[3(S)-[(L-asparaginyl)amino]-2(R)-hydroxy-4-phenylbutyl]-$N^1$-tert.butyl-L-prolinamide, 179 mg of 1,2,3,4-tetrahydro-1-oxo-3(RS)-isoquinolinecarboxylic acid, 127 mg of hydroxybenzotriazole, 108 mg of N-ethylmorpholine and 212 mg of dicyclohexylcarbodiimide there were obtained, after chromatography on silica gel using System I for the elution, 132 mg of $N^1$-tert.butyl-$N^2$-[3(S)-[[N-[(1,2,3,4-tetrahydro-1-oxo-3(R or S)-isoquinolyl)carbonyl]-L-asparaginyl]amino]-2(R)-hydroxyphenylbutyl]-L-prolinamide (diastereomer A) as a white solid from methanol/diethyl ether, MS: m/e 621 [M+H]⁺, and 66 mg of $N^1$-tert.butyl-$N_2$-[3(S)-[[N-[(1,2,3,4-tetrahydro-1-oxo-3(R or S)-isoquinolyl)carbonyl]-L-asparaginyl]amino]-2(R)-hydroxy-4-phenylbutyl]-L-prolinamide (diastereomer B) as a white solid from methanol/diethyl ether; MS: m/e 621 [M+H]⁺.

EXAMPLE 60

In a manner analogous to that described in Example 27, from 418 mg of $N_2$-[3(S)-[[L-asparaginyl]amino]-2(R)-hydroxy-4-phenylbutyl]-$N^1$-tert.butyl-L-prolinamide, 218 mg of 2-acetamido-1,2,3,4-tetrahydro-2-naphthoic acid, 127 mg of hydroxybenzotriazole, 108 mg of N-ethylmorpholine and 212 mg of dicyclohexylcarbodiimide there were obtained, after chromatography on silica gel using dichloromethane/methanol (9:1) for the elution, 142 mg of $N_2$-[3(S)-[[N-[2(R or S)-acetamido-1,2,3,4-tetrahydro-2-naphthoyl]-L-asparaginyl]amino]-2(R)-hydroxy-4-phenylbutyl]-$N^1$-tert.butyl-L-prolinamide (diastereomer A) as a white solid, MS: m/e 663 [M+H]$^+$, and 80 mg of N$^2$-[3(S)-[[N-[2(R or S)-acetamido-1,2,3,4-tetrahydro-2-naphthoyl]-L-asparaginyl]amino]-2(R)-hydroxy-4-phenylbutyl]-N$^1$-tert.butyl-L-prolinamide (diastereomer B) as a white solid; MS: m/e 663 [M+H]$^+$.

EXAMPLE 61

In a manner analogous to that described in Example 27, from 209 mg of N$^2$-[3(S)-[[L-asparaginyl]amino]-2(R)-hydroxy-4-phenylbutyl]-N$^1$-tert.butyl-L-prolinamide, 81 mg of quinaldicacid, 63 mg of hydroxybenzotriazole, 54 mg of N-ethylmorpholine and 106 mg of dicyclohexylcarbodiimide there were obtained, after chromatography on silica gel using dichloromethane/methanol (9:1) for the elution, 88 mg of N$_2$-[2(R)-hydroxy-4-phenyl-3(S)-[[N-(2-quinolylcarbonyl)-L-asparaginyl]amino]butyl]-N$^1$-tert.butyl-L-prolinamide as a white solid; MS: m/e 603 [M+H]$^+$.

EXAMPLE 62

A solution of 844 mg of 1-[3(S)-amino-2(R)-hydroxy-4-phenylbutyl]-N-tert.butyl-2(S)-piperidinecarboxamide and 882 mg of N-(benzyloxycarbonyl)-L-asparagine succinimide ester in 25 ml of tetrahydrofuran was stirred at 20° C. for 16 hours and then evaporated. The residue was dissolved in 50 ml of dichloromethane and the organic solution was washed with saturated sodium chloride solution and water. The solvent was removed by evaporation and the residue was chromatographed on silica gel using dichloromethane/methanol (9:1) for the elution. There were obtained 461 mg of 1-[3(S)-[[N-(benzyloxycarbonyl)-L-asparaginyl]amino]-2(R)-hydroxy-4-phenylbutyl]-N-tert.butyl-2(S)-piperidinecarboxamide as a pale cream solid; MS: m/e 596 [M+H]$^+$.

The 1-[3(S)-amino-2(R)-hydroxy-4-phenylbutyl]-N-tert.butyl-2(S)-piperidinecarboxamide used as the starting material was prepared as follows:
(i) 2.576 g of N-tert.butyl-2(S)-piperidinecarboxamide and 4.158 g of 3(S)-(benzyloxyformamido)-1,2(S)-epoxy-4-phenylbutane in 70 ml of ethanol was heated at reflux for 16 hours. The solvent was removed by evaporation and the residue was dissolved in 100 ml of diethyl ether and treated with 10 g of activated magnesium silicate. The solvent was then removed by evaporation and there were obtained 6.16 g of 1-[3(S)l(benzyloxyformamido)-2(R)-hydroxy-4-phenylbutyl]-N-tert.butyl-2(S)-piperidinecarboxamide as a colourless glass; MS: m/e 482 [M+H]$^+$.
(ii) A solution of 1.25 g of 1-3(S)-(benzyloxyformamido)-2(R)-hydroxy-4-phenylbutyl]-N-tert.butyl-2(S)-piperidinecarboxamide in 80 ml of ethanol was hydrogenated over 10% palladium-on-carbon at 20° C. and under atmospheric pressure for 16 hours. The catalyst was removed by filtration and the filtrate was evaporated to give 0.844 g of 1-[3(S)-amino-2(R)-hydroxy-4-phenylbutyl]-N-tert.butyl-2(S)-piperidinecarboxamide as a pale yellow gum; MS: m/e 348 [M+H]$^+$.

EXAMPLE 63

In a manner analogous to that described in Example 21, from 226 mg of 1-[3(S)-[[L-asparaginyl]amino]-2(R)-hydroxy-4-phenylbutyl]-N-tert.butyl-2(S)-piperidinecarboxamide, 93 mg of 2-naphthoyl chloride and 63 mg of diisopropylethylamine there were obtained, after chromatography on silica gel using dichloromethane/methanol (9:1) for the elution, 76 mg of N-tert.butyl-1-[2(R)-hydroxy-3(S)-[[N-(2-naphthoyl)-L-asparaginyl]amino]-4-phenylbutyl]-2(S)-piperidinecarboxamide as a white solid; MS: m/e 616 [M+H]$^+$.

The 1-[3(S)-[[L-asparaginyl]amino]-2(R)-hydroxy-4-phenylbutyl]-N-tert.butyl-2(S)-piperidinecarboxamide used as the starting material was prepared by hydrogenating 1-[3(S)-amino-2(R)-hydroxy-4-phenylbutyl]-N-tert.butyl-2(S)-piperidinecarboxamide.

EXAMPLE 64

In a manner, analogous to that described in Example 27, from 226 mg of 1-[3(S)-[[L-asparaginyl]amino]-2(R)-hydroxy-4-phenylbutyl]-N-tert.butyl-2(S)-piperidinecarboxamide, 85 mg of quinaldic acid, 56 mg of N-ethylmorpholine, 66 mg of hydroxybenzotriazole and 111 mg of dicyclohexylcarbodiimide there were obtained, after chromatography on silica gel using dichloromethane/methanol (9:1) for the elution, 100 mg of N-tert.butyl 1-[2(R)-hydroxy-4-phenyl-3(S)-[[N-(2-quinolylcarbonyl)-L-asparaginyl]amino]butyl]-2(S)-piperidinecarboxamide as a white solid; MS: m/e 617 [M+H]$^+$.

EXAMPLE 65

In a manner analogous to that described in Example 27, from 228 mg of N$^2$-[3(S)-[[L-asparaginyl]amino]-2(R)-hydroxy-4-phenylbutyl]-N$^1$-tert.butyl-L-prolinamide, 88 mg of 3-isoquinolinecarboxylic acid, 69 mg of hydroxybenzotriazole, 59 mg of N-ethylmorpholine and 116 mg of dicyclohexylcarbodiimide there were obtained, after chromatography on silica gel using dichloromethane/methanol (9:1) for the elution, 88 mg of N$^1$-tert.butyl-N$_2$-[2(R)-hydroxy-3(S)-[[N-(3-isoquinolylcarbonyl)-L-asparaginyl]amino]-4-phenylbutyl]-L-prolinamide as a white solid; MS: m/e 603 [M+H]$^+$.

EXAMPLE 66

In a manner analogous to that described in Example 27, from 228 mg of N$_2$-[3(S)-[[L-asparaginyl]amino]-2(R)-hydroxy-4-phenylbutyl]-N$^1$-tert.butyl-L-prolinamide, 88 mg of 3-quinolinecarboxylic acid, 69 mg of hydroxybenzotriazole, 59 mg of N-ethylmorpholine and 116 mg of dicyclohexylcarbodiimide there were obtained, after chromatography on silica gel using dichloromethane/methanol (9:1) for the elution, 86 mg of N$^1$-tert.butyl-N$^2$-[2(R)-hydroxy-4-phenyl-3(S)-[[N-(3-quinolylcarbonyl)-L-asparaginyl]amino]butyl]-L-prolinamide as a white solid; MS: m/e 603 [M+H]$^+$.

EXAMPLE 67

In a manner analogous to that described in Example 27, from 295 mg of N$^2$-[3(S)-[[L-asparaginyl]amino]-2(R)-hydroxy-4-phenylbutyl]-N$^1$-tert.butyl-L-prolinamide, 214 mg of 3-(benzyloxyformamido)-2-naphthoic acid, 90 mg of hydroxybenzotriazole, 77 mg of N-ethylmorpholine and 151 mg of dicyclohexylcarbodiimide there were obtained, after chromatography on silica gel using System G for the elution, 380 mg of N$^2$-[3(S)-[[N-[3-(benzyloxyformamido)-2-naphthoyl]-L-asparaginyl]amino]-2(R)-hydroxy-4-phenylbutyl]-N$^1$-tert.butyl-L-prolinamide as a white solid from methanol; MS: m/e 751 [M+H]$^+$.

EXAMPLE 68

A solution of 216 mg of 1-[3(S)-amino-2(R)-hydroxy-4-phenylbutyl]-N-tert.butyl-2,3-dihydro-1H-indole-2(R or S)-carboxamide (diastereomer A), 151 mg of N-(benzyloxycarbonyl)-L-asparagine, 76 mg of hydroxybenzotriazole, 65 mg of N-ethylmorpholine and 128 mg of dicyclohexylcarbodiimide in 10 ml of tetrahydrofuran was stirred at 20° C. for 16 hours. The solvent was removed by evaporation and the residue was chromatographed on silica gel using dichloromethane/methanol (92:8) for the elution. There were obtained 70 mg of 1-[3(S)-[[N-(benzyloxycarbonyl)-L-asparaginyl]amino]-2(R)-hydroxy-4-phenylbutyl]-N-tert.butyl-2,3-dihydro-1H-indole-2 (R or S)-carboxamide (diastereomer A) as a pale cream solid; MS: m/e 630 [M+H]$^+$.

The 1-[3(S)-amino-2(R)-hydroxy-4-phenylbutyl]-N-tert.butyl-2,3-dihydro-1H-indole-2(R or S)-carboxamide used as the starting material was prepared as follows:

(i) A solution of 891 mg of N-tert.butyl-2,3-dihydro-1H-indole-2(R or S)-carboxamide and 654 mg of 3(S)-(benzyloxyformamido)-1,2(S)-epoxy-4-phenylbutane in 5 ml of dimethylformamide was heated to 140° C. for 40 hours. The solvent was removed by evaporation and the residue was chromatographed on silica gel using diethyl ether/n-hexane (2:1) for the elution. There were obtained 300 mg of 1-[3(S)-(benzyloxyformamido)-2(R)-hydroxy-4-phenylbutyl]-N-tert.butyl-2,3-dihydro-1H-indole-2(R or S)-carboxamide (diastereomer A) as a pale yellow oil, m/e 516 [M+H]$^+$, and 290 mg of 1-[3(S)-(benzyloxyformamido)-2(R)-hydroxy-4-phenylbutyl]-N-tert.butyl-2,3-dihydro-1H-indole-2(R or S)-carboxamide (diastereomer B) as a pale yellow oil; MS: m/e 516 [M+H]$^+$.

(ii) A solution of 300 mg of 1-[3(S)-(benzyloxyformamido)-2(R)-hydroxy-4-phenylbutyl]-N-tert.butyl-2,3-dihydro-1H-indole-2(R or S)-carboxamide (diastereomer A) in 20 ml of ethanol was hydrogenated over 10% palladium-on-carbon at 20° C. and under atmospheric pressure for 16 hours. The catalyst was removed by filtration and the filtrate was evaporated to give 216 mg of 1-[3(S)-amino-2(R)-hydroxy-4-phenylbutyl]-N-tert.butyl-2,3-dihydro-1H-indole-2(R or S)-carboxamide as a brownish oil.

EXAMPLE 69

In a manner analogous to that described in Example 68, from 223 mg of 1-[3(S)-amino-2(R)-hydroxy-4-phenylbutyl]-N-tert.butyl-2,3-dihydro-1H-indole-2(R or S)-carboxamide (diastereomer B), 151 mg of N-(benzyloxycarbonyl)-L-asparagine, 76 mg of hydroxybenzotriazole, 65 mg of N-ethylmorpholine and 128 mg of dicyclohexylcarbodiimide there were obtained 210 mg of 1-[3(S)-[[N-(benzyloxycarbonyl)-L-asparaginyl]amino]-2(R)-hydroxy-4-phenylbutyl]-N-tert.butyl-2,3-dihydro-1H-indole-2(R or S)-carboxamide (diastereomer B) as a pale cream solid; MS: m/e 630 [M+H]$^+$.

EXAMPLE 70

A solution of 0.422 g of $N_2$-[2(R)-hydroxy,4-phenyl-3(S)-[[N-(2-quinolylcarbonyl)-L-asparaginyl]amino]butyl]-$N^1$-tert.butyl-L-prolinamide and 142 mg of 3-chloroperbenzoic acid in 10 ml of dichloromethane was stirred at 20° C. for 1 hour. The solvent was then removed by evaporation and the residue was chromatographed on silica gel using dichloromethane/methanol (9:1) for the elution to give 289 mg of $N^1$-tert.butyl-$N_2$-[2(R)-hydroxy-4-phenyl-3(S)-[[N-(2-quinolylcarbonyl)-L-asparaginyl]amino]butyl]-L-prolinamide $N_2$-oxide as a white solid; MS: m/e 619 [M+H]$^+$.

EXAMPLE 71

A solution of 0.123 mg of $N^1$-tert.butyl-$N_2$-[2(R)-hydroxy-4-phenyl-3(S)-[[N-(2-quinolylcarbonyl)-L-asparaginyl]amino]butyl]-L-prolinamide $N_2$-oxide and 35 mg of 3-chloroperbenzoic acid in 5 ml of dichloromethane was stirred at 25° C. for 24 hours. A further 70 mg of 3-chloroperbenzoic acid was added and the mixture was stirred at 20° C. for 48 hours. The solution was washed with aqueous sodium carbonate solution and sodium chloride solution and the solvent was then removed by evaporation. The residue was chromatographed on silica gel using System J for the elution to give 70 mg of $N^1$-tert.butyl-$N^2$-[2(R)-hydroxy-3(S)-[[N-(1-oxido-2-quinolylcarbonyl)-L-asparaginyl]amino]-4-phenylbutyl]-L-prolinamide $N^2$-oxide as an off-white solid from ethyl acetate; MS: m/e 635 [M+H]$^+$.

EXAMPLE 72

A solution of 98 mg of 3-[3(S)-amino-2(R)-hydroxy-4-phenylbutyl]-N-tert.butyl-4(R)-thiazolidinecarboxamide dihydrobromide in 0.5 ml of dry dimethylformamide was stirred and cooled to −10° C. in an ice/salt bath while there were added 44 mg of N-ethylmorpholine followed by 76 mg of N-(benzyloxycarbonyl)-L-asparagine succinimide ester. The mixture was allowed to warm to room temperature and was then stirred overnight. Dimethylformamide was removed by evaporation under reduced pressure and the residue was dissolved in chloroform. The solution was washed with water, then dried over sodium sulphate and evaporated. The residual gum was purified by flash chromatography on silica gel using 4% methanol in dichloromethane for the elution. There were obtained 66 mg of 3-[3(S)-[[N-(benzyloxycarbonyl)-L-asparaginyl]amino]-2(R)-hydroxy-4-phenylbutyl]-N-tert.butyl-4(R)-thiazolidinecarboxamide as a colourless foam. Analytically pure product was obtained by recrystallization from ethyl acetate; MS: m/e 600 [M+H]$^+$.

The 3-[3(S)-amino-2(R)-hydroxy-4-phenylbutyl]-N-tert.butyl-4(R)-thiazolidinecarboxamide dihydrobromide used as the starting material was prepared as follows:

(i) A solution of 2.67 g of N-benzyloxycarbonyl-4(R)-thiazolidinecarboxylic acid in 42 ml of dry tetrahydrofuran was stirred and cooled to −15° C. in an ice/salt bath while there were added 1.15 g of N-ethylmorpholine followed after 2 minutes by 1.87 g of isobutyl chloroformate. After a further 3 minutes 0.73 g of tert.butylamine was added dropwise and the mixture was then allowed to warm to room temperature and was stirred overnight. Tetrahydrofuran was removed by evaporation under reduced pressure and the residue was dissolved in dichloromethane. The solution was washed in sequence with water, 10% citric acid solution, water, saturated sodium bicarbonate solution and water, then dried over anhydrous sodium sulphate, filtered and evaporated to give 2.85 g of 3-(benzyloxycarbonyl)-N-tert.butyl-4(R)-thiazolidinecarboxamide as a solid which melted at 96°–98° C. after recrystallization from diethyl ether/n-hexane.

(ii) A mixture of 3.2 g of 3-(benzyloxycarbonyl)-N-tert.butyl-4(R)-thiazolidinecarboxamide and 10 ml of 32% (w/w) hydrogen bromide in glacial acetic acid was stirred at room temperature for 2 hours. The resulting solution was poured into diethyl ether and the precipitated hydrobromide salt of the product was filtered off, washed with diethyl ether and then dissolved in water. The solution was made alkaline by the addition of 1M sodium hydroxide solution and extracted twice with dichloromethane. The combined dichloromethane extracts were washed with water, dried over anhydrous sodium sulphate, filtered and evaporated to give 1.57 g of N-tert.butyl-4(R)-thiazolidinecarboxamide as a crystalline solid of melting point 68°–71° C.

(iii) A solution of 3.2 g of N-tert.butyl-4(R)-thiazolidinecarboxamide and 5.0 g of 3(S)-(benzyloxyformamido)-1,2(S)-epoxy-4-phenylbutane in 130 ml of isopropanol was stirred under argon and heated at 90° C. under reflux for 3 days. The solution was evaporated under reduced pressure and the residue was purified by flash chromatography on silica gel using diethyl ethyl/n-hexane (2:1) for the elution. There were obtained 3.47 g of 3-[3(S)-(benzyloxyformamido)-2(R)-hydroxy-4-phenylbutyl]-N-tert.butyl-4(R)-thiazolidinecarboxamide. Recrystallization from ethyl acetate gave analytically pure material of melting point 62°–65° C.

(iv) A mixture of 2 g of 3-[3(S)-(benzyloxyformamido)-2(R)-hydroxy-4-phenylbutyl]-N-tert.butyl-4(R)-thiazolidinecarboxamide and 4.1 ml of 32% (w/w) hydrogen bromide in glacial acetic acid was stirred at room temperature for 1 hour. The resulting solution was diluted with anhydrous diethyl ether and the precipitated, product was rapidly filtered off and washed with fresh diethyl ether. There were obtained 2.01 g of 3-[3(S)-amino-2(R)-hydroxy-4-phenylbutyl]-N-tert.butyl-4(R)-thiazolidinecarboxamide dihydrobromide as a white solid; $^1$H NMR (300 MHz): $\delta(D_2O)$ 1.37 (9H, s), 3.0 (2H, m), 3.09 (2H, dq), 3.29 (2H, d), 3.85 (2H, m), 4.16 (1H, m), 4.3 (2H, q) and 7.42 (5H, m) ppm.

EXAMPLE 73

In a manner analogous to that described in Example 21, from 110 mg of 3-[3(S)-[[L-asparaginyl]amino]-2(R)-hydroxy-4-phenylbutyl]-N-tert.butyl-4(R)-thiazolidinecarboxamide, 46 mg of 2-naphthoyl chloride and 31 mg of diisopropylethylamine there were obtained, after flash chromatography on silica gel using 2% methanol in dichloromethane for the elution, 83 mg of N-tert.butyl-3-[2(R)-hydroxy-3(S)-[[N-(2-naphthoyl)-L-asparaginyl]amino]-4-phenylbutyl]-4(R)-thiazolidinecarboxamide; MS: m/e 620 $[M+H]^+$.

The 3-[3(S)-[[L-asparaginyl]amino]-2(R)-hydroxy-4-phenylbutyl]-N-tert.butyl-4(R)-thiazolidinecarboxamide used as the starting material was prepared as follows:

A mixture of 170 mg of 3-[3(S)-[[N-(benzyloxycarbonyl)-L-asparaginyl]amino]-2(R)-hydroxy-4-phenylbutyl]-N-tert.butyl-4(R)-thiazolidinecarboxamide and 0.3 ml of 32% (w/w) hydrogen bromide in glacial acetic acid was stirred at room temperature for 1 hour. The solution was diluted with diethyl ether and the precipitated solid was rapidly filtered off, washed with diethyl ether and dissolved in water. The solution was made alkaline by the addition of potassium carbonate and extracted with three portions of chloroform. The combined chloroform extracts were dried over anhydrous sodium sulphate, filtered and evaporated to give 110 mg of 3-[3(S)-[[L-asparaginyl]amino]-2(R)-hydroxy-4-phenylbutyl]-N-tert.butyl-4(R)-thiazolidinecarboxamide; MS: m/e 466 $[M+H]^+$.

EXAMPLE 74

A solution of 330 mg of $N^2$-[3(S)-[[N-(benzyloxycarbonyl)-L-asparaginyl]amino]-4-(4-tert.butoxyphenyl)-2(R)-hydroxybutyl]-$N^1$-tert.butyl-L-prolinamide in 30 ml of ethanol was hydrogenated over 50 mg of 10% palladium-on-carbon catalyst for 3 hours. The catalyst was removed by filtration and the filtrate was evaporated. The residue was dissolved in dichloromethane and treated with 72 mg of diisopropylethylamine and 106 mg of 2-naphthoyl chloride in a manner analogous to that described in Example 21 to give 165 mg of $N_2$-[4-(4-tert.butoxyphenyl)-2(R)-hydroxy-3(S)-[[N-(2-naphthoyl)-L-asparaginyl]amino]butyl]-$N^1$-tert.butyl-L-prolinamide as an off-white solid.

EXAMPLE 75

A solution of 90 mg of $N_2$-[4-(4-tert.butoxyphenyl)-2(R)-hydroxy-3(S)-[[N-(2-naphthoyl)-L-asparaginyl]amino]butyl]-$N^1$-tert.butyl-L-prolinamide in 40 ml of 3.5M hydrogen chloride in ethyl acetate was stirred at room temperature for 30 minutes. The solvent was removed by evaporation and the residue was triturated with diethyl ether and filteredto give 80 mg of $N_2$-[2(R)-hydroxy-4-(4-hydroxyphenyl)-3(S)-[[N-(2-naphthoyl)-L-asparaginyl]amino]butyl]-N-tert.-butyl-L-prolinamide hydrochloride as a white solid of melting point 171°–174° C.

EXAMPLE 76

A solution of 59 mg of 2-[3(S)-amino-2(R)-hydroxy-4-phenylbutyl]-N-tert.butyl-1,2,3,4-tetrahydropyrido[3,4-b]-indole-1-carboxamide (isomer A) and 71 mg of N-(benzyloxycarbonyl)-L-asparagine succinimide ester in 3 ml of dry tetrahydrofuran was stirred at room temperature for 16 hours and then evaporated. The residue was dissolved in of dichloromethane and the solution was washed twice with water and twice with saturated aqueous sodium bicarbonate solution. The solvent was removed by evaporation under reduced pressure to give 103 mg of crude product. 32 mg of this product were purified by reverse phase high pressure liquid chromatography using 55% 0.05M ammonium formate in acetonitrile for the elution. There were obtained 9.9 mg of 2-[3(S)-[[N-(benzyloxycarbonyl)-L-asparaginyl]amino]-2(R)-hydroxy-4-phenylbutyl]-N-tert.butyl-1,2,3,4-tetrahydropyrido[3,4-b]indole-1(R or S)-carboxamide (isomer A) as a colourless oil; MS: m/e 683 $[M+H]^+$.

2-[3(S)-[[N-(Benzyloxycarbonyl)-L-asparaginyl]amino]-2(R)-hydroxy-4-phenylbutyl]-N-tert.butyl-1,2,3,4-tetrahydropyrido[3,4-b]indole-1-carboxamide (isomer B) was prepared from 2-[3(S)-amino-2(R)-hydroxy-4-phenylbutyl-N-tert.butyl-1,2,3,4-tetrahydropyrido[3,4-b]indole-1(R or S)-carboxamide (isomer B) in a manner analogous to isomer A above and was purified in the same manner to give a colourless oil; MS: m/e 683 $[M+H]^+$.

The 2-[3(S)-amino-2(R)-hydroxy-4-phenylbutyl]-N-tert.-butyl-1,2,3,4-tetrahydropyrido[3,4-b]indole-1-carboxamides used as the starting materials were prepared as follows:

(i) To a solution, cooled in ice, of 3.0 g of 1,2,3,4-tetrahydropyrido[3,4-b]indole-1-carboxylic acid in 7 ml of 2M sodium hydroxide solution, 17 ml of water and 17 ml of dioxan were added in alternating portions 12.5 ml of 2M sodium hydroxide solution and a solution of 3.6 ml of benzyl chloroformate in 9 ml of dioxan. After completion of the additions the mixture was stirred at room temperature overnight and the dioxan-was then removed by evaporation under reduced pressure. The solution obtained was diluted with water, washed twice with diethyl ether, acidified with 25 ml of 1M sulphuric acid and extracted three times with ethyl acetate. The organic extracts were combined, washed twice with water, dried over anhydrous magnesium sulphate and evaporated to give 4.54 g of 2-benzyloxycarbonyl-1,2,3,4-tetrahydropyrido[3,4-b]indole-1-carboxylic acid, MS: m/e 351 $[M+H]^+$, which was used without purification.

(ii) A solution of 4.54 g of 2-benzyloxycarbonyl-1,2,3,4-tetrahydropyrido[3,4-b]indole-1-carboxylic acid in 45 ml of anhydrous tetrahydrofuran was cooled, while protecting with a drying tube, in an ice/acetone bath. 1.82 ml of N-ethylmorpholine and 1.82 ml of isobutyl chloroformate were added, the mixture was stirred for 10 minutes and then 2.1 ml of tert.butylamine were added. The mixture was then stirred at 0° C. for 40 minutes and at room temperature for 45 minutes, diluted with ethyl acetate and washed twice with water, twice with 0.5M sodium hydroxide solution and again with water. The solution was dried over magnesium sulphate and evaporated to dryness. Recrystallization from ethyl acetate and n-hexane gave 1.21 g of tert.butyl 2-benzyloxycarbonyl-1,2,3,4-tetrahydropyrido-[3,4-b]indole-1-carboxamide; MS: m/e 406 [M+H]⁺. A further 0.76 g of identical material was obtained by subjecting the mother liquors to chromatography on silica gel using ethyl acetate/n-hexane (1:1) for the elution.

(iii) 1.62 g of tert.butyl-benzyloxycarbonyl-1,2,3,4-tetrahydropyrido[3,4-b]indole-1-carboxamide were dissolved in 10 ml of a 45% solution of hydrogen bromide in acetic acid. After 30 minutes the solution was evaporated and the residue was taken up in water. After filtration the filtrate was washed three times with diethyl ether and then neutralized by the addition of saturated aqueous sodium bicarbonate solution. The product was extracted from the now turbid aqueous layer with ethyl acetate. The combined organic extracts were dried over anhydrous magnesium sulphate and evaporated to give 0.84 g of tert.butyl 1,2,3,4-tetrahydropyrido[3,4-b]indole-1-carboxamide as a white crystalline solid of melting point 144° C.

(iv) A solution of 0.60 g of tert.butyl 1,2,3,4-tetrahydropyrido[3,4-b]indole-1-carboxamide and 0.66 g of 3(S)-(benzyloxyformamido)-1,2(S)-epoxy-4-phenylbutane in 20 ml of methanol was heated at reflux under argon for 16 hours and then evaporated to give a clear oil. The two diastereomeric products were separated by flash chromatography on silica gel using n-hexane/ethyl acetate (3:1) for the elution. There were obtained 268 mg of isomer A of 2-[3(S)-(benzyloxyformamido)-2(R)-hydroxy-4-phenylbutyl]-N-tert.butyl-1,2,3,4-tetrahydropyrido[3,4-b]indole-1-carboxamide, MS: m/e 569 [M+H]⁺, and 65 mg of isomer B of the same compound; MS: m/e 569 [M+H]⁺.

(v) A solution of 150 mg of 2-[3(S)-(benzyloxyformamido)-2(R)-hydroxy-4-phenylbutyl]-N-tert.butyl-1,2,3,4-tetrahydropyrido[3,4-b]indole-1-carboxamide (isomer A) in 5 ml of ethanol was hydrogenated under a pressure of 3.4 atmospheres over 10% palladium-on-charcoal at 20° C. for 16 hours. The catalyst was removed by filtration and the filtrate was evaporated to give 120 mg of 2-[3(S)-amino-2(R)-hydroxy-4-phenylbutyl]-N-tert.butyl-1,2,3,4-tetrahydropyrido[3,4-b]indole-1-carboxamide (isomer A); MS: m/e 435 [M+H]⁺.

2-[3(S)-Amino-2(R)-hydroxy-4-phenylbutyl]-N-tert.butyl-1,2,3,4-tetrahydropyrido[3,4-b]indole-1-carboxamide (isomer B) MS: m/e 435 [M+H]⁺, was prepared in an analogous manner from 2-[3(S)-(benzyloxyformamido)-2(R)-hydroxy-4-phenylbutyl]-N-tert.butyl-1,2,3,4-tetrahydropyrido[3,4-b]indole-1-carboxamide (isomer B).

EXAMPLE 77

In a manner analogous to that described in Example 70, from 154 mg of N-tert.butyl-1-[2(R)-hydroxy-3(S)-[[N-(2-quinolylcarbonyl)-L-asparaginyl]amino-4-phenylbutyl]-2(S)-piperidinecarboxamide and 51 mg of 3-chloroperbenzoic acid there were obtained 114 mg of N-tert.butyl-1-[2(R)-hydroxy-4-phenyl-3(S)-[[N-(2-quinolylcarbonyl)-L-asparaginyl]amino]butyl]-2-piperidinecarboxamide 1-oxide as a white solid; MS: m/e 633 [M+H]⁺.

EXAMPLE 78

In a manner analogous to that described in Example 27, from 230 mg of 1-[3(S)-[[L-asparaginyl]amino]-2(R)-hydroxy-4-phenylbutyl]-N-tert.butyl-2(S)-piperidinecarboxamide, 139 mg of 3-benzyloxy-2-naphthoic acid, 113 mg of dicyclohexylcarbodiimide, 68 mg of hydroxybenzotriazole and 58 mg of N-ethylmorpholine there were obtained, after chromatography on silica gel using System G for the elution, 242 mg of 1-[3(S)-[[N-(3-benzyloxy-2-naphthoyl)-L-asparaginyl]amino]-2(R)-4-phenylbutyl]-N-tert.butyl-2(S)-piperidinecarboxamide as a foam; MS: m/e 722 [M+H]⁺.

EXAMPLE 79

A solution of 181 mg of 1-[3(S)-[[N-(3-benzyloxy-2-naphthoyl)-L-asparaginyl]amino]-2(R)-hydroxy-4-phenylbutyl]-N-tert.butyl-2(S)-piperidinecarboxamide in 5 ml of ethanol was hydrogenated over 10% palladium-on-carbon at 20° C. and under atmospheric pressure for 16 hours. The catalyst was removed by filtration and the filtrate was evaporated. After trituration with diethyl ether there were obtained 110 mg of N-tert.butyl-1-[3(S)-[[N-(3-hydroxy-2-naphthoyl)-L-asparaginyl]amino]-2(R)-hydroxy-4-phenylbutyl]-2(S)-piperidinecarboxamide as a pale yellow solid; MS: m/e 632 [M+H]⁺.

EXAMPLE 80

In a manner analogous to that described in Example 27, from 400 mg of cis-1-[3(8)-amino-2(R)-hydroxy-4-phenylbutyl]-N-tert.butyl-decahydro-2(R or S)-quinolinecarboxamide, 266 mg of N-(benzyloxycarbonyl)-L-asparagine, 226 mg of dicyclohexylcarbodiimide, 135 mg of hydroxybenzotriazole and 115 mg of N-ethylmorpholine there were obtained, after chromatography on silica gel using dichloromethane/methanol (94:6) for the elution, 225 mg of cis-1-[3(S)-[[N-(benzyloxycarbonyl)-L-asparaginyl]amino]-2(R)-hydroxy-4-phenylbutyl]-N-tert.butyl-decahydro-2(R or S)-quinolinecarboxamide as a white solid; MS: m/e 650 [M+H]⁺.

The cis-1-[3(S)-amino-2(R)-hydroxy-4-phenylbutyl]-N-tert.butyl-decahydro-2(R or S)-quinolinecarboxamide used as the starting material was prepared as follows:

(i) A solution of 2.376 g of 3(S)-(benzyloxyformamido)-1,2(S)-epoxy-4-phenylbutane and 1.904 g of cis-N-tert.butyl-decahydro-2(R,S)-quinolinecarboxamide in 32 ml of ethanol was stirred at 80° C. for 24 hours. A further 0.474 g of 3(S)-(benzyloxyformamido)-1,2(S)-epoxy-4-phenylbutane was added in two portions and the mixture was stirred at 80° C. for a further 5 hours. The solvent was removed by evaporation and the residue was chromatographed on silica gel using dichloromethane/methanol (97.5:2.5) for the elution to give 1.17 g of cis-1-[3(S)-(benzyloxyformamido)-2(R)-hydroxy-4-phenylbutyl]-N-tert.butyl-decahydro-2(R or S)-quinolinecarboxamide (isomer A) as a white solid from diethyl ether/n-hexane, MS: m/e 536 [M+H]⁺, and 1.146 g of cis-1-[3(S)-(benzyloxyformamido)-2(R)-hydroxy-4-phenylbutyl]-N-tert.butyl-decahydro-2(R or S)-quinolinecarboxamide (isomer B) as a pale yellow gum; MS: m/e 536 [M+H]⁺.

(ii) A solution of 0.535 g of cis-1-[3(S)-(benzyloxyformamido)-2(R)-hydroxy-4-phenylbutyl]-N-tert.butyl-decahydro-2(R or S)-quinolinecarboxamide (isomer B) in 25 ml of ethanol was hydrogenated over 10% palladium-on-carbon at 20° C. and under atmospheric pressure for 16 hours. The catalyst was removed by filtration and the filtrate was evaporated to give 400 mg of cis-1-[3(S)-amino-2(R)-hydroxy-4-phenylbutyl]-N-tert.butyl-decahydro-2(R or S)-quinolinecarboxamide as a colourless gum.

EXAMPLE 81

A solution of 561 mg of trans-2-[3(S)-amino-2(R)-hydroxy-4-phenylbutyl]-N-tert.butyl-decahydro-(4aR,8aS)-isoquinoline-3(S)-carboxamide and 372 mg of N-(benzyloxycarbonyl)-L-asparagine in 20 ml of dry tetrahydrofuran is cooled in an ice/salt mixture. 189 mg of hydroxybenzotriazole, 161 mg of N-ethylmorpholine and 317 mg of dicyclohexylcarbodiimide are added and the mixture is stirred for 16 hours. The mixture is then diluted with ethyl acetate and filtered. The filtrate is washed with aqueous sodium bicarbonate solution and sodium chloride solution. The solvent is removed by evaporation and the residue is chromatographed on silica gel using dichloromethane/methanol (9:1) for the elution to give trans-2-[3(S)-[[N-(benzyloxycarbonyl)-L-asparaginyl]amino]-2(R)-hydroxy-4-phenylbutyl]-N-tert.butyl-decahydro-(4aR,8aS)-isoquinoline-3(S)-carboxamide.

The trans-2-[3(S)-amino-2(R)-hydroxy-4-phenylbutyl]-N-tert.butyl-decahydro-(4aR,8aS)-isoquinoline-3(S)-carboxamide used as the starting material is prepared as follows:

(i) A solution of 440 mg of trans-N-tert.butyl-decahydro-(4aR,8aS)-isoquinoline-3(S)-carboxamide and 549 mg of 3(S)-(benzyloxyformamido)-1,2(S)-epoxy-4-phenylbutane in 6 ml of ethanol is stirred at 60° C. for 7 hours. A further 54 mg of 3(S)-(benzyloxyformamido)-1,2(S)-epoxy-4-phenylbutane are added and the solution is stirred at 20° C. for 16 hours. The solvent is removed by evaporation and the residue is chromatographed on silica gel using system H for the elution to give trans-2-[3(S)-(benzyloxyformamido)-2(R)-hydroxy-4-phenylbutyl-N-tert.butyldecahydro-(4aR,8aS)-isoquinoline-3(S)-carboxamide.

(ii) A solution of 747 mg of trans-2-[3(S)-(benzyloxyformamido)-2(R)-hydroxy-4-phenylbutyl-N-tert.butyl-decahydro-(4aR,8aS)-isoquinoline-3(S)-carboxamide in 40 ml of ethanol is hydrogenated over 10% palladium-on-carbon at 20° C. and under atmospheric pressure for 5 hours. The catalyst is removed by filtration and the filtrate is evaporated to give trans-2-[3(S)-amino-2(R)-hydroxy-4-phenylbutyl]-N-tert.butyl-decahydro-(4aR,8aS)-isoquinoline-3(S)-carboxamide as a buff coloured solid.

EXAMPLE 82

In a manner analogous to that described in Example 27, from 276 mg of 1-[3(S)-[[L-asparaginyl]amino]-2(R)-hydroxy-4-phenylbutyl]-N-tert.butyl-2(S)-piperidinecarboxamide, 167 mg of 1-benzyloxy-2-naphthoic acid, 81 mg of hydroxybenzotriazole, 69 mg of N-ethylmorpholine and 136 mg of dicyclohexylcarbodiimide there were obtained, after chromatography on silica gel using dichloromethane/methanol (9:1) for the elution, 97 mg of 1-[3(S)-[[N-(1-benzyloxy-2-naphthoyl)-L-asparaginyl]amino]-2(R)-hydroxy-4-phenylbutyl]-N-tert.butyl-2(S)-piperidinecarboxamide as a white solid from methanol/diethyl ether: MS: m/e 722 [M+H]$^+$.

EXAMPLE 83

In a manner analogous to that described in Example 79, from 119 mg of 1-[3(S)-[[N-(1-benzyloxy-2-naphthoyl)-L-asparaginyl]amino]-2(R)-hydroxy-4-phenylbutyl]-N-tert.butyl-2(S)-piperidinecarboxamide there were obtained, after chromatography on activated magnesium silicate using dichloromethane/methanol (9:1) for the elution, 67 mg of N-tert.butyl-1-[2(R)-hydroxy-3(S)-[[N-(1-hydroxy-2-naphthoyl)-L-asparaginyl]amino]-4-phenylbutyl]-2(S)-piperidinecarboxamide as a white solid; MS: m/e 631 [M+H]$^+$.

EXAMPLE 84

In a manner analogous to that described in Example 27, from 276 mg of 1-[3(S)-[[L-asparaginyl]amino]-2(R)-hydroxy-4-phenylbutyl]-N-tert.butyl-2(S)-piperidinecarboxamide, 183 mg of 3-(benzyloxycarbonyl)-2-naphthoic acid, 81 mg of hydroxybenzotriazole, 138 mg of N-ethylmorpholine and 136 mg of dicyclohexylcarbodiimide there were obtained, after chromatography on silica gel using System J for the elution, 98 mg of N-tert.butyl-1-[3(S)-[1(S)-(2,3-dihydro-1,3-dioxo-1H-benz[f]isoindol-2-yl)-3-carbamoyl-propionamido]-2(R)-hydroxy-4-phenylbutyl]-2(S)-piperidinecarboxamide; MS: m/e 642 [M+H]$^+$.

EXAMPLE 85

A solution of 650 mg of N$^2$-[3(S)-amino-2(R)-hydroxy-4-phenylbutyl]-N$^1$-tert.butyl-L-prolinamide and 538 mg of N-(benzyloxycarbonyl)-S-methyl-L-cysteine in 20 ml of dry tetrahydrofuran was cooled in an ice/salt mixture. 270 mg of hydroxybenzotriazole, 230 mg of N-ethylmorpholine and 412 mg of dicyclohexylcarbodiimide were added and the mixture was stirred for 16 hours. The mixture was diluted with ethyl acetate and filtered. The filtrate was washed with aqueous sodium bicarbonate solution and sodium chloride solution. The solvent was removed by evaporation and the residue was chromatographed on silica gel using System G for the elution to give 800 mg of N$_2$-[3(S)-[N-(benzyloxycarbonyl)-S-methyl-L-cysteinyl]amino]-2(R)-hydroxy-4-phenylbutyl]-N$^1$-tert.butyl-L-prolinamide; MS: m/e 585 [M+H]$^+$.

The N$^2$-[3(S)-amino-2(R)-hydroxy-4-phenylbutyl]-N$^1$-tert.butyl-L-prolinamide used as the starting material was prepared in an analogous manner to the starting material of Example 33, but using N$^1$-tert.butyl-L-prolinamide in paragraph (iii) in place of N$^1$-phenyl-L-prolinamide.

EXAMPLE 86

A solution of 193 mg of N$^2$-[3(S)-[[N-(benzyloxycarbonyl)-S-methyl-L-cysteinyl]amino]-2(R)-hydroxy-4-phenyl-butyl]-N$^1$-tert.butyl-L-prolinamide in 2 ml of methanol was cooled to −70° C. A solution of 62 mg of 3-chloroperbenzoic acid in 5 ml of methanol was added and the mixture was stirred at −70° C. for 30 minutes. The solvent was then removed by evaporation and the residue was chromatographed on silica gel using System G for the elution to give 62 mg of N$_2$-[3(S)-[[N-(benzyloxycarbonyl)-3-(methylsulphinyl)-L-alanyl]amino]-2(R)-hydroxy-4-phenylbutyl]-N$^1$-tert.butyl-L-prolinamide as a 1:1 mixture of diastereomers; MS: m/e 601 [M+H]$^+$.

EXAMPLE 87

A solution of 450 mg of N$^2$-[3(S)-[[N-(benzyloxycarbonyl)-S-methyl-L-cysteinyl]amino]-2(R)-hydroxy-4-phenyl-butyl]-N$^1$-tert.butyl-L-prolinamide in 4 ml of methanol was cooled to −70° C. 166 mg of 3-chloroperbenzoic acid were added portionwise over a period of 10 minutes, the solution was stirred at −70° C. for 15 minutes and then allowed to warm to 20° C. The solution was again cooled to −70° C., a further 33 mg of 3-chloroperbenzoic acid were added and the mixture was stirred at −70° C. for 30 minutes. The solvent was removed by evaporation and the residue was partitioned between dichloromethane and 2N sodium hydroxide solution. The organic phase was evaporated and the residue was chromatographed on silica gel using System G for the elution to give 100 mg of N$^2$-[3(S)-[[N-(benzyloxycarbonyl)-3-(methylsulphinyl)-L-alanyl]amino]-2(R)-hydroxy-4-phenylbutyl]-N-tert.butyl-L-prolinamide N$_2$-oxide (diastereomer A), MS: m/e 617 [M+H]$^+$, and 154 mg of N$^2$-[3(S)-[[N-(benzyloxycarbonyl)-3-(methylsulphinyl)-L-alanyl]amino]-2(R)-hydroxy-4-phenylbutyl]-N$^1$-tert.butyl-L-prolinamide N$_2$-oxide (diastereomer B); MS: m/e 617 [M+H]$^+$.

EXAMPLE 88

A solution of 154 mg of $N^2$-[3(S)-[[N-(benzyloxycarbonyl)-3-(methylsulphinyl)-L-alanyl]amino]-2(R)-hydroxy-4-phenylbutyl]-$N^1$-tert.butyl-L-prolinamide $N^2$-oxide (two diastereomers) in 5 ml of methanol was treated with 84 mg of 3-chloroperbenzoic acid and the solution was stirred at 20° C. for 16 hours. The solvent was removed by evaporation and the residue was partitioned between dichloromethane and 2M sodium hydroxide solution. The organic phase was evaporated and the residue was crystallized from ethyl acetate/n-hexane to give 28 mg of $N^2$-[3(S)-[[N-(benzyloxycarbonyl)-3-(methylsulphonyl)-L-alanyl]amino]-2(R)-hydroxy-4-phenylbutyl]-$N^1$-tert.butyl-L-prolinamide $N_2$-oxide monohydrate; MS: m/e 633 $[M+H]^+$.

EXAMPLE 89

In a manner analogous to that described in Example 27, from 400 mg of cis-1-[3(S)-amino-2(R)-hydroxy-4-phenylbutyl]-N-tert.butyl-decahydro-2(R or S)-quinolinecarboxamide, 266 mg of N-(benzyloxycarbonyl)-L-asparagine, 226 mg of dicyclohexylcarbodiimide, 135 mg of hydroxybenzotriazole and 115 mg of N-ethylmorpholine there were obtained, after chromatography on silica gel using dichloromethane/methanol (94:6) for the elution, 225 mg of cis-1-[3(S)-[[N-(benzyloxycarbonyl)-L-asparaginyl]amino]-2(R)-hydroxy-4-phenylbutyl]-N-tert.butyl-decahydro-2(R or S)-quinolinecarboxamide as a white solid; MS: m/e 650 $[M+H]^+$.

The cis-1-[3(S)-amino-2(R)-hydroxy-4-phenylbutyl]-N-tert.butyl-decahydro-2(R or S)-quinolinecarboxamide used as the starting material was prepared as follows:
(i) A solution of 2.376 g of 3(S)-(benzyloxyformamido)-1,2(S)-epoxy-4-phenylbutane and 1.904 g of cis-N-tert.butyl-decahydro-2(R,S)-quinolinecarboxamide in 32 ml of ethanol was stirred at 80° C. for 24 hours. A further 0.474 g of 3(S)-(benzyloxyformamido)-1,2(S)-epoxy-4-phenylbutane was added in two portions and the mixture was stirred at 80° C. for a further 5 hours. The solvent was removed by evaporation and the residue was chromatographed on silica gel using dichloromethane/methanol (97.5:2.5) for the elution to give 1.17 g of cis-1-[3(S)-(benzyloxyformamido)-2(R)-hydroxy-4-phenylbutyl]-N-tert.butyl-decahydro-2(R or S)-quinolinecarboxamide (isomer A) as a white solid from diethyl ether/n-hexane, MS: m/e 536 $[M+H]^+$, and 1.146 g of cis-1-[3(S)-(benzyloxyformamido)-2(R)-hydroxy-4-phenylbutyl]-N-tert.butyl-decahydro-2(R or S)-quinolinecarboxamide (isomer B) as a pale yellow gum; MS: m/e 536 $[M+H]^+$.
(ii) A solution of 0.535 g of cis-1-[3(S)-(benzyloxyformamido)-2(R)-hydroxy-4-phenylbutyl]-N-tert.butyl-decahydro-2(R or S)-quinolinecarboxamide (isomer B) in 25 ml of ethanol was hydrogenated over 10% palladium-on-carbon at 20° C. and under atmospheric pressure for 16 hours. The catalyst was removed by filtration and the filtrate was evaporated to give 400 mg of cis-1-[3(S)-amino-2(R)-hydroxy-4-phenylbutyl]-N-tert.butyl-decahydro-2(R or S)-quinolinecarboxamide as a colourless gum.

EXAMPLE 90

In a manner analogous to that described in Example 27, from 27 mg of N-[3(S)-[[L-asparaginyl]amino]-2(R)-hydroxy-4-phenylbutyl]-L-proline tert.butyl ester and 11.3 mg of 2-indolecarboxylic acid there were obtained 15 mg of N-[3(S)-[[N-(2-indolylcarbonyl)-L-asparaginyl]amino]-2(R)-hydroxy-4-phenylbutyl]-L-proline tert.butyl ester; MS: m/e 592 $[M+H]^+$.

EXAMPLE 91

In a manner analogous to that described in Example 72, from 240 mg of 3-[3(S)-amino-2(R)-hydroxy-4-phenylbutyl]-N-tert.butyl-tetrahydro-2H-1,3-thiazine-4(R and S)-carboxamide and 234 mg of N-(benzyloxycarbonyl)-L-asparagine succinimide ester there were obtained 162 mg of 3-[3(S)-[[N-(benzyloxycarbonyl)-L-asparaginyl]amino]-2(R)-hydroxy-4-phenylbutyl]-N-tert.butyl-tetrahydro-2H-1,3-thiazine-4(R and S)-carboxamide as a mixture of two diastereomers. Flash chromatography on silica gel using 3% methanol in dichloromethane for the elution gave 20 mg of the less polar diastereomer (isomer A), MS: m/e 614 $[M+H]^+$, and using 5% methanol in dichloromethane gave 32 mg of the more polar diastereomer (isomer B): MS: m/e 614 $[M+H]^+$.

The 3-[3(S)-amino-2(R)-hydroxy-4-phenylbutyl]-N-tert.butyl-tetrahydro-2H-1,3-thiazine-4(R and S)-carboxamide used as the starting material was prepared from the known tetrahydro-2H-1,3-thiazine-4(R and S)-carboxylic acid by N-benzyloxycarbonylation in a known manner, subsequent reaction in a manner analogous to that described in Example 72(i)–(iv) and basification of the dihydrobromide obtained with sodium bicarbonate solution.

EXAMPLE 92

0.122 g of N-(benzyloxycarbonyl)-3-cyano-L-alanine was dissolved in 2 ml of dry dimethyformamide. The solution was stirred and cooled in an ice/salt bath and treated with 0.066 g of hydroxybenzotriazole and 0.1 g of dicyclohexylcarbodiimide. The mixture was stirred for 5 minutes and then treated with 0.163 g of $N_2$-[3(S)-amino-2(R)-hydroxy-4-phenylbutyl]-$N^1$-tert.butyl-L-prolinamide in 2.5 ml of dry dichloromethane. The mixture was allowed to warm to room temperature and was then stirred overnight. The resulting dicyclohexylurea was filtered off and washed with methylene chloride. The combined filtrate and washings were evaporated at 40° C. in a vacuum to give an oil which was partitioned between ethyl acetate and water. The organic phase was washed in sequence with saturated aqueous sodium bicarbonate solution and saturated sodium chloride solution and then dried over sodium sulphate. The solvent was removed by evaporation to give an oil which was chromatographed on silica gel using 14% methanol in dichloromethane for the elution. There were thus obtained 50 mg of product which was recrystallized from diethyl ether/n-hexane to give 0.045 g of $N^2$-[3(S)-[[N-(benzyloxycarbonyl)-3-cyano-L-alanyl]amino]-2(R)-hydroxy-4-phenylbutyl]-$N^1$-tert.butyl-L-prolinamide hemihydrate as a solid of melting point 65°–70° C. (softening).

The $N^2$-[3(S)-amino-2(R)-hydroxy-4-phenylbutyl]-$N^1$-tert.butyl-L-prolinamide used as the starting material was prepared as follows:
(i) A solution of 0.425 g of 3(S)-(benzyloxyformamido)-1,2(S)-epoxy-4-phenylbutane and 0.244 g of L-proline tert.butylamide in 10 ml of dry isopropanol was heated at 80° C. for 20 hours. The solvent was removed by evaporation in a vacuum and the residue was chromatographed on silica gel using 5% methanol in dichloromethane for the elution. There was obtained 0.44 g of $N^2$-[3(S)-(benzyloxyformamido)-2(R)-hydroxy-4-phenylbutyl]-$N^1$-tert.butyl-L-prolinamide as a white foam.
(ii) A solution of 0.46 g of $N^2$-[3(S)-(benzyloxyformamido)-2(R)-hydroxy-4-phenylbutyl]-$N^1$-tert.butyl-L-prolinamide in 40 ml of ethanol was hydrogenated over 40 mg of 10% palladium-on-carbon at room temperature and under atmospheric pressure for 1.5 hours to give 0.33 g of N$_2$-[3(S)-amino-2(R)-hydroxy-4-phenylbutyl]-N$^1$-tert.butyl-L-prolinamide as a gum which crystallized on standing.

EXAMPLE 93

0.167 g of N$^2$-[3(S)-amino-2(R)-hydroxy-4-phenylbutyl]-N$^1$-tert.butyl-L-prolinamide was dissolved in 10 ml of dry dimethylformamide and the solution was stirred at 0° C. while 0.191 g of the N-(benzyloxycarbonyl)-L-phenylglycine succinimide ester was added as a solid. The solution obtained was stirred at 0° C. for 1 hour and then stored at 4° C. overnight. The solution was then evaporated in a vacuum and the residue was partitioned between ethyl acetate and water. The organic phase was washed with saturated aqueous sodium bicarbonate solution and then with saturated sodium chloride solution. The aqueous phases were back-extracted with ethyl acetate. The combined organic phases were dried over sodium sulphate and evaporated to give a gum which was chromatographed on silica gel using acetone/dichloromethane (1:1) for the elution. The combined product-containing fractions were evaporated to give a gum which was re-evaporated with diethyl ether to give 0.127 g of a solid. This solid was extracted with dichloromethane and the combined organic phases were evaporated to give a solid which was triturated with diethyl ether. There was thus obtained 0.05 g of N$_2$-[3(S)-[[N-(benzyloxycarbonyl)-L-phenylglycyl]amino]-2(R)-hydroxy-4-phenylbutyl]-N$^1$-tert.butyl-L-prolinamide as a solid of melting point 101°–103° C.

EXAMPLE 94

In a manner analogous to that described in Example 92, from 0.15 g of N-(benzyloxycarbonyl)-L-phenylalanine, 0.066 g of hydroxybenzotriazole, 0.1 g of dicyclohexylcarbodiimide and 0.166 g of N$^2$-[3(S)-amino-2(R)-hydroxy-4-phenylbutyl]-N$^1$-tert.butyl-L-prolinamide there was obtained 0.1 g of N$^2$-[3(S)-[N-(benzyloxycarbonyl)-L-phenylalanyl]amino]-2(R)-hydroxy-4-phenylbutyl]-N$^1$-tert.butyl-L-prolinamide as a white solid of melting point 78°–80° C.

EXAMPLE 95

In a manner analogous to that described in Example 92, from 0.152 g of N-(benzyloxycarbonyl)-3-cyclohexyl-L-alanine, 0.066 g of hydroxybenzotriazole, 0.1 g of dicyclohexylcarbodiimide and 0.166 g of N$^2$-[3(S)-amino-2(R)-hydroxy-4-phenylbutyl]-N$^1$-tert.butyl-L-prolinamide there was obtained 0.1 g of N$^2$-[3(S)-[[N-(benzyloxycarbonyl)-3-cyclohexyl-L-alanyl]amino]-2(R)-hydroxy-4-phenylbutyl]-N$^1$-tert.butyl-L-prolinamide of melting point 71°–75° C.

EXAMPLE 96

In a manner analogous to that described in Example 92, from 0.1 g of N-(benzyloxycarbonyl)-L-asparagine, 0.05 g of hydroxybenzotriazole, 0.078 g of dicyclohexylcarbodiimide and 0.17 g of 1-[3(S)-amino-2(R)-hydroxy-4-phenylbutl]-4-(tert.butoxycarbonyl)-N-tert.butyl-2(R and S)-piperazinecarboxamide there was obtained, after trituration with diethyl ether, 0.11 g of a white solid. This solid was purified by flash chromatography on silica gel using 10% methanol in dichloromethane for the elution. The first product eluted (isomer A) was 0.043 g of 1-[3(S)-[[N-(benzyloxycarbonyl)-L-asparaginyl]amino]-2(R)-hydroxy-4-phenylbutyl]-4-(tert.butoxycarbonyl)-N-tert.butyl-2(R or S)-piperazinecarboxamide; MS: m/e 697 [M+H]$^+$. The second product eluted (isomer B) was 0.007 g of 1-[3(S)-[[N-(benzyloxycarbonyl)-L-asparaginyl]amino]-2(R)-hydroxy-4-phenylbutyl]-4-(tert.butoxycarbonyl)-N-tert.butyl-2(R or S)-piperazinecarboxamide; MS: m/e 697 [M+H]$^+$.

The 1-[3(S)-amino-2(R)-hydroxy-4-phenylbutyl]-4-(tert.-butoxycarbonyl)-N-tert.butyl-2(R and S)-piperazinecarboxamide used as the starting material was prepared as follows:

(i) 0.65 g of 2-piperazinecarboxylic acid was dissolved in a mixture of 5 ml of water and 5 ml of dioxane, treated with 0.42 g of sodium bicarbonate and stirred for 5 minutes. 1.09 g of di(-tert.butyl) dicarbonate were added and the mixture was stirred overnight. The mixture was concentrated by evaporation and the residue was extracted exhaustively with ethyl acetate. This procedure was repeated at pH 6 and pH 4. The aqueous layer, pH 4, was then extracted with n-butanol. The combined organic extracts were dried over anhydrous sodium sulphate and evaporated to give 0.34 g of 4-(tert.butoxycarbonyl)-2-piperazinecarboxylic acid as a cream coloured solid of melting point 226°–229° C.

(ii) 0.1 g of 4-(tert.butoxycarbonyl)-piperazine-2-carboxylic acid was dissolved in 10 ml of 1N sodium hydroxide solution, cooled to 0° C. and treated with 0.2 g of benzyl chloroformate. The mixture was allowed to warm to room temperature and was then stirred overnight. The mixture was extracted with diethyl ether. The aqueous phase was then acidified to pH 4 with 2M hydrochloric acid and extracted with ethyl acetate to give 0.06 g of 1-(benzyloxycarbonyl)-4-(tert.butoxycarbonyl)-2-piperazinecarboxylic acid as a white solid; MS: m/e 365 [M+H]$^+$.

(iii) 0.285 g of 1-(benzyloxycarbonyl)-4-(tert.butoxycarbonyl)-2-piperazinecarboxylic acid was dissolved in 10 ml of dry tetrahydrofuran and cooled to −15° C. while stirring. There was then added 0.09 g of N-ethylmorpholine followed immediately by 0.107 g of isobutyl chloroformate. The mixture was stirred for 5 minutes and then 0.2 g of tert.butylamine was added dropwise. Stirring was continued overnight, during which time the mixture was allowed to reach room temperature. The solvent was removed by evaporation and there was obtained a buff coloured oil which was partitioned between ethyl acetate and water. The organic phase was washed in sequence with 10% citric acid solution, sodium bicarbonate solution and saturated sodium chloride solution and dried over anhydrous sodium sulphate. The solvent was removed by evaporation to give 0.185 g of 1-(benzyloxycarbonyl)-4-(tert.butoxycarbonyl)-N-tert.butyl-2-piperazinecarboxamide as a light brown oil; MS: m/e 420 [M+H]$^+$.

(iv) 1.1 g of 1-(benzyloxycarbonyl)-4-(tert.butoxycarbonyl)-N-tert.butyl-2-piperazinecarboxamide were dissolved in 40 ml of ethanol. 0.1 g of 10% palladium-on-carbon was added and the mixture was hydrogenated at room temperature and under atmospheric pressure for 2 hours. The catalyst was filtered off. The filtrate was evaporated to give 0.74 g of crude product which was purified by flash chromatography on silica gel using 5% methanol in dichloromethane for the elution. After evaporation of the solvents there was obtained 0.44 g of 4-(tert.butoxycarbonyl)-N-tert.butyl-2-piperazinecarboxamide as an oil; MS: m/e 286 [M+H]$^+$.

(v) 0.395 g of 4-(tert.butoxycarbonyl)-N-tert.butyl-2-piperazinecarboxamide was dissolved in 50 ml of dry isopropanol and treated with 0.413 g of 3(S)-(benzyloxyformamido)-1,2(S)-epoxy-4-phenylbutane. The mixture was stirred at room temperature for 72 hours. The solvent was removed by evaporation to give a brown semi-solid material which was purified by flash chromatography on silica gel using 5% methanol in dichloromethane for the elution. There was obtained 0.234 g of 1-[3(S)-(benzyloxyformamido)-2(R)-hydroxy-4-phenylbutyl]-4-(tert.butoxycarbonyl)-N-tert.butyl-2(R or S)-piperazinecarboxamide as a mixture of diastereomers.

(vi) 0.234 g of 1-[3(S)-(benzyloxyformamido)-2(R)-hydroxy-4-phenylbutyl]-4-(tert.butoxycarbonyl)-N-tert.butyl-2(R and S)-piperazinecarboxamide was dissolved in 20 ml of ethanol and treated with 100 mg of 10% palladium-on-carbon. The mixture was hydrogenated at room temperature and under atmospheric pressure for 2.5 hours. The catalyst was filtered off and the filtrate was evaporated to give 0.17 g of 1-[3(S)-amino-2(R)-hydroxy-4-phenylbutyl]-4-(tert.butoxycarbonyl)-N-tert.butyl-2(R and S)-piperazinecarboxamide which was used without further purification.

EXAMPLE 97

0.035 g of 1-[3(S)-[[N-(benzyloxycarbonyl)-L-asparaginyl]amino]-2(R)-hydroxy-4-phenylbutyl]-4-(tert.butoxycarbonyl)-N-tert.butyl-2(R or S)-piperazinecarboxamide (isomer A) was dissolved in 5 ml of ethyl acetate and treated with 5 drops of a saturated solution of hydrogen chloride in ethyl acetate. The mixture was left to stand at room temperature for 1 hour and then worked-up to give, after recrystallization from ethanol/diethyl ether. 0.024 g of 1-[3(S)-[[N-(benzyloxycarbonyl)-L-asparaginyl]amino]-2(R)-hydroxy-4-phenylbutyl]-N-tert.butyl-2-(R or S)-piperazinecarboxamide hydrochloride (isomer A) of melting point 175°–180° C.

EXAMPLE 98

0.01 g of 1-[3(S)-[[N-(benzyloxycarbonyl)-L-asparaginyl]amino]-2(R)-hydroxy-4-phenylbutyl]-4-(tert.butoxycarbonyl)-N-tert.butyl-2(R or S)-piperazinecarboxamide (isomer B) was treated with hydrogen chloride in ethyl acetate as described in Example 97 to give 0.007 g of 1-[3(S)-[[N-(benzyloxycarbonyl)-L-asparaginyl]amino]-2(R)-hydroxy-4-phenylbutyl]-N-tert.butyl-2(R or S)-piperazinecarboxamide hydrochloride as a very hygroscopic solid; MS: m/e 597 [M+H]$^+$.

EXAMPLE 99

In a manner analogous to that described in Example 92, from 0.091 g of N-(benzyloxycarbonyl)-3-cyano-L-alanine, 0.05 g of hydroxybenzotriazole. 0.076 g of dicyclohexylcarbodiimide and 0.164 g of 1-[3(S)-amino-2(R)-hydroxy-4-phenylbutyl]-4-(tert.butoxycarbonyl)-N-tert.butyl-2(R,S)-piperazinecarboxamide there was obtained 0.075 g of a 60:40 mixture of diastereomers of 1-[3(S)-[[N-(benzyloxycarbonyl)-3-cyano-L-alanyl]amino]-2(R)-hydroxy-4-phenylbutyl]-4-(tert.butoxycarbonyl)-N-tert.butyl-2-piperazinecarboxamide as a buff coloured solid of melting point 80°–85° C.

EXAMPLE 100

In a manner analogous to that described in Example 92, from 0.108 g of 3-cyano-N-(2-naphthoyl)-L-alanine, 0.054 g of hydroxybenzotriazole, 0.083 g of dicyclohexylcarbodiimide and 0.18 g of 1-[3(S)-amino-2(R)-hydroxy-4-phenylbutyl]-4-(tert.butoxycarbonyl)-N-tert.butyl-2(R,S)-piperazinecarboxamide there was obtained 0.015 g of a 1:1:1:1 mixture of isomers of 4-(tert.butoxycarbonyl)-N-tert.butyl-1-[3(S)-[[3-cyano-N-(2-naphthoyl)-L-alanyl]amino]-2(R)-hydroxy-4-phenylbutyl]-2(R,S)-piperazinecarboxamide as a solid; MS: m/e 699 [M+H]$^+$.

The 3-cyano-N-(2-naphthoyl)-L-alanine used as the starting material was prepared as follows:

0.114 g of 3-cyano-L-alanine was dissolved in 5 ml of 1N sodium hydroxide solution and treated with 0.285 g of 2-naphthoyl chloride at 0° C. After acidification with 2M hydrochloric acid and flash chromatography on silica gel using 25% methanol in dichloromethane for the elution there was obtained 0.049 g of 3-cyano-N-(2-naphthoyl)-L-alanine of melting point 95°–100° C.

EXAMPLE 101

In a manner analogous to that described in Example 92, from 0.048 g of 1-[3(S)-[[L-asparaginyl]amino]-2(R)-hydroxy-4-phenylbutyl]-4-(tert.butoxycarbonyl)-4-tert.butyl-2(R and S)-piperazinecarboxamide, 0.015 g of quinaldic acid, 0.012 g of hydroxybenzotriazole and 0.018 g of dicyclohexylcarbodiimide there were obtained, after extensive flash chromatography on silica gel using 10% methanol in dichloromethane for the elution, 0.004 g of a pure single isomer A, 4-(tert.butoxycarbonyl)-N-tert.butyl-1-[2(R)-hydroxy-4-phenyl-3(S)-[[N-(2-quinolylcarbonyl)-L-asparaginyl]amino]butyl]-2(R or S)-piperazinecarboxamide, MS: m/e 718 [M+H]$^+$, and 0.003 g of a single isomer B, 4-(tert.butoxycarbonyl)-N-tert.butyl -1-[2(R)-hydroxy-4-phenyl-3(S)-[[N-(2-quinolylcarbonyl)-L-asparaginyl]amino]butyl]-2(R or S)-piperazine carboxamide; MS: m/e 718 [M+H]$^+$.

The 1-[3(S)-[[L-asparaginyl]amino]-2(R)-hydroxy-4-phenylbutyl]-4-(tert.butoxycarbonyl)-4-tert.butyl-2(R and S)-piperazinecarboxamide used as the starting material was prepared as follows:

0.06 g of 1-[3(S)-[[N-(benzyloxycarbonyl)-L-asparaginyl]amino]-2(R)-hydroxy-4-phenylbutyl]-4-(tert.butoxycarbonyl)-N-tert.butyl-2(R,S)-piperazinecarboxamide (i.e. the product of Example 96 prior to the separation of isomers A and B) was dissolved in 20 ml of ethanol. 0.03 g of palladium-on-carbon was added and the mixture was hydrogenated at room temperature and under atmospheric pressure for 2 hours. The catalyst was filtered off and the filtrate was evaporated to give 0.048 g of 1-[3(S)-[[L-asparaginyl] amino]-2(R)-hydroxy-4-phenylbutyl]-4-(tert.butoxycarbonyl)-4-tert.butyl-2-piperazinecarboxamide which was used without further purification.

EXAMPLE 102

In a manner analogous to that described in Example 92, from 0.151 g of N-(benzyloxycarbonyl)-3-cyano-L-alanine, 0.082 g of hydroxybenzotriazole, 0.126 g of dicyclohexylcarbodiimide and 0.212 g of 1-[3(S)-amino-2(R)-hydroxy-4-phenylbutyl]-N-tert.butyl-2(S)-piperidinecarboxamide there was obtained, after recrystallization from diethyl ether/n-hexane, 0.085 g of 1-[3(S)-[[N-(benzyloxycarbonyl)-3-cyano-L-alanyl]amino]-2(R)-hydroxy-4-phenylbutyl]-N-tert.butyl-2(S)-piperidinecarboxamide as a white solid of melting point 74°–77° C.

EXAMPLE 103

In a manner analogous to that described in Example 92, from 0.372 g of N-(benzyloxycarbonyl)-L-aspartic acid, 0.189 g of hydroxybenzotriazole, 0.288 g of dicyclohexylcarbodiimide and 0.54 g of N$^2$-[3(S)-amino-2(R)-hydroxy-4-(2-naphthyl)butyl]-N$^1$-tert.butyl-L-prolinamide there was obtained, after recrystallization from isopropanol/n-hexane (1:4), 0.105 g of N$_2$-[3(S)-[[N-(benzyloxycarbonyl)-L-asparaginyl]amino]-2(R)-hydroxy-4-(2-naphthyl)butyl]-N$^1$-tert.butyl-L-prolinamide of melting point 149°–151° C.

The $N_2$-[3(S)-amino-2(R)-hydroxy-4-(2-naphthyl)butyl]-$N^1$-tert.butyl-L-prolinamide used as the starting material was prepared as follows:

(i) 5 g of 3-(2-naphthyl)-L-alanine and 0.93 g of sodium hydroxide in 12 ml of water were cooled to 0° C. and stirred while a solution of 1.4 g of sodium hydroxide in 9 ml of water and 5 ml of benzyl chloroformate were added simultaneously during 10 minutes. Stirring was continued for 2 hours and the mixture was allowed to come to room temperature. The mixture was diluted with water and then extracted with diethyl ether. The aqueous layer was acidified with 4 ml of concentrated hydrochloric acid and extracted with ethyl acetate. The ethyl acetate extracts were back-washed with water. The combined ethyl acetate extracts were dried over sodium sulphate, filtered, evaporated and triturated with petroleum ether (boiling point 40°–60° C.) to give 7.5 g of N-(benzyloxycarbonyl)-3-(2-naphthyl)-L-alanine of melting point 109°–111° C.

(ii) A solution of 7.5 g of N-(benzyloxycarbonyl)-3-(2-naphthyl)-L-alanine in 20 ml of dry tetrahydrofuran was stirred at –8° C. and treated with 3.5 ml of N-ethylmorpholine followed by 4 ml of isobutyl chloroformate, added dropwise over a period of 10 minutes. The mixture was stirred at –8° C. for a further 20 minutes and cold (0° C.) anhydrous diethyl ether was added. The resulting white precipitate was filtered off and the cold filtrate was added dropwise to 100 ml of a stirred, cold (–8° C.) solution of diazomethane in diethyl ether. The cooling was removed and the solution was stirred for 3 hours. Water was added while stirring. The organic phase was washed in sequence with water, sodium bicarbonate solution and saturated sodium chloride solution and then dried over sodium sulphate. The solvent was removed by evaporation to give a yellow oil which, on evaporation with petroleum ether (boiling point 40°–60° C.), gave 9.4 g of a solid. Trituration of this solid with diethyl ether and refrigeration at 4° C. overnight gave 3.2 g of benzyl [3-diazo-1(S)-[(2-naphthyl)methyl]-2-oxopropyl] carbamate.

(iii) 3.13 g of benzyl [3-diazo-1(S)-[(2-naphthyl)methyl]-2-oxopropyl]carbamate were dissolved in 200 ml of anhydrous diethyl ether and stirred while hydrogen chloride gas was bubbled through the solution. After 1 hour the initially-precipitated solid became more granular and excess hydrogen chloride was being emitted. Then, the solvent was removed by evaporation at room temperature and the resulting white solid was dried and freed from entrained hydrogen chloride in a vacuum over sodium hydroxide for 2 hours. The resulting benzyl [3-chloro-1(S)-[(2-naphthyl)methyl]-2-oxopropyl] carbamate was used immediately in the next step.

(iv) The foregoing benzyl [3-chloro-1(S)-[(2-naphthyl)methyl]-2-oxopropyl] carbamate was dissolved in 100 ml of 10% aqueous tetrahydrofuran, cooled to 0° C. and treated with 0.456 g of sodium borohydride which was added carefully as the solid. The mixture was stirred at 0° C. for 1 hour and then at room temperature overnight. The mixture was evaporated to give a white solid which was partitioned between dichloromethane and water. The stirred mixture was carefully acidified to pH 1 with concentrated hydrochloric acid. The phases were separated and the aqueous phase was back-extracted with dichloromethane. The combined organic phases were dried over anhydrous sodium sulphate and evaporated to give 4.325 g of crude product of melting point 155°–160° C. This crude product was extracted with boiling n-hexane. After removal of the solvent by evaporation the residue was recrystallized from ethyl acetate/n-hexane to give 1.046 g of pure benzyl [3-chloro-2(S)-hydroxy-1(S)-[(2-naphthyl)methyl]propyl] carbamate of melting point 173°–174° C.

(v) 1.02 g of benzyl [3-chloro-2(S)-hydroxypropyl-1(S)-[(2-naphthyl)methyl]propyl] carbamate were stirred in 40 ml of ethanol with 4 ml of 0.7M potassium hydroxide solution in ethanol for 0.75 hours. The solvent was removed by evaporation and the residue was partitioned between dichloromethane and water. The organic phase was dried over anhydrous sodium sulphate and evaporated to give a white solid which was recrystallized from ethyl acetate/n-hexane. There was obtained 0.879 g of 3(S)-(benzyloxyformamido)-1,2(S)-epoxy-4-(2-naphthyl)butane as a white solid of melting point 115°–116° C.

(vi) 0.465 g of 3(S)-(benzyloxyformamido)-1,2(S)-epoxy-4-(2-naphthyl)butane and 0.251 g of L-proline tert.butylamide in 10 ml of dry isopropanol was heated at 80° C. for 23 hours and worked-up as described in Example 92(i) to give 0.483 g of $N_2$-[3(S)-(benzyloxyformamido)-2(R)-hydroxy-4-(2-naphthyl)butyl]-$N^1$-tert.butyl-L-prolinamide as a white foam melting at about 75°–85° C.

(vii) A solution of 0.725 g of $N_2$-[3(S)-(benzyloxyformamido)-2(R)-hydroxy-4-(2-naphthyl)butyl]-$N^1$-tert.butyl-L-prolinamide was dissolved in 25 ml of ethanol and hydrogenated at room temperature and under atmospheric pressure over 0.5 g of 10% palladium-on-carbon for 20 hours. The catalyst was filtered off and the filtrate was evaporated to give 0.54 g of $N_2$-[3(S)-amino-2(R)-hydroxy-L-(2-naphthyl)butyl]-$N^1$-tert.butyl-L-prolinamide as a white foam which was used without further purification.

EXAMPLE 104

In a manner analogous to that described in Example 92, from 0.133 g of N-(benzyloxycarbonyl)-L-asparagine, 0.068 g of hydroxybenzotriazole, 0.103 g of dicyclohexylcarbodiimide and 0.16 g of $N_2$-[3(S)-amino-2(R)-hydroxy-4-phenylbutyl]-$N^1$-tert.butyl-4(R)-hydroxy-L-prolinamide, but using dichloromethane in place of ethyl acetate as the partitioning solvent and 20% methanol in dichloromethane for the chromatography and carrying out the re-evaporation with diethyl ether, there was obtained 0.1 g of $N_2$-[3(S)-[N-(benzyloxycarbonyl)-L-asparaginylamino]-2(R)-hydroxy-4-phenylbutyl]-$N^1$-tert.butyl-4(R)-hydroxy-L-prolinamide of melting point 115° C.

The $N_2$-[3(S)-amino-2(R)-hydroxy-4-phenylbutyl]-$N^1$-tert.butyl-4(R)-hydroxy-L-prolinamide used as the starting material was prepared as follows:

(i) 2.65 g of N-(benzyloxycarbonyl)-4(R)-hydroxy-L-proline were dissolved in 10 ml of dry tetrahydrofuran and cooled to –10° C. while stirring with a magnetic stirrer. 1.15 g of N-ethylmorpholine were added followed immediately by 1.36 g of isobutyl chloroformate. The mixture was stirred at –10° C. for 30 minutes and then 2.19 g of tert.butylamine were added. Stirring was continued at –10° C. for 1 hour, the mixture was allowed to warm to room temperature during 2 hours and was then left to stand for 2 hours. The solvent was removed by evaporation in a vacuum and the residue was partitioned between ethyl acetate and water. The organic layer was washed with 10% citric acid solution and sodium bicarbonate solution and then dried over sodium sulphate. The solvent was removed by evaporation to give a solid which was triturated with diethyl ether and filtered off. There were obtained 2.23 g of crude product which was recrystallized from ethyl acetate/diethyl ether to give 1.57 g of $N_2$-(benzyloxycarbonyl)-$N^1$-tert.butyl-4(R)-hydroxy-L-prolinamide of melting point 128°–130° C.

(ii) 0.224 g of $N_2$-(benzyloxycarbonyl)-$N^1$-tert.butyl-4(R)-hydroxy-L-prolinamide was dissolved in 20 ml of ethanol and hydrogenated over 50 mg of 10% palladium-on-carbon at room temperature and under atmospheric pressure for 2 hours. The catalyst was filtered off and the filtrate was evaporated to give 0.13 g of $N^1$-tert.butyl-4(R)-hydroxy-L-prolinamide which was used in the next step without further purification.

(iii) 0.13 g of $N^1$-tert.butyl-4(R)-hydroxy-L-prolinamide and 0.208 g of 3(S)-(benzyloxyformamido)-1,2(S)-epoxy-4-phenylbutane in 10 ml of dry isopropanol were heated at 80° C. for 24 hours. Working-up in a manner analogous to that described in Example 33(iii) gave, after trituration with diethyl ether, 0.236 g of $N_2$-[3(S)-(benzyloxyformamido)-2(R)-hydroxy-4-phenylbutyl]-$N^1$-tert.butyl-4(R)-hydroxy-L-prolinamide as a white gelatinous solid of melting point 135° C.

(iv) 0.226 g of $N^2$-[3(S)-(benzyloxyformamido)-2(R)-hydroxy-4-phenylbutyl]-$N^1$-tert.butyl-4(R)-hydroxy-L-prolinamide was dissolved in 20 ml of ethanol and hydrogenated over 40 mg of 10% palladium-on-carbon at room temperature and under atmospheric pressure for 2 hours. The catalyst was removed by filtration and the filtrate was evaporated to give 0.16 g of $N_2$-[3(S)-amino-2(R)-hydroxy-4-phenylbutyl]-$N^1$-tert.butyl-4(R)-hydroxy-L-prolinamide as a gum which was used without further purification.

EXAMPLE 105

In a manner analogous to that described in Example 92, but using dichloromethane in place of ethyl acetate as the partitioning solvent, using 20% methanol in dichloromethane for the chromatography and carrying out the re-evaporation with diethyl ether, from 0.067 g of N-(benzyloxycarbonyl)-L-asparagine, 0.034 g of hydroxybenzotriazole, 0.052 g of dicyclohexylcarbodiimide and 0.08 g of $N^2$-[3(S)-amino-2(R)-hydroxy-4-phenylbutyl]-$N^1$-tert.butyl-4(S)-hydroxy-L-prolinamide there was obtained 0.03 g of $N^2$-[3(S)-[[N-(benzyloxycarbonyl)-L-asparaginyl]amino]-2(R)-hydroxy-4-phenylbutyl]-$N^1$-tert.butyl-4(S)-hydroxy-L-prolinamide as a cream coloured solid melting at about 140° C.

The $N_2$-[3(S)-amino-2(R)-hydroxy-4-phenylbutyl]-$N^1$-tert.butyl-4(S)-hydroxy-L-prolinamide used as the starting material was prepared as follows:

(i) 1.7 g of N-(benzyloxycarbonyl)-4(S)-hydroxy-L-proline were dissolved in 15 ml of dry dimethylformamide while stirring and the solution was cooled to 0° C. 0.817 g of N-hydroxysuccinimide was added and the mixture was stirred while the temperature was allowed to rise to 20° C. The mixture was then stirred overnight at room temperature. The resulting dicyclohexylurea was filtered off and the filtrate was cooled to −10° C. 2 ml of tert.butylamine were then added while stirring. Stirring was continued while the mixture was allowed to warm to room temperature and the mixture was then stirred overnight. The separated solid was filtered off and the filtrate was evaporated in a vacuum to give a gum which was partitioned between ethyl acetate and water. The organic layer was washed with 10% citric acid solution and then with saturated sodium bicarbonate solution. The aqueous phases were back-extracted twice with ethyl acetate. The combined organic phases were dried over anhydrous sodium sulphate and evaporated to give a solid which was purified by flash chromatography on silica gel using 5% methanol in dichloromethane for the elution. There were obtained 1.36 g of a crude product which was recrystallized from ethyl acetate/diethyl ether/petroleum ether (boiling point 40°–60° C.) (1:4:4) and then stored at 4° C. in a refrigerator overnight. There were thus obtained 1.127 g of $N_2$-(benzyloxycarbonyl)-$N^1$-tert.butyl-4(S)-hydroxy-L-prolinamide of melting point 131°–132° C.

(ii) 0.224 g of $N_2$-(benzyloxycarbonyl)-$N^1$-tert-butyl-4(S)-hydroxy-L-prolinamide was hydrogenated in a manner analogous to that described in Example 104 (ii) to give 0.135 g of $N^1$-tert.butyl-4(S)-hydroxy-L-prolinamide as a gum-like solid which was used in the next step without purification.

(iii) 0.135 g of $N^1$-tert.butyl-4(S)-hydroxy-L-prolinamide and 0.208 g of 3(S)-(benzyloxyformamido)-1,2(S)-epoxy-4-phenylbutane in 10 ml of dry ethanol was stirred for 4 days at room temperature. The mixture was worked-up as described in Example 92(i), with the exception that the chromatography was carried out using 10% methanol in dichloromethane for the elution. There was obtained 0.11 g of $N_2$-[3(S)-(benzyloxyformamido)-2(R)-hydroxy-4-phenylbutyl]-$N^1$-tert.butyl-4(S)-hydroxy-L-prolinamide as a foam.

(iv) 0.11 g of $N_2$-[3(S)-(benzyloxyformamido)-2(R)-hydroxy-4-phenylbutyl]-$N^1$-tert.butyl-4(S)-hydroxy-L-prolinamide was dissolved in 10 ml of ethanol and hydrogenated over 20 mg of 10% palladium-on-carbon at room temperature and under atmospheric pressure for 2 hours. The catalyst was filtered off and the filtrate was evaporated to give 0.08 g of $N_2$-[3(S)-amino-2(R)-hydroxy-4-phenylbutyl]-$N^1$-tert.butyl-4(S)-hydroxy-L-prolinamide as a gum which was used without further purification.

EXAMPLE 106

In a manner analogous to that described in Example 92, but using dichloromethane in place of ethyl acetate as the partitioning solvent, using 20% methanol in dichloromethane for the chromatography and carrying out the re-evaporation with diethyl ether, from 0.105 g of N-(benzyloxycarbonyl)-L-asparagine, 0.054 g of hydroxybenzotriazole, 0.082 g of dicyclohexylcarbodiimide and 0.17 g of $N_2$-[3(S)-amino-2(R)-hydroxy-4-phenylbutyl]-4(R)-(tert.-butoxyformamido)-$N^1$-tert.butyl-L-prolinamide there was obtained 0.045 g of $N^2$-[3(S)-[[N-(benzyloxycarbonyl)-L-asparaginyl]amino]-2(R)-hydroxy-4-phenylbutyl]-4(R)-(tert.butoxyformamido)-$N^1$-tert.butyl-L-prolinamide as an off-white solid of melting point 170°–175° C.

The $N_2$-[3(S)-amino-2(R)-hydroxy-4-phenylbutyl]-4(R)-$N^1$-(tert.butoxyformamido)-$N^1$-tert.butyl-L-prolinamide used as the starting material was prepared as follows:

(i) 0.32 g of $N_2$-(benzyloxycarbonyl)-$N^1$-tert.butyl-4(S)-hydroxy-L-prolinamide was dissolved in 5 ml of dry pyridine while stirring, cooled to 0° C. and treated dropwise with 0.82 ml of methanesulphonyl chloride. The solution was stirred at 0° C. for a further 2 hours. The mixture was poured into a mixture of ice and water which was then extracted with ethyl acetate. The combined organic extracts were washed with 2M hydrochloric acid and then with saturated sodium bicarbonate solution and subsequently dried over anhydrous sodium sulphate. After evaporation there was obtained 0.5 g of $N^2$-(benzyloxycarbonyl)-$N^1$-tert.butyl-4(S)-(methanesulphonyloxy)-L-prolinamide as an oil which was used without further purification.

(ii) 0.5 g of $N_2$-(benzyloxycarbonyl)-$N^1$-tert.butyl-4(S)-(methanesulphonyloxy)-L-prolinamide was dissolved in 10 ml of dry dimethylformamide and treated with 0.330 g of sodium azide. The heterogeneous mixture was stirred and heated at 75° C. for 18 hours. The mixture was evaporated under an oil pump vacuum to give a solid which was partitioned between ethyl acetate and water. The ethyl acetate phase was washed with saturated sodium chloride solution and dried over anhydrous sodium sulphate. The solvent was removed by evaporation to give 0.345 g of $N_2$-(benzyloxycarbonyl)-4(R)-azido-$N^1$-tert.butyl-L-prolinamide in the form of a gum.

(iii) 0.345 g of $N^2$-(benzyloxycarbonyl)-4(R)-azido-$N^1$-tert.butyl-L-prolinamide was dissolved in 5 ml of dry tetrahydrofuran and the solution was evaporated. The residual gum was dissolved in 10 ml of dry tetrahydrofuran and treated under a nitrogen atmosphere with 0.262 g of triphenylphosphine. The resulting solution was left to stand under a nitrogen atmosphere at room temperature for 18 hours. 0.027 g of water was added and the solution was left to stand at room temperature for 24 hours. The solvent was then removed by evaporation and the residual gum was partitioned between water and diethyl ether. The aqueous phase was back-extracted with diethyl ether. The aqueous phase was then evaporated to give 0.09 g of $N_2$-(benzyloxycarbonyl)-4(R)-amino-$N^1$-tert-butyl-L-prolinamide as a gum. After standing overnight at room temperature the diethyl ether extracts were combined and evaporated to give 0.7 g of an oil which was chromatographed on silica gel using 10% methanol in dichloromethane for the elution to give a further 0.16 g of $N^2$-benzyloxycarbonyl)-4(R)-amino-$N^1$-tert.butyl-L-prolinamide as a gum.

(iv) 0.21 g of $N^2$-(benzyloxycarbonyl)-4(R)-amino-$N^1$-tert.-butyl-L-prolinamide was dissolved in a mixture of 5 ml of dioxane and 5 ml of water. 0.056 g of sodium bicarbonate was added to give a solution to which 0.144 g of di(tert.butyl) dicarbonate was added. The mixture obtained was stirred at room temperature overnight. Solvents were removed by evaporation and the residue was partitioned between water and diethyl ether. The aqueous phase was back-extracted with diethyl ether and then with ethyl acetate. The combined organic extracts were washed with saturated sodium chloride solution and dried over anhydrous sodium sulphate. The dried extracts were combined and evaporated to give 0.27 g of $N^2$-(benzyloxycarbonyl)-4(R)-(tert.butoxyformamido)-$N^1$-tert.butyl-L-prolinamide as an off-white foam.

(v) 0.25 g of $N_2$-(benzyloxycarbonyl)-4(R)-(tert.butoxyformamido)-$N^1$-tert.butyl-L-prolinamide was dissolved in ethanol and hydrogenated over 0.1 g of 10% palladium-on-carbon at room temperature and under atmospheric pressure for 4 hours. The catalyst was filtered off and the filtrate-was evaporated to give 0.17 g of 4(R)-(tert.butoxyformamido)-$N^1$-tert.butyl-L-prolinamide as a glass which was used without further purification.

(vi) 0.17 g of 4(R)-(tert.butoxyformamido)-$N^1$-tert.butyl-L-prolinamide and 0.178 g of 3(S)-(benzyloxyformamido)-1,2(S)-epoxy-4-phenylbutane in 15 ml of dry ethanol were stirred and the resulting solution was left to stand at room temperature for 4.5 days. The solution was then heated at 40° C. for 96 hours. Working-up as described in Example 92(i), with the exception that the chromatography was carried out using 10% methanol in dichloromethane for the elution, gave 0.230 g of $N_2$-[3(S)-(benzyloxyformamido)-2(R)-hydroxy-4-phenyl]butyl]-4(R)-(tert.butoxyformamido)-$N^1$-tert.butyl-L-prolinamide as a gum.

(vii) 0.22 g of $N_2$-[3(S)-(benzyloxyformamido)-2(R)-hydroxy-4-phenylbutyl]-4(R)-(tert.butoxyformamido)-$N^1$-tert.butyl-L-prolinamide was dissolved in 10 ml of ethanol and hydrogenated over 0.05 g of 10% palladium-on-carbon at room temperature and under atmospheric pressure for 2 hours. The catalyst was filtered off and the filtrate was evaporated to give 0.17 g of $N_2$-[3(S)-amino-2(R)-hydroxy-4-phenylbutyl]-4(R)-(tert.butoxyformamido)-$N^1$-tert.butyl-L-prolinamide as a gum which was used without further purification.

EXAMPLE 107

In a manner analogous to that described in Example 27, from 162 mg of 2-[[3(S)-[[L-asparaginyl]amino]-2(R)-hydroxy-4-phenyl]butyl]-N-tert.butyl-1,2,3,4-tetrahydropyrido[3,4-b]indole-1(R or S)-carboxamide, (isomer B), 55 mg of quinaldic acid, 43 mg of 1-hydroxybenzotriazole, 0.04 ml of N-ethylmorpholine and 66 mg of dicyclohexylcarbodiimidethere were obtained, after chromatography on silica gel using 3% methanol in ethyl acetate for the elution, 95 mg of N-tert.butyl-1,2,3,4-tetrahydro-2-[2(R)-hydroxy-4-phenyl-3(S)-[[N-(2-quinolylcarbonyl)-L-asparaginyl]amino] butyl]pyrido[3,4-b]indole-1(R or S)-carboxamide; MS: m/e 707 [M+H]$^+$.

The 2-[[3(S)-[[L-asparaginyl]amino]-2(R)-hydroxy-4-phenyl]butyl]-N-tert.butyl-1,2,3,4-tetrahydropyrido[3,4-b]indole-1(R or S)-carboxamide used as the starting material was prepared by hydrogenating 2-[3(S)-[[N-(benzyloxycarbonyl)-L-asparaginyl]amino]-2(R)-hydroxy-4-phenylbutyl]-N-tert.butyl-1,2,3,4-tetrahydropyrido[3,4-b]indole-1(R or S)-carboxamide.

EXAMPLE 108

A solution of 154 mg of trans-2-[3(S)-[(L-asparaginyl)amino]-2(R)-hydroxy-4-phenylbutyl]-N-tert.butyl-decahydro-(4aR,8aS)-isoquinoline-3(S)-carboxamide and 52 mg of quinaldic acid in 6 ml of dry tetrahydrofuran is cooled in an ice/salt mixture. 41 mg of hydroxybenzotriazole, 35 mg=of N-ethylmorpholine and 68 mg of dicyclohexylcarbodiimide are added and the mixture is stirred for 64 hours. The mixture is diluted with ethyl acetate and filtered. The filtrate is washed with aqueous sodium bicarbonate solution and with sodium chloride solution and then evaporated. The residue is chromatographed on silica gel using dichloromethane/methanol (9:1) for the elution to give trans-N-tert.butyl-decahydro-2-[2(R)-hydroxy-4-phenyl-3(S)-[[N-(2-quinolylcarbonyl)-L-asparaginyl]amino]butyl]-(4aR,8aS)-isoquinoline-3(S)-carboxamide.

The trans-2-[3(S)-[(L-asparaginyl)amino]-2(R)-hydroxy-4-phenylbutyl]-N-tert.butyl-decahydro-(4aR,8aS)-isoquinoline-3(S)-carboxamide to be used as the starting material is prepared by hydrogenating trans-2-[3(S)-[[N-(benzyloxycarbonyl)-L-asparaginyl]amino]-2(R)-hydroxy-4-phenylbutyl]-N-tert.butyl-decahydro-(4aR,8aS)-isoquinoline-3(S)-carboxamide.

EXAMPLE 109

A solution of 1.02 g of 1-[3(S)-amino-2(R)-hydroxy-4-phenylbutyl]-N-tert.butyl-2(S)-piperidinecarboxamide and 685 mg of N-(tert.butoxycarbonyl)-S-methyl-L-cysteine in 7 ml of dry tetrahydrofuran was cooled in an ice/salt mixture. 394 mg of hydroxybenzotriazole, 335 mg of N-ethylmorpholine and 661 mg of dicyclohexylcarbodiimide were added and the mixture was stirred for 3 hours. The mixture was diluted with ethyl acetate and filtered. The filtrate was washed with aqueous sodium bicarbonate solution and with sodium chloride solution and then evaporated. The solvent was removed by evaporation and the residue was chromatographed on silica gel using dichloromethane/methanol (96:4) for the elution to give 630 mg of 1-[3(S)-[[N-(tert.butoxycarbonyl)-L-cysteinyl]amino]-2(R)-hydroxy-4-phenylbutyl]-N-tert.butyl-2(S)-piperidinecarboxamide in the form of a white solid; MS: m/e 565 [M+H]$^+$.

EXAMPLE 110

A solution of 650 mg of N-tert.butyl-1-[3(S)-[(L-cysteinyl)amino]-2(R)-hydroxy-4-phenylbutyl]-2(S)-piperidinecarboxamide and 242 mg of quinaldic acid was cooled in an ice/salt mixture. 189 mg of hydroxybenzotriazole, 161 mg of N-ethylmorpholine and 317 mg of dicyclohexylcarbodiimide were added and the mixture was stirred for 64 hours. The mixture was diluted with ethyl acetate and filtered, and the filtrate was then evaporated. The residue was partitioned between dichloromethane and aqueous sodium bicarbonate solution. The organic phase was washed with sodium chloride solution and then evaporated. The residue was chromatographed on silica gel using dichloromethane/methanol (19:1) for the elution to give 350 mg of N-tert.butyl-1-[2(R)-hydroxy-4-phenyl-3(S)-[[N-(2-quinolylcarbonyl)-L-cysteinyl]amino]butyl]-2(S)-piperidinecarboxamide as a white solid; MS: m/e 620 [M+H]$^+$.

The N-tert.butyl-1-[3(S)-[(L-cysteinyl)amino]-2(R)-hydroxy-4-phenylbutyl]-2(S)-piperidinecarboxamide used as the starting material was prepared as follows:

A solution of 930 mg of 1-[3(S)-[[N-(tert.butoxycarbonyl)-L-cysteinyl]amino]-2(R)-hydroxy-4-phenylbutyl]-N-tert.butyl-2(S)-piperidinecarboxamide in 7 ml of trifluoroacetic acid was stirred at 20° C. for 1 hour. The mixture was then evaporated to dryness and the residue was partitioned between dichloromethane and aqueous sodium bicarbonate solution. The organic phase was evaporated to give 650 mg of N-tert.butyl-1-[3(S)-[(L-cysteinyl)amino]-2(R)-hydroxy-4-phenylbutyl]-2(S)-piperidinecarboxamide as a colourless gum; MS: m/e [M+H]$^+$.

EXAMPLE 111

15 mg of freshly distilled acetyl chloride were added to a solution, which was cooled to 0° C. and stirred, of 12 mg of 4(R)-amino-N$^2$-[3(S)-[[N-benzyloxycarbonyl)-L-asparaginyl]amino]-2(R)-hydroxy-4-phenyl-butyl]-N$^1$-tert.butyl-L-prolinamide hydrochloride and 21 mg of sodium bicarbonate in 0.5 ml of water and 0.25 ml of dimethylformamide. The mixture was stirred vigorously at 0° C. for 5 hours and then left to stand at room temperature overnight. The mixture was diluted with water and extracted with dichloromethane. The combined dichloromethane extracts were evaporated to give a gum which was purified by flash chromatography on silica gel using 20% methanol in dichloromethane for the elution. There were obtained 2 mg of 4(R)-acetylamino-N$_2$-[3(S)-[[N-(benzyloxycarbonyl)-L-asparaginyl]amino]-2(R)-hydroxy-4-phenylbutyl]-N$^1$-tert-butyl-L-prolinamide as a semi-solid; MS: m/e 639 [M+H]$^+$.

The 4(R)-amino-N$^2$-[3(S)-[[N-(benzyloxycarbonyl)-L-asparaginyl]amino]-2(R)-hydroxy-4-phenylbutyl]-N$^1$-tert.-butyl-L-prolinamide hydrochloride used as the starting material was prepared as follows:

29 mg of N$_2$-[3(S)-[[N$_2$-(benzyloxycarbonyl)-L-asparaginyl]amino]-2(R)-hydroxy-4-phenylbutyl]-4(R)-(tert-butoxyformamido)-N$^1$-tert.butyl-L-prolinamide were dissolved in 0.5 ml of a saturated solution of hydrogen chloride in ethyl acetate and left to stand at room temperature for 1 hour. The solution was evaporated and the residue was triturated with diethyl ether and stored at 4° C. overnight. The separated solid was filtered off and washed with diethyl ether to give 19 mg of 4(R)-amino-N$^2$-[3(S)-[[N-(benzyloxycarbonyl)-L-asparaginyl]amino]-2(R)-hydroxy-4-phenylbutyl]-N$^1$-tert.butyl-L-prolinamide hydrochloride as a solid of melting point 206°–210° C.

The following Example illustrates the manufacture of a pharmaceutical preparation containing a compound of formula I or a pharmaceutically acceptable acid addition salt thereof as the active ingredient:

EXAMPLE A

An aqueous solution of the active ingredient is filtered sterile and mixed while warming with a sterile gelatine solution, which contains phenol as a preserving agent, using amounts such that 1.00 ml of the resulting solution contains 3.0 mg of active ingredient, 150.0 mg of gelatine, 4.7 mg of phenol and distilled water ad 1.0 ml. The mixture is filled into vials of 1.0 ml capacity under aseptic conditions.

We claim:

1. A compound of the formula

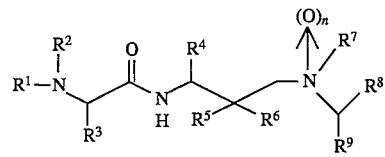

wherein n is zero or 1; R$^1$ is cycloalkylcarbonyl, aralkanoyl, and aroyl; R$^2$ is hydrogen; R$^3$ is alkyl, cycloalkyl, aryl, aralkyl, cyanoalkyl, alkylsulphinylalkyl, carbamoylalkyl or alkoxycarbonylalkyl or, when n is zero, R$^3$ is additionally alkylthioalkyl or, when n is 1, R$^3$ can also be alkylsulphonylalkyl; R$^4$ is alkyl, cycloalkyl, cycloalkylalkyl, aryl or aralkyl; R$^5$ is hydrogen and R$^6$ is hydroxy or R$^5$ and R$^6$ together are oxo; —N(R$^7$)—CH(R$^8$)(R$^9$) is selected from the group consisting of

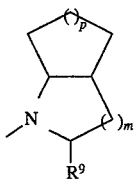  (f)

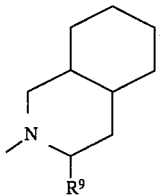  (g)

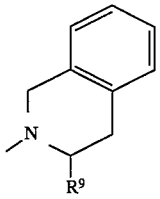  (j)

where m is 2 and p is 1 or 2, R$^9$ is alkoxycarbonyl, monoalkylcarbamoyl, monoaralkylcarbamoyl, monoarylcarbamoyl or a group of the formula

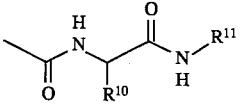  (b)

where R$^{10}$ and R$^{11}$ are alkyl, or the pharmaceutically acceptable addition salts thereof.

2. The compound of claim 1 wherein n is zero.

3. The compound of claim 2 wherein $R^3$ is alkyl, cycloalkyl, aryl, aralkyl, cyanoalkyl, alkylthioalkyl, carbamoylalkyl or alkoxycarbonylalkyl.

4. The compound of claim 3 wherein $R^1$ is 2-naphthoyl, 1-hydroxy-2-naphthoyl, 3-hydroxy-2-naphthoyl or 3-benzyloxy-2-naphthoyl, and $R^2$ is hydrogen.

5. The compound of claim 4 wherein $R^3$ is cyanomethyl, methylthiomethyl or carbamoylmethyl, $R^4$ is benzyl, and $R^5$ is hydrogen.

6. The compound of claim 5 wherein $R^9$ is selected from tert.butoxycarbonyl, isobutylcarbamoyl, tert.butylcarbamoyl or

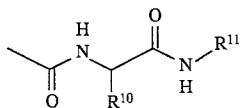 (b)

wherein $R^{10}$ is sec.butyl and $R^{11}$ is isobutyl.

7. The compound of claim 1 wherein $R^3$ is heterocyclylalkyl.

8. A method for the treatment of viral infections, comprising administration of an antivirally effective amount of the compound of formula I in claim 1.

9. A method for the treatment of viral infections, comprising administration of an antivirally effective amount of the compound of formula I in claim 7.

10. A pharmaceutical composition comprising a compound of formula I of claim 1, and one or more therapeutically inert exipients.

11. A pharmaceutical composition comprising a compound of formula I of claim 7, one or more therapeutically inert exipients.

* * * * *